(12) United States Patent
Clauson et al.

(10) Patent No.: US 12,161,585 B2
(45) Date of Patent: Dec. 10, 2024

(54) SYSTEMS AND DEVICES FOR DELIVERING FLUIDS TO THE EYE AND METHODS OF USE

(71) Applicant: Eyenovia, Inc., New York, NY (US)

(72) Inventors: Luke W. Clauson, Reno, NV (US); Rex Dwyer, Reno, NV (US); Matthew Newell, Reno, NV (US); Michael Owens, Reno, NV (US)

(73) Assignee: Eyenovia, Inc., New York, NY (US)

( * ) Notice: Subject to any disclaimer, the term of this patent is extended or adjusted under 35 U.S.C. 154(b) by 807 days.

(21) Appl. No.: 17/119,905

(22) Filed: Dec. 11, 2020

(65) Prior Publication Data

US 2021/0177650 A1 Jun. 17, 2021

Related U.S. Application Data

(60) Provisional application No. 62/946,727, filed on Dec. 11, 2019.

(51) Int. Cl.
*A61F 9/00* (2006.01)
*A61K 31/135* (2006.01)
(Continued)

(52) U.S. Cl.
CPC .......... *A61F 9/0008* (2013.01); *A61K 31/135* (2013.01); *A61K 31/222* (2013.01);
(Continued)

(58) Field of Classification Search
CPC ... A61F 9/0008; A61K 31/135; A61K 31/222; A61K 31/4164; A61K 31/4409; A61K 31/46; A61K 47/02; A61K 47/186; A61K 9/0048; A61K 9/08; A61K 31/138; A61K 31/4178; A61K 31/5575; A61M 2210/0612; A61M 35/003; A61P 27/02; A61P 27/06; B05B 17/04; B05B 17/0607; B05B 17/0623; B05B 17/0646
See application file for complete search history.

(56) References Cited

U.S. PATENT DOCUMENTS

| 558,866 A | 4/1896 | Vaughn |
| 1,482,747 A | 2/1924 | Howe |

(Continued)

FOREIGN PATENT DOCUMENTS

| CA | 2873582 A1 | 11/2012 |
| CN | 203609747 U | 5/2014 |

(Continued)

OTHER PUBLICATIONS

Edelhauser, H.F. et al. (1979). "The Effect of Phenylephrine on the Cornea." Arch Ophthalmol., 97(5):937-947.

(Continued)

*Primary Examiner* — Kai H Weng
*Assistant Examiner* — Alessandro R Del Priore
(74) *Attorney, Agent, or Firm* — Mintz Levin Cohn Ferris Glovsky and Popeo, P.C.

(57) ABSTRACT

A device for delivering a volume of fluid to an eye including a base having a drive mechanism and a disposable fluid cartridge configured to releasably couple to the base to form the device. Related systems, devices, compositions, and methods of use are provided.

52 Claims, 21 Drawing Sheets

(51) Int. Cl.
   *A61K 31/222*    (2006.01)
   *A61K 31/4164*   (2006.01)
   *A61K 31/4409*   (2006.01)
   *A61K 31/46*     (2006.01)
   *A61K 47/02*     (2006.01)
   *A61K 47/18*     (2017.01)

(52) U.S. Cl.
   CPC ...... *A61K 31/4164* (2013.01); *A61K 31/4409* (2013.01); *A61K 31/46* (2013.01); *A61K 47/02* (2013.01); *A61K 47/186* (2013.01)

(56) References Cited

U.S. PATENT DOCUMENTS

| | | |
|---|---|---|
| 1,493,410 A | 5/1924 | Wolcott |
| 1,799,529 A | 4/1931 | Poetsch |
| 1,988,637 A | 1/1935 | Tinkham |
| 2,189,643 A | 2/1940 | Ward |
| 2,200,008 A | 5/1940 | Nowak |
| 2,249,608 A | 7/1941 | Greene |
| 2,322,808 A | 6/1943 | Hothersall |
| 2,552,857 A | 5/1951 | Knapp |
| 2,595,317 A | 5/1952 | White, Jr. |
| 2,698,619 A | 1/1955 | Beacham et al. |
| 2,987,439 A | 6/1961 | Wittlinger |
| 3,170,462 A | 2/1965 | Hall |
| 3,187,757 A | 6/1965 | Jones et al. |
| 3,237,809 A | 3/1966 | Daragan et al. |
| 3,310,830 A | 3/1967 | Gattone |
| 3,314,426 A | 4/1967 | Carroll |
| 3,439,674 A | 4/1969 | Lelicoff |
| 3,602,399 A | 8/1971 | Litman et al. |
| 3,658,257 A | 4/1972 | Rood |
| 3,709,235 A | 1/1973 | Washburn et al. |
| 3,734,585 A | 5/1973 | Conru |
| 3,779,245 A | 12/1973 | Windsor |
| 3,780,950 A | 12/1973 | Brennan |
| 3,795,351 A | 3/1974 | Lehmann |
| 3,812,854 A | 5/1974 | Michaels et al. |
| 3,826,258 A | 7/1974 | Abraham |
| 3,845,764 A | 11/1974 | Windsor |
| 3,892,235 A | 7/1975 | Van Amerongen et al. |
| 3,901,443 A | 8/1975 | Mitsui et al. |
| 3,906,949 A | 9/1975 | Holland |
| 3,913,575 A | 10/1975 | Windsor |
| 3,934,585 A | 1/1976 | Maurice |
| 4,002,168 A | 1/1977 | Petterson |
| 4,012,798 A | 3/1977 | Liautaud |
| 4,052,985 A | 10/1977 | Coleman et al. |
| 4,067,499 A | 1/1978 | Cohen |
| 4,098,431 A | 7/1978 | Palmer et al. |
| D249,709 S | 9/1978 | Trovinger |
| 4,119,096 A | 10/1978 | Drews |
| 4,122,556 A | 10/1978 | Poler |
| 4,131,115 A | 12/1978 | Peng |
| 4,173,226 A | 11/1979 | Shell |
| 4,175,704 A | 11/1979 | Cohen |
| 4,175,706 A | 11/1979 | Gerstmann |
| 4,264,837 A | 4/1981 | Gaboriaud |
| 4,296,071 A | 10/1981 | Weiss et al. |
| 4,319,155 A | 3/1982 | Nakai et al. |
| 4,323,530 A | 4/1982 | Voss et al. |
| 4,338,936 A | 7/1982 | Nelson |
| 4,356,528 A | 10/1982 | Coffee |
| 4,381,533 A | 4/1983 | Coffee |
| 4,388,343 A | 6/1983 | Voss et al. |
| 4,390,542 A | 6/1983 | Schachar |
| 4,398,909 A | 8/1983 | Portnoff |
| 4,465,234 A | 8/1984 | Maehara et al. |
| 4,471,890 A | 9/1984 | Dougherty |
| 4,476,515 A | 10/1984 | Coffee |
| 4,479,609 A | 10/1984 | Maeda et al. |
| 4,493,119 A | 1/1985 | Baumann |
| 4,533,082 A | 8/1985 | Maehara et al. |
| 4,543,096 A | 9/1985 | Keene |
| 4,544,570 A | 10/1985 | Plunkett et al. |
| 4,564,016 A | 1/1986 | Maurice et al. |
| 4,580,721 A | 4/1986 | Coffee et al. |
| 4,605,167 A | 8/1986 | Maehara |
| 4,605,398 A | 8/1986 | Herrick |
| 4,627,845 A | 12/1986 | DeMotte |
| 4,641,384 A | 2/1987 | Landsberger et al. |
| 4,642,581 A | 2/1987 | Erickson |
| 4,658,290 A | 4/1987 | McKenna et al. |
| 4,659,014 A | 4/1987 | Soth et al. |
| 4,679,551 A | 7/1987 | Anthony |
| 4,685,906 A | 8/1987 | Murphy |
| 4,691,885 A | 9/1987 | Lawrance |
| 4,701,167 A | 10/1987 | Chekan |
| 4,702,418 A | 10/1987 | Carter et al. |
| 4,706,848 A | 11/1987 | D'Andrade |
| 4,740,206 A | 4/1988 | Allander |
| 4,742,713 A | 5/1988 | Abe et al. |
| 4,750,650 A | 6/1988 | Ling |
| 4,750,902 A | 6/1988 | Wuchinich et al. |
| 4,758,237 A | 7/1988 | Sacks |
| 4,758,727 A | 7/1988 | Tomei et al. |
| 4,759,755 A | 7/1988 | Hein et al. |
| 4,779,768 A | 10/1988 | St. Amand |
| 4,784,652 A | 11/1988 | Wikstrom |
| 4,790,479 A | 12/1988 | Matsumoto et al. |
| 4,792,334 A | 12/1988 | Py |
| 4,793,339 A | 12/1988 | Matsumoto et al. |
| 4,796,807 A | 1/1989 | Bendig et al. |
| 4,798,599 A | 1/1989 | Thomas |
| 4,809,914 A | 3/1989 | Goncalves |
| 4,815,661 A | 3/1989 | Anthony |
| 4,826,025 A | 5/1989 | Abiko et al. |
| 4,850,534 A | 7/1989 | Takahashi et al. |
| 4,863,073 A | 9/1989 | Burt et al. |
| 4,863,443 A | 9/1989 | Hornung |
| 4,863,457 A | 9/1989 | Lee |
| 4,871,091 A | 10/1989 | Preziosi |
| 4,877,989 A | 10/1989 | Drews et al. |
| 4,880,146 A | 11/1989 | Hudgins |
| 4,881,283 A | 11/1989 | Liautaud |
| 4,886,189 A | 12/1989 | Vanderjagt |
| 4,896,832 A | 1/1990 | Howlett |
| 4,908,024 A | 3/1990 | Py |
| 4,912,357 A | 3/1990 | Drews et al. |
| 4,917,274 A | 4/1990 | Asa et al. |
| 4,927,062 A | 5/1990 | Walsh |
| 4,927,115 A | 5/1990 | Bahroos et al. |
| 4,946,452 A | 8/1990 | Py |
| 4,952,212 A | 8/1990 | Booth et al. |
| 4,961,885 A | 10/1990 | Avrahami et al. |
| 4,969,869 A | 11/1990 | Burgin et al. |
| 4,981,479 A | 1/1991 | Py |
| 4,996,502 A | 2/1991 | Endo |
| 5,007,905 A | 4/1991 | Bauer |
| 5,019,037 A | 5/1991 | Wang et al. |
| 5,029,579 A | 7/1991 | Trammell |
| 5,030,214 A | 7/1991 | Spector |
| 5,032,111 A | 7/1991 | Morris et al. |
| 5,037,012 A | 8/1991 | Langford |
| 5,040,706 A | 8/1991 | Davis et al. |
| 5,047,009 A | 9/1991 | Morris et al. |
| 5,048,727 A | 9/1991 | Vlasich |
| 5,053,000 A | 10/1991 | Booth et al. |
| 5,054,477 A | 10/1991 | Terada et al. |
| 5,064,420 A | 11/1991 | Clarke et al. |
| 5,066,276 A | 11/1991 | Wang |
| 5,069,204 A | 12/1991 | Smith et al. |
| 5,069,675 A | 12/1991 | Menchel et al. |
| 5,085,651 A | 2/1992 | Py |
| 5,098,375 A | 3/1992 | Baier |
| 5,133,702 A | 7/1992 | Py |
| 5,134,993 A | 8/1992 | van der Linden et al. |
| 5,139,496 A | 8/1992 | Hed |
| 5,145,113 A | 9/1992 | Burwell et al. |
| 5,152,435 A | 10/1992 | Stand et al. |
| 5,152,456 A | 10/1992 | Ross et al. |
| 5,163,929 A | 11/1992 | Py |
| 5,164,740 A | 11/1992 | Ivri |

(56) References Cited

U.S. PATENT DOCUMENTS

| | | |
|---|---|---|
| 5,170,782 A | 12/1992 | Kocinski |
| 5,171,306 A | 12/1992 | Vo |
| 5,176,856 A | 1/1993 | Takahashi et al. |
| 5,178,856 A | 1/1993 | Burstein |
| 5,193,745 A | 3/1993 | Holm |
| 5,200,248 A | 4/1993 | Thompson et al. |
| 5,201,726 A | 4/1993 | Kirkham |
| 5,203,506 A | 4/1993 | Gross et al. |
| 5,226,538 A | 7/1993 | Roselle |
| 5,247,842 A | 9/1993 | Kaufman et al. |
| 5,252,318 A | 10/1993 | Joshi et al. |
| 5,256,157 A | 10/1993 | Samiotes et al. |
| 5,259,385 A | 11/1993 | Miller et al. |
| 5,261,601 A | 11/1993 | Ross et al. |
| 5,265,288 A | 11/1993 | Allison |
| 5,267,986 A | 12/1993 | Py |
| 5,276,867 A | 1/1994 | Kenley et al. |
| 5,296,673 A | 3/1994 | Smith |
| 5,299,739 A | 4/1994 | Takahashi et al. |
| 5,312,046 A | 5/1994 | Knoch et al. |
| 5,316,159 A | 5/1994 | Douglas et al. |
| 5,318,014 A | 6/1994 | Carter |
| 5,320,845 A | 6/1994 | Py |
| 5,354,032 A | 10/1994 | Sims et al. |
| 5,364,405 A | 11/1994 | Zaleski |
| 5,368,582 A | 11/1994 | Bertera |
| 5,401,259 A | 3/1995 | Py |
| 5,405,614 A | 4/1995 | D'Angelo et al. |
| 5,431,663 A | 7/1995 | Carter |
| 5,435,282 A | 7/1995 | Haber et al. |
| 5,435,465 A | 7/1995 | El-Amin |
| 5,485,828 A | 1/1996 | Hauser |
| 5,496,411 A | 3/1996 | Candy |
| 5,497,944 A | 3/1996 | Weston et al. |
| 5,499,751 A | 3/1996 | Meyer |
| D368,774 S | 4/1996 | Py |
| 5,511,726 A | 4/1996 | Greenspan et al. |
| 5,515,841 A | 5/1996 | Robertson et al. |
| 5,518,179 A | 5/1996 | Humberstone et al. |
| 5,522,385 A | 6/1996 | Lloyd et al. |
| 5,529,055 A | 6/1996 | Gueret |
| 5,551,416 A | 9/1996 | Stimpson et al. |
| D374,719 S | 10/1996 | Py |
| 5,564,016 A | 10/1996 | Korenshtein |
| 5,584,823 A | 12/1996 | Valberg |
| 5,586,550 A | 12/1996 | Ivri et al. |
| 5,588,564 A | 12/1996 | Hutson et al. |
| 5,607,410 A | 3/1997 | Branch |
| 5,613,957 A | 3/1997 | Py |
| 5,614,545 A | 3/1997 | Martin et al. |
| 5,630,793 A | 5/1997 | Rowe |
| 5,657,926 A | 8/1997 | Toda |
| 5,665,079 A | 9/1997 | Stahl |
| 5,685,869 A | 11/1997 | Py |
| 5,687,874 A | 11/1997 | Omori et al. |
| 5,688,232 A | 11/1997 | Flower |
| 5,693,016 A | 12/1997 | Gumaste et al. |
| 5,707,636 A | 1/1998 | Rodriguez et al. |
| 5,724,021 A | 3/1998 | Perrone |
| 5,730,723 A | 3/1998 | Castellano et al. |
| 5,735,811 A | 4/1998 | Brisken |
| 5,740,947 A | 4/1998 | Flaig et al. |
| 5,746,728 A | 5/1998 | Py |
| 5,758,637 A | 6/1998 | Ivri et al. |
| 5,803,106 A | 9/1998 | Cohen et al. |
| 5,807,357 A | 9/1998 | Kang |
| 5,823,428 A | 10/1998 | Humberstone et al. |
| 5,838,350 A | 11/1998 | Newcombe et al. |
| 5,843,109 A | 12/1998 | Mehta et al. |
| 5,855,322 A | 1/1999 | Py |
| 5,855,564 A | 1/1999 | Ruskewicz |
| 5,881,716 A | 3/1999 | Wirch et al. |
| 5,881,956 A * | 3/1999 | Cohen ............... B05B 11/0062 222/321.7 |
| 5,893,515 A | 4/1999 | Hahn et al. |
| 5,894,841 A | 4/1999 | Voges |
| 5,938,117 A | 8/1999 | Ivri |
| 5,938,637 A | 8/1999 | Austin et al. |
| D413,668 S | 9/1999 | Mannberg et al. |
| 5,957,943 A | 9/1999 | Vaitekunas |
| 5,970,974 A | 10/1999 | Van Der Linden et al. |
| 5,996,903 A | 12/1999 | Asai et al. |
| 5,997,518 A | 12/1999 | Laibovitz et al. |
| 6,000,394 A | 12/1999 | Blaha-Schnabel et al. |
| 6,008,468 A | 12/1999 | Tanaka et al. |
| 6,011,062 A | 1/2000 | Schneider et al. |
| 6,014,970 A | 1/2000 | Ivri et al. |
| 6,027,450 A | 2/2000 | Brown et al. |
| 6,039,565 A | 3/2000 | Chou et al. |
| 6,062,212 A | 5/2000 | Davison et al. |
| 6,083,922 A | 7/2000 | Montgomery |
| 6,085,740 A | 7/2000 | Ivri et al. |
| 6,116,893 A | 9/2000 | Peach |
| 6,135,427 A | 10/2000 | Tsai |
| 6,152,383 A | 11/2000 | Chen |
| 6,158,431 A | 12/2000 | Poole |
| 6,159,188 A | 12/2000 | Laibovitz et al. |
| 6,171,276 B1 | 1/2001 | Lippe et al. |
| 6,193,683 B1 | 2/2001 | Ludin et al. |
| 6,196,219 B1 | 3/2001 | Hess et al. |
| 6,203,759 B1 | 3/2001 | Pelc et al. |
| 6,205,999 B1 | 3/2001 | Ivri et al. |
| 6,216,966 B1 | 4/2001 | Prendergast et al. |
| 6,221,038 B1 | 4/2001 | Brisken |
| 6,228,046 B1 | 5/2001 | Brisken |
| 6,235,024 B1 | 5/2001 | Tu |
| 6,235,177 B1 | 5/2001 | Borland et al. |
| 6,251,952 B1 | 6/2001 | Siff |
| 6,254,579 B1 | 7/2001 | Cogger et al. |
| 6,254,587 B1 | 7/2001 | Christ et al. |
| 6,263,872 B1 | 7/2001 | Schuster et al. |
| 6,273,342 B1 | 8/2001 | Terada et al. |
| 6,296,626 B1 | 10/2001 | Stein |
| 6,297,289 B2 | 10/2001 | Siff |
| 6,318,361 B1 | 11/2001 | Sosiak |
| 6,336,917 B1 | 1/2002 | Berke |
| 6,341,732 B1 | 1/2002 | Martin et al. |
| 6,357,442 B1 | 3/2002 | Casper et al. |
| 6,357,671 B1 | 3/2002 | Cewers |
| 6,367,685 B1 | 4/2002 | Jiang et al. |
| 6,394,363 B1 | 5/2002 | Arnott et al. |
| 6,397,838 B1 | 6/2002 | Zimlich, Jr. et al. |
| 6,398,737 B2 | 6/2002 | Moore et al. |
| 6,398,766 B1 | 6/2002 | Branch |
| 6,422,431 B2 | 7/2002 | Pelc et al. |
| 6,423,040 B1 | 7/2002 | Benktzon et al. |
| 6,425,888 B1 | 7/2002 | Embleton et al. |
| 6,427,682 B1 | 8/2002 | Klimowicz et al. |
| 6,435,175 B1 | 8/2002 | Stenzler |
| 6,442,423 B1 | 8/2002 | Domb et al. |
| 6,443,146 B1 | 9/2002 | Voges |
| 6,467,476 B1 | 10/2002 | Ivri et al. |
| 6,513,682 B1 | 2/2003 | Cohen et al. |
| 6,524,287 B1 | 2/2003 | Cogger |
| 6,526,976 B1 | 3/2003 | Baran |
| 6,530,370 B1 | 3/2003 | Heinonen |
| 6,537,817 B1 | 3/2003 | Papen |
| RE38,077 E | 4/2003 | Cohen et al. |
| 6,540,153 B1 | 4/2003 | Ivri |
| 6,540,154 B1 | 4/2003 | Ivri et al. |
| 6,543,443 B1 | 4/2003 | Klimowicz et al. |
| 6,546,927 B2 | 4/2003 | Litherland et al. |
| 6,547,755 B1 | 4/2003 | Lippe et al. |
| 6,547,770 B2 | 4/2003 | Carlsson et al. |
| 6,550,472 B2 | 4/2003 | Litherland et al. |
| 6,554,201 B2 | 4/2003 | Klimowicz et al. |
| 6,554,801 B1 | 4/2003 | Steward et al. |
| 6,569,131 B1 | 5/2003 | Michael et al. |
| 6,569,387 B1 | 5/2003 | Furner et al. |
| 6,601,581 B1 | 8/2003 | Babaev |
| 6,610,033 B1 | 8/2003 | Melanson et al. |
| 6,610,036 B2 | 8/2003 | Branch et al. |
| 6,612,302 B1 | 9/2003 | Rand |
| 6,615,824 B2 | 9/2003 | Power |

(56) References Cited

U.S. PATENT DOCUMENTS

| | | |
|---|---|---|
| 6,619,562 B2 | 9/2003 | Hamaguchi et al. |
| 6,622,720 B2 | 9/2003 | Hadimioglu |
| 6,629,646 B1 | 10/2003 | Ivri |
| 6,640,804 B2 | 11/2003 | Ivri et al. |
| 6,650,935 B1 | 11/2003 | Watmough |
| 6,651,650 B1 | 11/2003 | Yamamoto et al. |
| 6,651,844 B2 | 11/2003 | Tomaka et al. |
| 6,659,364 B1 | 12/2003 | Humberstone et al. |
| 6,660,249 B2 | 12/2003 | Montgomery |
| 6,669,961 B2 | 12/2003 | Kim et al. |
| 6,676,034 B2 | 1/2004 | Tanaka et al. |
| 6,679,436 B1 | 1/2004 | Onishi et al. |
| 6,684,681 B1 | 2/2004 | Zombo |
| 6,684,879 B1 | 2/2004 | Coffee et al. |
| 6,719,770 B2 | 4/2004 | Laufer et al. |
| 6,732,944 B2 | 5/2004 | Litherland et al. |
| 6,736,904 B2 | 5/2004 | Poniatowski et al. |
| 6,740,107 B2 | 5/2004 | Loeb et al. |
| 6,748,944 B1 | 6/2004 | DellaVecchia et al. |
| 6,761,286 B2 | 7/2004 | Py et al. |
| 6,776,309 B2 | 8/2004 | Schultz |
| 6,782,886 B2 | 8/2004 | Narayan et al. |
| 6,789,741 B2 | 9/2004 | Varanasi et al. |
| 6,814,071 B2 | 11/2004 | Klimowicz et al. |
| 6,830,046 B2 | 12/2004 | Blakley et al. |
| 6,845,770 B2 | 1/2005 | Klimowicz et al. |
| 6,851,626 B2 | 2/2005 | Patel et al. |
| 6,854,461 B2 | 2/2005 | Nichols et al. |
| 6,854,662 B2 | 2/2005 | Chen |
| 6,863,224 B2 | 3/2005 | Terada et al. |
| 6,877,642 B1 | 4/2005 | Maddox et al. |
| 6,885,818 B2 | 4/2005 | Goldstein |
| 6,886,556 B2 | 5/2005 | Fuchs |
| 6,889,690 B2 | 5/2005 | Crowder et al. |
| 6,901,926 B2 | 6/2005 | Yamamoto et al. |
| 6,913,205 B2 | 7/2005 | Cornet et al. |
| 6,915,962 B2 | 7/2005 | Power et al. |
| 6,921,020 B2 | 7/2005 | Ivri |
| 6,926,208 B2 | 8/2005 | Ivri |
| 6,946,117 B1 | 9/2005 | Schutt et al. |
| 6,948,491 B2 | 9/2005 | Loeffler et al. |
| 6,964,647 B1 | 11/2005 | Babaev |
| 6,968,840 B2 | 11/2005 | Smith et al. |
| 6,969,165 B2 | 11/2005 | Olsen |
| 6,971,383 B2 | 12/2005 | Hickey et al. |
| 6,974,450 B2 | 12/2005 | Weber et al. |
| 6,976,279 B1 | 12/2005 | Berke et al. |
| 6,976,969 B2 | 12/2005 | Messerly |
| 6,978,941 B2 | 12/2005 | Litherland et al. |
| 6,978,945 B2 | 12/2005 | Wong et al. |
| 6,991,137 B2 | 1/2006 | Schultz |
| 7,014,068 B1 | 3/2006 | Cohen et al. |
| 7,017,573 B1 | 3/2006 | Rasor et al. |
| 7,032,590 B2 | 4/2006 | Loeffler et al. |
| 7,040,549 B2 | 5/2006 | Ivri et al. |
| 7,066,398 B2 | 6/2006 | Borland et al. |
| 7,070,071 B2 | 7/2006 | Pavlu et al. |
| 7,073,733 B2 | 7/2006 | Cohen et al. |
| 7,081,757 B2 | 7/2006 | Unsworth et al. |
| 7,083,112 B2 | 8/2006 | Ivri |
| 7,100,600 B2 | 9/2006 | Loeffler et al. |
| 7,104,463 B2 | 9/2006 | Litherland et al. |
| 7,108,197 B2 | 9/2006 | Ivri |
| 7,121,275 B2 | 10/2006 | Noolandi et al. |
| D533,658 S | 12/2006 | Collins, Jr. et al. |
| 7,153,315 B2 | 12/2006 | Miller |
| 7,161,269 B2 | 1/2007 | Kayama et al. |
| 7,168,633 B2 | 1/2007 | Wang et al. |
| D537,160 S | 2/2007 | Lowell |
| 7,174,888 B2 | 2/2007 | Ivri et al. |
| 7,192,129 B2 | 3/2007 | Droege et al. |
| 7,195,011 B2 | 3/2007 | Loeffler et al. |
| 7,201,167 B2 | 4/2007 | Fink et al. |
| 7,201,732 B2 | 4/2007 | Anderson et al. |
| 7,204,820 B2 | 4/2007 | Akahoshi |
| 7,229,028 B2 | 6/2007 | Chen et al. |
| 7,234,460 B2 | 6/2007 | Greenleaf et al. |
| 7,261,224 B2 | 8/2007 | Cohen et al. |
| 7,267,121 B2 | 9/2007 | Ivri |
| 7,290,541 B2 | 11/2007 | Ivri et al. |
| 7,314,187 B2 | 1/2008 | Hochrainer et al. |
| 7,316,067 B2 | 1/2008 | Blakey |
| 7,322,349 B2 | 1/2008 | Power |
| 7,331,339 B2 | 2/2008 | Smith et al. |
| 7,357,133 B2 | 4/2008 | Goodchild |
| 7,360,536 B2 | 4/2008 | Patel et al. |
| 7,442,180 B2 | 10/2008 | Vitello et al. |
| 7,448,559 B2 | 11/2008 | Le Maner et al. |
| 7,455,393 B2 | 11/2008 | Onozawa |
| 7,469,874 B2 | 12/2008 | Akahori |
| 7,472,701 B2 | 1/2009 | Pfichner et al. |
| 7,524,006 B2 | 4/2009 | Shin et al. |
| D597,206 S | 7/2009 | Collins, Jr. et al. |
| 7,574,787 B2 | 8/2009 | Xu et al. |
| 7,600,511 B2 | 10/2009 | Power et al. |
| 7,628,339 B2 | 12/2009 | Ivri et al. |
| 7,651,011 B2 | 1/2010 | Cohen et al. |
| 7,677,467 B2 | 3/2010 | Fink et al. |
| 7,678,089 B2 | 3/2010 | Py et al. |
| 7,712,466 B2 | 5/2010 | Addington et al. |
| 7,752,058 B2 | 7/2010 | Sasaki et al. |
| 7,819,115 B2 | 10/2010 | Sexton et al. |
| 7,849,851 B2 | 12/2010 | Zierenberg et al. |
| 7,856,975 B2 | 12/2010 | Nobutani et al. |
| 7,883,031 B2 | 2/2011 | Collins, Jr. et al. |
| 7,891,580 B2 | 2/2011 | Valpey, III et al. |
| 7,900,850 B2 | 3/2011 | Zengerle et al. |
| 7,946,291 B2 | 5/2011 | Fink et al. |
| 7,954,486 B2 | 6/2011 | Papania et al. |
| 7,954,730 B2 | 6/2011 | Ng |
| 7,971,588 B2 | 7/2011 | Fink et al. |
| 7,981,097 B2 | 7/2011 | Paoli, Jr. |
| 8,012,136 B2 | 9/2011 | Collins, Jr. et al. |
| 8,128,606 B2 | 3/2012 | Anderson et al. |
| 8,163,257 B2 | 4/2012 | Wallace et al. |
| 8,205,971 B2 | 6/2012 | Newton et al. |
| 8,246,589 B2 | 8/2012 | Marx |
| 8,267,285 B2 | 9/2012 | Cohen et al. |
| 8,342,368 B2 | 1/2013 | Ophardt et al. |
| 8,348,177 B2 | 1/2013 | Loverich et al. |
| 8,376,525 B2 | 2/2013 | Asai et al. |
| 8,387,834 B2 | 3/2013 | Proper et al. |
| 8,430,338 B2 * | 4/2013 | Duru .................. B05B 17/0669 239/338 |
| 8,485,503 B2 | 7/2013 | Lei |
| 8,545,463 B2 | 10/2013 | Collins, Jr. et al. |
| 8,556,132 B2 | 10/2013 | Cohen et al. |
| 8,561,604 B2 | 10/2013 | Ivri et al. |
| 8,578,931 B2 | 11/2013 | Ivri et al. |
| 8,616,195 B2 | 12/2013 | Power et al. |
| 8,684,980 B2 | 4/2014 | Hunter et al. |
| D705,924 S | 5/2014 | Hunter et al. |
| 8,733,935 B2 | 5/2014 | Ballou, Jr. et al. |
| 8,734,408 B2 | 5/2014 | Marx |
| 8,936,021 B2 | 1/2015 | Collins, Jr. |
| 8,950,394 B2 | 2/2015 | Patton et al. |
| 9,004,061 B2 | 4/2015 | Patton et al. |
| 9,022,970 B2 | 5/2015 | Dacquay et al. |
| 9,039,666 B2 | 5/2015 | Voss et al. |
| 9,050,424 B2 | 6/2015 | Van Der Mark |
| 9,068,566 B2 | 6/2015 | Ivri |
| 9,087,145 B2 | 7/2015 | Ballou, Jr. et al. |
| 9,108,211 B2 | 8/2015 | Ivri |
| 9,180,261 B2 | 11/2015 | Patton et al. |
| 9,186,690 B2 | 11/2015 | Scanlon et al. |
| 9,279,177 B2 | 3/2016 | Choi et al. |
| 9,333,523 B2 | 5/2016 | Lowy |
| 9,421,199 B2 | 8/2016 | Ostrow et al. |
| 9,463,486 B2 | 10/2016 | Wilkerson et al. |
| 9,545,488 B2 | 1/2017 | Patton et al. |
| 9,610,192 B2 | 4/2017 | Marx |
| 9,623,174 B2 | 4/2017 | Pang et al. |
| 9,801,757 B2 | 10/2017 | Voss et al. |
| 10,251,875 B2 | 4/2019 | Puri et al. |

(56) References Cited

U.S. PATENT DOCUMENTS

| | | |
|---|---|---|
| 10,265,216 B2 | 4/2019 | Nielsen |
| 10,583,038 B2 | 3/2020 | Ivri |
| 10,583,132 B2 | 3/2020 | Puri et al. |
| 10,624,781 B2 | 4/2020 | Ivri |
| 10,639,194 B2 | 5/2020 | Hunter et al. |
| 10,646,373 B2 | 5/2020 | Hunter et al. |
| 10,751,214 B2 | 8/2020 | Kelly |
| 10,842,787 B2 | 11/2020 | Ostrow et al. |
| 10,888,454 B2 | 1/2021 | Ivri et al. |
| 10,888,557 B2 | 1/2021 | Ostrow et al. |
| 10,940,145 B2 | 3/2021 | Ostrow et al. |
| 10,953,002 B2 | 3/2021 | Ostrow et al. |
| 2001/0025190 A1 | 9/2001 | Weber et al. |
| 2001/0049608 A1 | 12/2001 | Hochman |
| 2001/0056258 A1 | 12/2001 | Evans |
| 2002/0016576 A1 | 2/2002 | Lee |
| 2002/0039502 A1 | 4/2002 | Matsumoto et al. |
| 2002/0043262 A1 | 4/2002 | Langford et al. |
| 2002/0074362 A1 | 6/2002 | Py et al. |
| 2002/0085067 A1 | 7/2002 | Palifka et al. |
| 2002/0104530 A1 | 8/2002 | Ivri et al. |
| 2002/0121285 A1 | 9/2002 | Poniatowski et al. |
| 2002/0124843 A1 | 9/2002 | Skiba et al. |
| 2002/0158196 A1 | 10/2002 | Berggren et al. |
| 2002/0161344 A1 | 10/2002 | Peclat et al. |
| 2003/0024526 A1 | 2/2003 | Ganan-Calvo |
| 2003/0032930 A1 | 2/2003 | Branch |
| 2003/0078551 A1 | 4/2003 | Hochrainer et al. |
| 2003/0114901 A1 | 6/2003 | Loeb et al. |
| 2003/0144594 A1 | 7/2003 | Gellman |
| 2003/0185892 A1 | 10/2003 | Bell et al. |
| 2003/0192532 A1 | 10/2003 | Hopkins |
| 2004/0010239 A1 | 1/2004 | Hochrainer et al. |
| 2004/0039355 A1 | 2/2004 | Gonzalez et al. |
| 2004/0045547 A1 | 3/2004 | Yamamoto et al. |
| 2004/0050953 A1 | 3/2004 | Terada et al. |
| 2004/0055595 A1 | 3/2004 | Noymer et al. |
| 2004/0082884 A1 | 4/2004 | Pal et al. |
| 2004/0092548 A1 | 5/2004 | Embleton et al. |
| 2004/0116524 A1 | 6/2004 | Cohen et al. |
| 2004/0164099 A1 | 8/2004 | Diestelhorst et al. |
| 2004/0176757 A1 | 9/2004 | Sinelnikov et al. |
| 2004/0186384 A1 | 9/2004 | Babaev |
| 2004/0204674 A1 | 10/2004 | Anderson et al. |
| 2004/0215157 A1 | 10/2004 | Peclat et al. |
| 2004/0220537 A1 | 11/2004 | Embleton et al. |
| 2004/0256487 A1 | 12/2004 | Collins et al. |
| 2005/0029307 A1 | 2/2005 | Py et al. |
| 2005/0077392 A1 | 4/2005 | Geser et al. |
| 2005/0089545 A1 | 4/2005 | Kuwano et al. |
| 2005/0195598 A1 | 9/2005 | Dancs et al. |
| 2005/0205089 A1 | 9/2005 | Fink et al. |
| 2005/0240162 A1 | 10/2005 | Chen et al. |
| 2005/0244339 A1 | 11/2005 | Jauernig et al. |
| 2005/0260203 A1 | 11/2005 | Wiegand et al. |
| 2005/0261641 A1 | 11/2005 | Warchol et al. |
| 2005/0263149 A1 | 12/2005 | Noymer et al. |
| 2005/0275310 A1 | 12/2005 | Ripoll |
| 2005/0279305 A1 | 12/2005 | Rasor et al. |
| 2006/0024374 A1 | 2/2006 | Gasco et al. |
| 2006/0028420 A1 | 2/2006 | Nagata et al. |
| 2006/0039715 A1 | 2/2006 | Rimai et al. |
| 2006/0041248 A1 | 2/2006 | Patton et al. |
| 2006/0057216 A1 | 3/2006 | Salamone et al. |
| 2006/0174869 A1 | 8/2006 | Gumaste et al. |
| 2006/0196518 A1 | 9/2006 | Hon |
| 2006/0201501 A1 | 9/2006 | Morrison et al. |
| 2006/0209129 A1 | 9/2006 | Onozawa |
| 2006/0213503 A1 | 9/2006 | Borgschulte et al. |
| 2006/0219806 A1 | 10/2006 | Wang et al. |
| 2006/0243820 A1 | 11/2006 | Ng |
| 2006/0258993 A1 | 11/2006 | Hochrainer et al. |
| 2007/0023547 A1 | 2/2007 | Borland et al. |
| 2007/0044792 A1 | 3/2007 | Ivri |
| 2007/0113841 A1 | 5/2007 | Fuchs |
| 2007/0119969 A1 | 5/2007 | Collins et al. |
| 2007/0211212 A1 | 9/2007 | Bennwik |
| 2007/0248645 A1 | 10/2007 | Bague et al. |
| 2007/0270768 A1 | 11/2007 | Dacquay et al. |
| 2008/0017189 A1 | 1/2008 | Ruckdeschel et al. |
| 2008/0043061 A1 | 2/2008 | Glezer et al. |
| 2008/0142624 A1 | 6/2008 | Ivri et al. |
| 2008/0164339 A1 | 7/2008 | Duru |
| 2008/0208627 A1 | 8/2008 | Skyggebjerg |
| 2008/0233053 A1 | 9/2008 | Gross et al. |
| 2008/0299049 A1 | 12/2008 | Stangl |
| 2008/0303850 A1 | 12/2008 | Shin et al. |
| 2008/0308096 A1 | 12/2008 | Borgschulte et al. |
| 2009/0025713 A1 | 1/2009 | Keller et al. |
| 2009/0044397 A1 | 2/2009 | Cohen et al. |
| 2009/0108094 A1 | 4/2009 | Ivri |
| 2009/0114218 A1 | 5/2009 | Veatch |
| 2009/0114742 A1 | 5/2009 | Collins, Jr. |
| 2009/0118243 A1 | 5/2009 | Gjorstrup |
| 2009/0149829 A1 | 6/2009 | Collins, Jr. |
| 2009/0167812 A1 | 7/2009 | Asai et al. |
| 2009/0192443 A1 | 7/2009 | Collins, Jr. |
| 2009/0212133 A1 | 8/2009 | Collins, Jr. |
| 2009/0223513 A1 | 9/2009 | Papania et al. |
| 2009/0272818 A1 | 11/2009 | Valpey, III et al. |
| 2009/0312724 A1 | 12/2009 | Pipkin et al. |
| 2010/0044460 A1 | 2/2010 | Sauzade |
| 2010/0076388 A1 | 3/2010 | Cater |
| 2010/0083956 A1 | 4/2010 | Fukumoto et al. |
| 2010/0111843 A1 | 5/2010 | Boyden et al. |
| 2010/0126502 A1 | 5/2010 | Fink et al. |
| 2010/0144539 A1 | 6/2010 | Bergh et al. |
| 2010/0211408 A1 | 8/2010 | Park et al. |
| 2010/0222752 A1 | 9/2010 | Collins, Jr. et al. |
| 2010/0280466 A1 | 11/2010 | Py et al. |
| 2010/0283601 A1 | 11/2010 | Tai et al. |
| 2011/0092925 A1 | 4/2011 | Voss et al. |
| 2011/0233302 A1 | 9/2011 | Lin et al. |
| 2012/0062840 A1 | 3/2012 | Ballou, Jr. et al. |
| 2012/0070467 A1 | 3/2012 | Ballou, Jr. et al. |
| 2012/0143152 A1* | 6/2012 | Hunter ............... B05B 17/0676 604/290 |
| 2012/0318260 A1 | 12/2012 | Hsieh et al. |
| 2013/0085459 A1 | 4/2013 | Voss et al. |
| 2013/0150812 A1 | 6/2013 | Hunter et al. |
| 2013/0172830 A1 | 7/2013 | Hunter et al. |
| 2013/0206857 A1 | 8/2013 | Ivri |
| 2013/0242255 A1 | 9/2013 | Caldarise et al. |
| 2013/0299607 A1 | 11/2013 | Wilkerson et al. |
| 2013/0334335 A1 | 12/2013 | Wilkerson et al. |
| 2014/0151405 A1 | 6/2014 | Kelly |
| 2014/0151457 A1 | 6/2014 | Wilkerson et al. |
| 2014/0171490 A1 | 6/2014 | Gross et al. |
| 2014/0187969 A1 | 7/2014 | Hunter et al. |
| 2014/0249491 A1 | 9/2014 | Ballou, Jr. et al. |
| 2014/0336618 A1 | 11/2014 | Wilkerson et al. |
| 2014/0361095 A1 | 12/2014 | Haran |
| 2015/0034075 A1 | 2/2015 | Gallem et al. |
| 2015/0328151 A1 | 11/2015 | Ballou, Jr. et al. |
| 2015/0340590 A1 | 11/2015 | Ivri |
| 2016/0129088 A1 | 5/2016 | Patton et al. |
| 2016/0250437 A1 | 9/2016 | Fink et al. |
| 2016/0263314 A1* | 9/2016 | Pardes ............... B05B 11/1032 |
| 2016/0271346 A1 | 9/2016 | Patton et al. |
| 2016/0361494 A1 | 12/2016 | Jürg et al. |
| 2017/0136484 A1* | 5/2017 | Wilkerson ............. A61M 11/00 |
| 2017/0151088 A1 | 6/2017 | Ballou, Jr. et al. |
| 2017/0156927 A1 | 6/2017 | Richter et al. |
| 2017/0182510 A1 | 6/2017 | Wilkerson et al. |
| 2017/0211959 A1 | 7/2017 | Adler et al. |
| 2017/0344714 A1 | 11/2017 | Ballou, Jr. et al. |
| 2017/0367882 A1 | 12/2017 | Kelly |
| 2018/0021530 A1 | 1/2018 | Fink et al. |
| 2018/0147214 A1 | 5/2018 | Ostrow et al. |
| 2019/0053945 A1 | 2/2019 | Hunter et al. |
| 2019/0192499 A1 | 6/2019 | Puri et al. |
| 2019/0314195 A1 | 10/2019 | Ivri et al. |
| 2020/0019721 A1 | 1/2020 | Shanmugam et al. |
| 2020/0085813 A1 | 3/2020 | Ostrow et al. |

(56) References Cited

U.S. PATENT DOCUMENTS

| | | |
|---|---|---|
| 2020/0094285 A1 | 3/2020 | Wilkerson et al. |
| 2020/0197218 A1 | 6/2020 | Newell et al. |
| 2020/0197220 A1 | 6/2020 | Ivri |
| 2020/0306239 A1 | 10/2020 | Ostrow et al. |
| 2020/0315842 A1 | 10/2020 | Palanker et al. |
| 2020/0315955 A1 | 10/2020 | Soppimath et al. |
| 2020/0330267 A1* | 10/2020 | Li .................... A61M 35/00 |
| 2020/0337896 A1 | 10/2020 | Ianchulev et al. |
| 2020/0338060 A1 | 10/2020 | Ostrow et al. |
| 2020/0345542 A1 | 11/2020 | Ostrow et al. |
| 2020/0352928 A1 | 11/2020 | Puri et al. |
| 2020/0397775 A1 | 12/2020 | Mohammed et al. |
| 2020/0397776 A1 | 12/2020 | Mohammed et al. |
| 2020/0405705 A1 | 12/2020 | Mohammed et al. |
| 2021/0121395 A1 | 4/2021 | Soppimath et al. |
| 2021/0128350 A1* | 5/2021 | Ivri .................... A61F 9/0008 |
| 2021/0128546 A1 | 5/2021 | Soppimath et al. |
| 2021/0137732 A1* | 5/2021 | Quintana ............. A61J 1/1443 |
| 2021/0177650 A1 | 6/2021 | Clauson et al. |
| 2021/0295989 A1 | 9/2021 | Ballou, Jr. et al. |
| 2023/0239968 A1* | 7/2023 | Batista ............. A61M 15/0041 |
| | | 392/403 |

FOREIGN PATENT DOCUMENTS

| | | |
|---|---|---|
| DE | 19616300 A1 | 10/1997 |
| DE | 199 34 582 C2 | 9/2003 |
| DE | 102 36 669 A1 | 2/2004 |
| EP | 0 011 269 B1 | 4/1983 |
| EP | 0 150 571 A1 | 8/1985 |
| EP | 0 224 352 B1 | 8/1990 |
| EP | 0 389 665 A1 | 10/1990 |
| EP | 0 590 165 B1 | 2/1997 |
| EP | 0 933 138 B1 | 3/2004 |
| EP | 1 219 314 B1 | 3/2004 |
| EP | 0 823 246 B1 | 4/2004 |
| EP | 1 493 410 A2 | 1/2005 |
| FR | 1 271 341 A | 9/1961 |
| FR | 2 934 128 A1 | 1/2010 |
| GB | 558866 A | 1/1944 |
| GB | 1 569 707 A | 6/1980 |
| GB | 2 272 389 A | 5/1994 |
| JP | S62-142110 A | 6/1987 |
| JP | H06-29539 U | 4/1994 |
| JP | H8-52193 A | 2/1996 |
| JP | H08-503164 A | 4/1996 |
| JP | 2000-043243 A | 2/2000 |
| JP | 2002-191560 A | 7/2002 |
| JP | 2003-501157 A | 1/2003 |
| JP | 3104861 U | 10/2004 |
| JP | 2005-515841 A | 6/2005 |
| JP | 2005-288009 A | 10/2005 |
| JP | 2008-515625 A | 5/2008 |
| JP | 2009-072313 A | 4/2009 |
| JP | 2012-508129 A | 4/2012 |
| JP | 2013-523283 A | 6/2013 |
| JP | 2017-533798 A | 11/2017 |
| JP | 2019-069086 A | 5/2019 |
| KR | 10-2015-0020542 A | 2/2015 |
| TW | I293898 B | 3/2008 |
| WO | WO-85/00761 A1 | 2/1985 |
| WO | WO-91/12687 A1 | 8/1991 |
| WO | WO-91/14468 A1 | 10/1991 |
| WO | WO-94/11111 A1 | 5/1994 |
| WO | WO-94/13305 A1 | 6/1994 |
| WO | WO-94/23788 A1 | 10/1994 |
| WO | WO-95/15822 A1 | 6/1995 |
| WO | WO-95/26236 A1 | 10/1995 |
| WO | WO-96/00050 A1 | 1/1996 |
| WO | WO-96/06581 A1 | 3/1996 |
| WO | WO-97/05960 A1 | 2/1997 |
| WO | WO-97/12687 A1 | 4/1997 |
| WO | WO-97/23177 A1 | 7/1997 |
| WO | WO-98/08479 A1 | 3/1998 |
| WO | WO-98/19383 A1 | 5/1998 |
| WO | WO-99/17888 A1 | 4/1999 |
| WO | WO-00/18455 A1 | 4/2000 |
| WO | WO-00/66277 A1 | 11/2000 |
| WO | WO-01/03645 A2 | 1/2001 |
| WO | WO-01/19437 A1 | 3/2001 |
| WO | WO-01/58236 A2 | 8/2001 |
| WO | WO-01/68169 A1 | 9/2001 |
| WO | WO-01/85245 A1 | 11/2001 |
| WO | WO-02/28545 A1 | 4/2002 |
| WO | WO-02/055131 A2 | 7/2002 |
| WO | WO-02/062488 A1 | 8/2002 |
| WO | WO-02/072169 A2 | 9/2002 |
| WO | WO-03/002045 A1 | 1/2003 |
| WO | WO-03/002265 A1 | 1/2003 |
| WO | WO-03/026556 A2 | 4/2003 |
| WO | WO-03/097139 A1 | 11/2003 |
| WO | WO-2004/028420 A1 | 4/2004 |
| WO | WO-2004/050065 A1 | 6/2004 |
| WO | WO-2004/080367 A2 | 9/2004 |
| WO | WO-2004/084116 A1 | 9/2004 |
| WO | WO-2004/103478 A1 | 12/2004 |
| WO | WO-2004/105864 A1 | 12/2004 |
| WO | WO-2005/102058 A2 | 11/2005 |
| WO | WO-2006/006963 A2 | 1/2006 |
| WO | WO-2006/050838 A2 | 5/2006 |
| WO | WO-2006/082588 A2 | 8/2006 |
| WO | WO-2007/056233 A1 | 5/2007 |
| WO | WO-2007/115087 A1 | 10/2007 |
| WO | WO-2008/015394 A1 | 2/2008 |
| WO | WO-2008/087250 A1 | 7/2008 |
| WO | WO-2008/125128 A1 | 10/2008 |
| WO | WO-2009/055733 A1 | 4/2009 |
| WO | WO-2009/148345 A2 | 12/2009 |
| WO | WO-2011/117212 A1 | 9/2011 |
| WO | WO-2011/123722 A1 | 10/2011 |
| WO | WO-2012/009696 A2 | 1/2012 |
| WO | WO-2012/009702 A1 | 1/2012 |
| WO | WO-2012/009706 A1 | 1/2012 |
| WO | WO-2013/158967 A2 | 10/2013 |
| WO | WO-2015/123656 A1 | 8/2015 |
| WO | WO-2016/115050 A1 | 7/2016 |
| WO | WO-2016/164830 A1 | 10/2016 |
| WO | WO-2018/136618 A2 | 7/2018 |
| WO | WO-2019/104191 A1 | 5/2019 |
| WO | WO-2019/113483 A1 | 6/2019 |
| WO | WO-2020/010116 A1 | 1/2020 |
| WO | PCT/US2020/020656 | 3/2020 |
| WO | WO-2020/180793 A1 | 9/2020 |
| WO | PCT/US2020/064648 | 12/2020 |

OTHER PUBLICATIONS

Ratanapakorn, T. et al. (2006). "Single dose of 1% tropicamide and 10% phenylephrine for pupil dilation." Journal of the Medical Association of Thailand, 89(11), 1934-1939.
U.S. Appl. No. 16/621,564, filed Dec. 11, 2019, US 2020-0197218.
U.S. Appl. No. 16/962,608, filed Jul. 16, 2020, US 2020-0337896.
U.S. Appl. No. 17/091,607, filed Nov. 6, 2020, US 2021-0295989.
U.S. Appl. No. 17/239,832, filed Apr. 26, 2021, US 2021-0398651.
U.S. Appl. No. 17/319,401, filed May 13, 2021, US 2021-0407663.
U.S. Appl. No. 17/397,874, filed Aug. 9, 2021, US 2022-0062035.
U.S. Appl. No. 17/434,711, filed Aug. 27, 2021, US 2022-0125631.
U.S. Appl. No. 13/882,962, filed May 1, 2013, US 2014-0336618.
U.S. Appl. No. 15/197,033, filed Jun. 29, 2016, US 2017-0136484.
U.S. Appl. No. 15/370,196, filed Dec. 6, 2016, US 2017-0151088.
U.S. Appl. No. 16/107,716, filed Aug. 21, 2018, US 2019-0053945.
U.S. Appl. No. 16/434,428, filed Jun. 7, 2019, US 2020-0094285.
U.S. Appl. No. 17/704,395, filed Mar. 25, 2022, US 2022-0355329.
U.S. Appl. No. 17/849,425, filed Jun. 24, 2022, US 2022-0395221.
U.S. Appl. No. 17/994,693, filed Nov. 28, 2022, US 2023-0173118.
"Alcon. RTM: Sharing One Vision," 2009 Annual Report, 46 pages. (2009).
Conover (Ed.), "View into the Future of Ophthalmology Treatments," Healthcare Observer, 1(8):2-37. (2009).
Dhand, "Nebulizers That Use a Vibrating Mesh or Plate with Multiple Apertures to Generate Aerosol," Respir Care, 47(12):1406-1418. (2002).

(56) References Cited

OTHER PUBLICATIONS

Donnelly et al., "Using ultrasonic atomization to produce an aerosol of micron-scale particles," Review of Scientific Instruments, 76:113301-1-113301-10 (2005).

Durnan et al., "Gold-Chlorine and Gold-Bromine Equilibria in Fused Salts," The Journal of Physical Chemistry, 68(4):847-850. (1964).

Galambos et al., "Drop ejection utilizing sideways actuation of a MEMS piston," Sensors and Actuators A, 141:182-191. (2008).

Hinds. "Aerosol Technology: Properies, Behavior, and Measurement of Airborne Particles," pp. 42-71, 111-119, & 294-301. (1999).

Instruction Manual for Omron. RTM. Model NE-U03V MicroAir. RTM. Nebulizer, 20 pages, (No date).

International Search Report mailed Dec. 12, 2011, in International Application No. PCT/US2011/044291. 5 pages.

International Search Report mailed Dec. 13, 2011, in International Application No. PCT/US2011/044286. 6 pages.

Product Description for Xalatan.RTM. latanoprost opthalmic solution, Pfizer Manufacturing, Belgium, NV, 8 pages. (2009).

Quigley. "Improving Eye Drop Treatment for Glaucoma through Better Adherence," Optometry and Vision Science, 85(6):374-375, (2008).

Ranade et al. "Chapter seven: Intranasal and ocular drug delivery," Drug Delivery Systems: Second Edition, CLC Press, 39 pages (2004).

Rosen et al. "Printing High Viscosity Fluids Using Ultrasonic Droplet Generation," The George W. Woodruff School of Mechanical Engineering, Georgia Institute of Technology, pp. 239-253, (2008).

Shidhaye et al. "Novel drug delivery devices," Pharma Times, 38(7):24-27 (2006).

Tamilvanan et al. "The potential of lipid emulsion for ocular delivery of lipophilic drugs," European Journal of Pharmaceutics and Biopharmaceutics, 58:357-368. (2004).

Xia et al. "A potential application of a piezoelectric atomiser for opthalmic drug delivery," BOB, 4(1):9-17. (2007).

Yee et al. "Trends in Glaucoma Treatment," EyeWorld Educational Symposium, San Francisco, 8 pages. (2006).

Yuan et al. "MEMS-based piezoelectric array microjet," Microelectronic Engineering, 66:767-772. (2003).

Becker, E.W. et al. (1986). "Fabrication of microstructures with high aspect ratios and great structural heights by synchrotron radiation lithography, galvanoforming, and plastic moulding (LIGA process)." *Microelectronic Engineering*, vol. 4, Issue 1, 35-56.

Brown et al. (1965) "The Preservation of Ophthalmic Preparations" *J. Soc. Cosmetic Chemists*, vol. 16:369-393.

Cheng, C.H. et al. (2005). "Multilevel electroforming for the components of a microdroplet ejector by UV LIGA technology." *Journal of Micromechanics and Microengineering*. 15. 843-848. doi: 10.1088/0960-1317/15/4/023.

Ming, Jr., L. et al. (2010, published Dec. 14, 2009), "Influence of liquid hydrophobicity and nozzle passage curvature on microfluidic dynamics in a drop ejection process," *Journal of Micromechanics and Microengineering*, vol. 20:015033, 14 pp, XP020168894.

Miyajima, H. et al. (Dec. 1995), "High-Aspect-Ratio Photolithography for MEMS Applications." *Journal of Microelectromechanical Systems*, vol. 4, No. 4, pp. 220-229, doi: 10.1109/84.475549.

Ostendorf, A. et al. (Apr. 1, 2002). "Development of an industrial femtosecond laser micromachining system," *Proc. SPIE 4633, Commercial and Biomedical Applications of Ultrafast and Free-Electron Lasers*, vol. 4633, pp. 128-135, https://doi.org/10.1117/12.461372.

Santvliet, L.V. et al. (2004). "Determinants of Eye Drop Size." *Survey of Ophthalmology*, 49(2), 197-213. https://doi.org/10.1016/j.survophthal.2003.12.009.

* cited by examiner

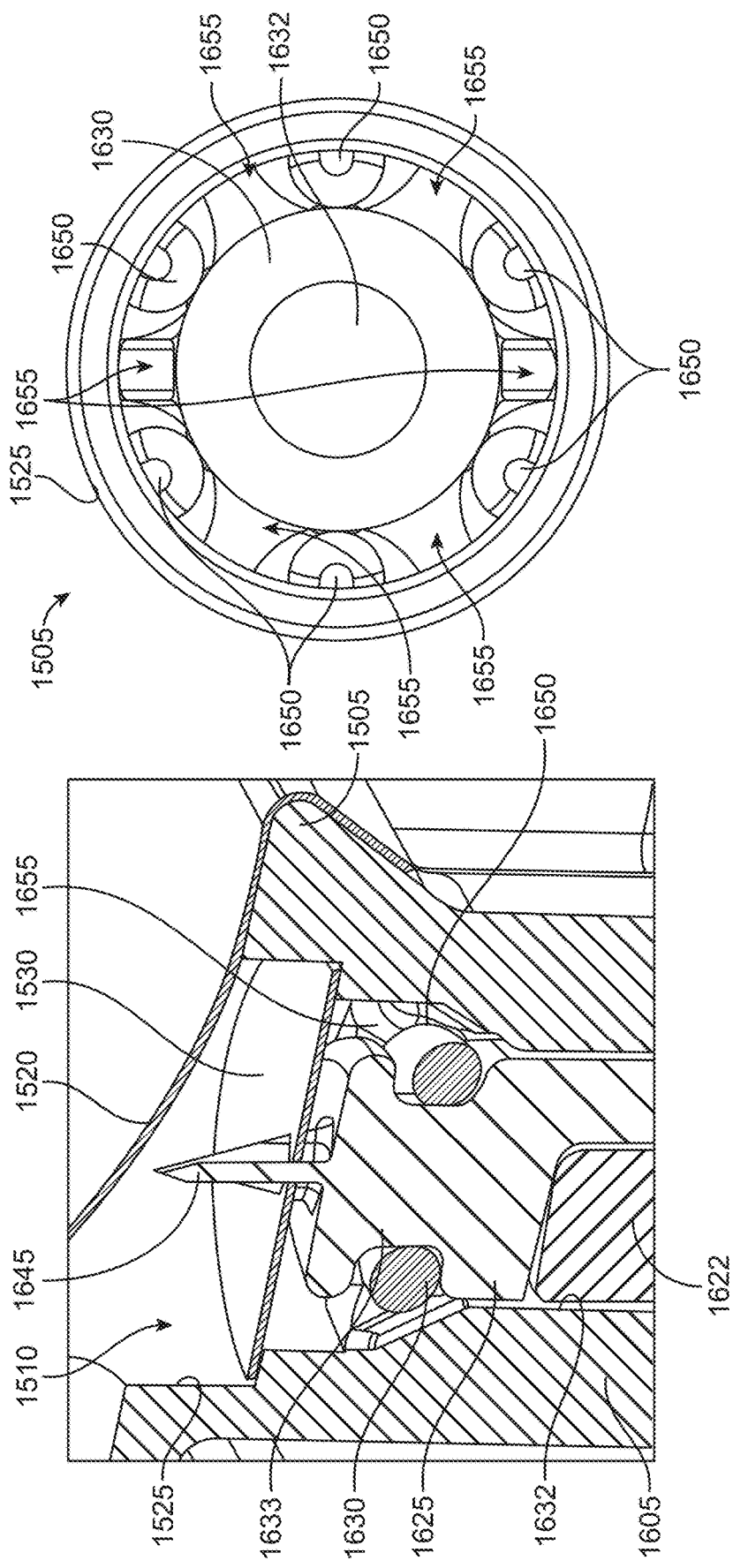

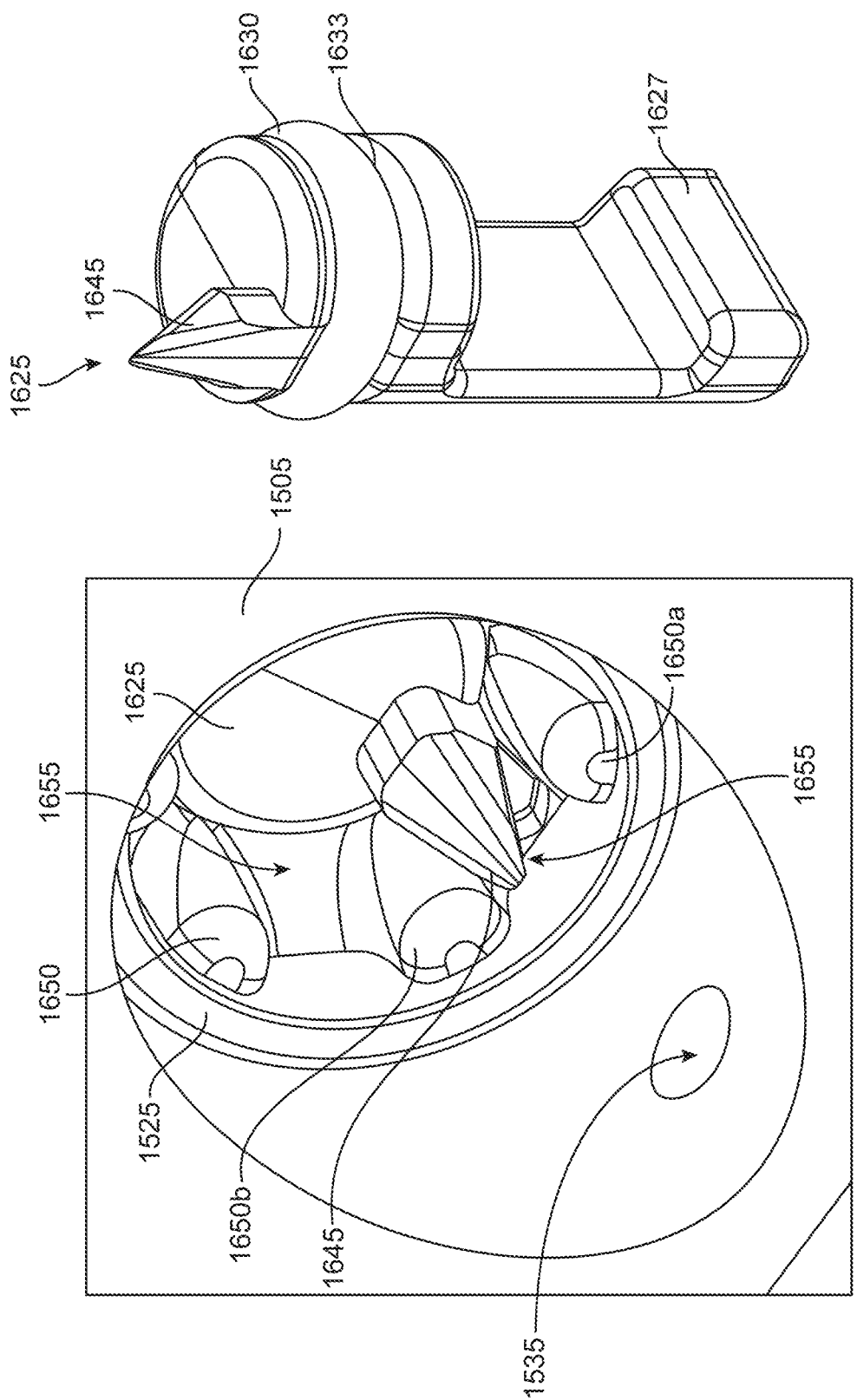

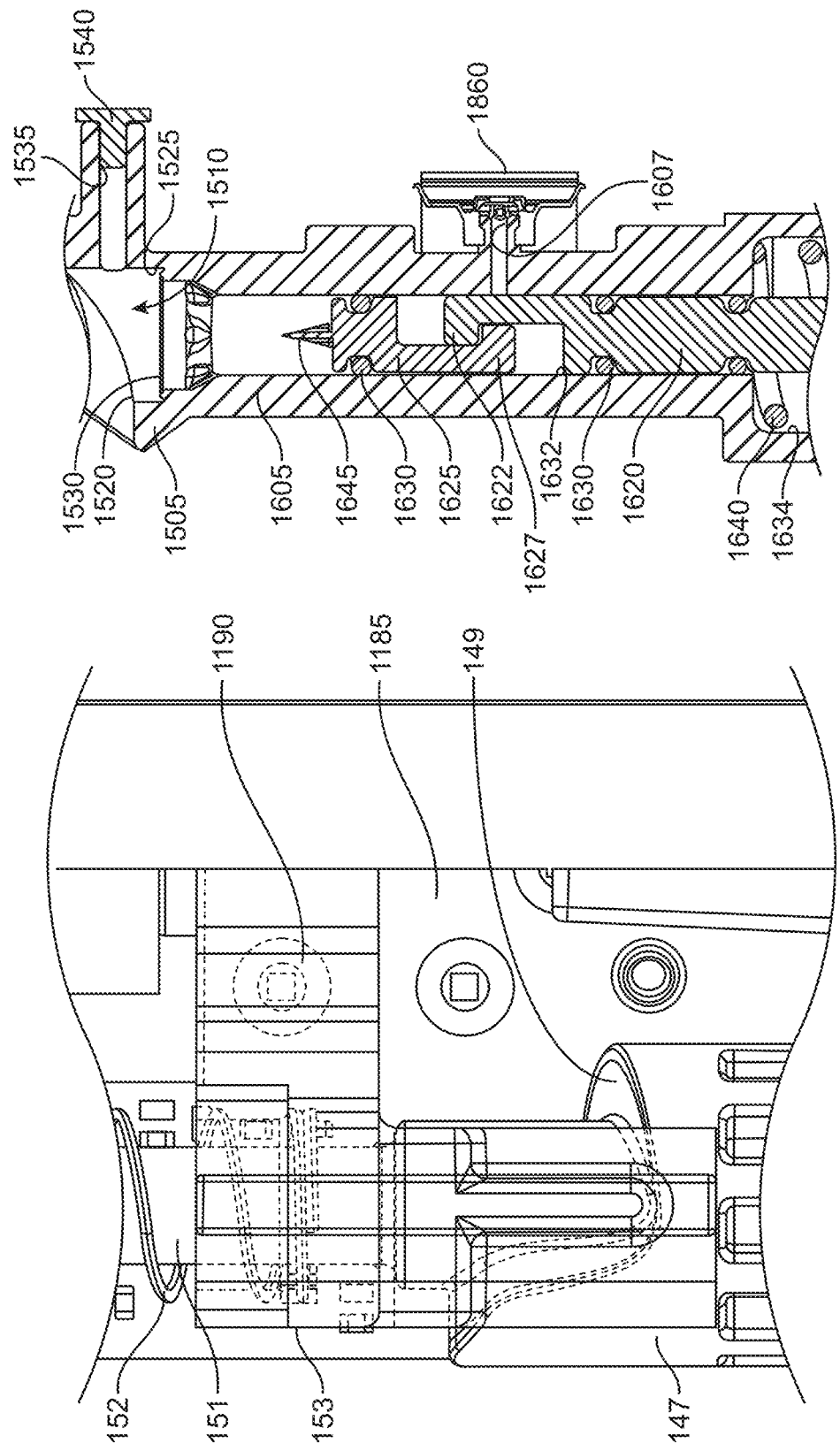

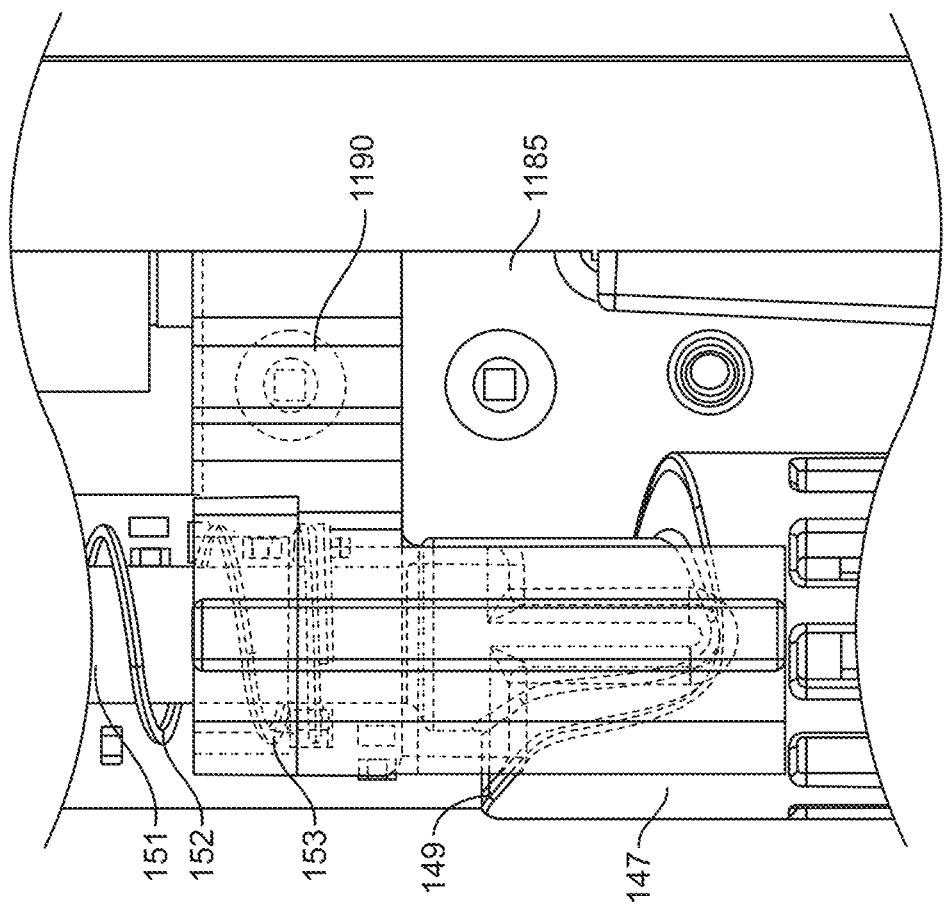
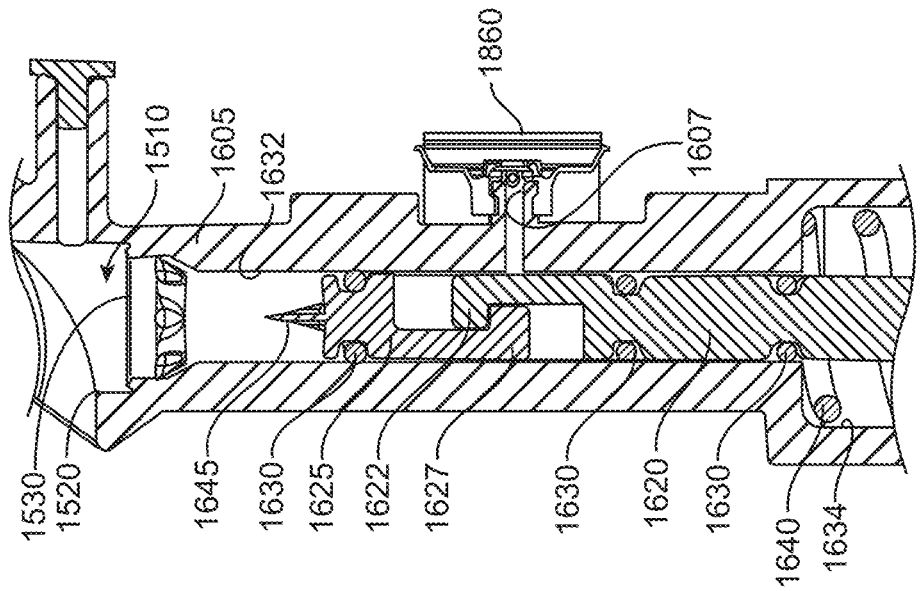
FIG. 10E-1
FIG. 10E-2

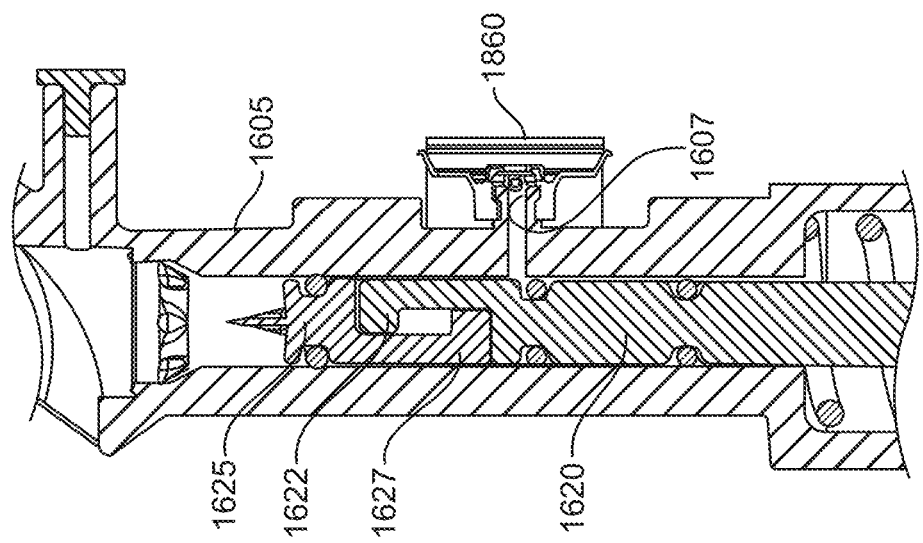
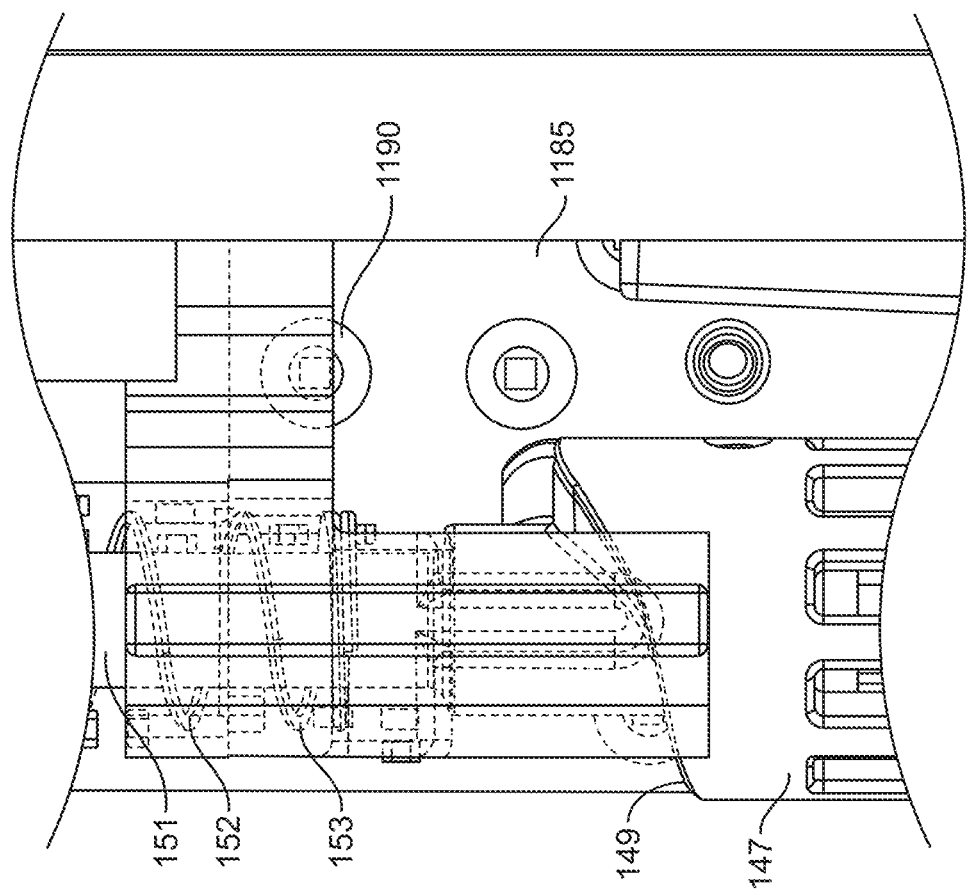
FIG. 10F-2
FIG. 10F-1

SYSTEMS AND DEVICES FOR DELIVERING FLUIDS TO THE EYE AND METHODS OF USE

CROSS-REFERENCE TO RELATED APPLICATIONS

This application claims the benefit of priority under 35 U.S.C. 119§ to U.S. Provisional Patent Application Ser. No. 62/946,727, filed Dec. 11, 2019. The disclosures of the provisional application is incorporated by reference in its entirety.

FIELD

The present technology relates generally to systems and devices for handling a fluid and for delivering fluids to the eye, more particularly to microdroplet delivery systems and devices for ophthalmic use.

BACKGROUND

Drug delivery to the eye using medical eye droppers presents a number of challenges. Medical eye droppers typically dispense single drops having relatively large volume (e.g. about 50 mL). The human eye can retain only a fraction of these large volume drops on the corneal surface (e.g. about 7 mL). Consequently, most of the drug may be wasted due to overflow with less than ideal amounts being delivered to the targeted tissue. In addition, large volume single drops of medication can cause the blinking reflex that also contributes to a large fraction of the delivered fluid being lost. Conventional medical eye droppers can cause discomfort due to these large volume drops triggering the blinking reflex. Discomfort is also worsened by the need for vertical delivery when using conventional medical eye droppers. Vertical delivery of eye drops requires the patient to angle their head upwards to prevent waste of the drop, which is particularly problematic for the elderly. These challenges ultimately contribute to poor patient compliance.

SUMMARY

In an aspect described is a device for delivering a volume of fluid to an eye. The device includes a base having a drive mechanism; and a disposable fluid cartridge configured to releasably couple to the base to form the device. The cartridge includes a piezoelectric-driven fluid ejector; a fluid container having a reservoir manifold having an exit port, a reservoir film movably coupled to the reservoir manifold; and a manifold film positioned within the exit port. The reservoir manifold, manifold film, and reservoir film define an internal volume of the container that is sized to hold a plurality of doses of a therapeutic agent. The cartridge includes a pump configured to draw a dose from the plurality of doses held in the container through the exit port and deliver the dose to the fluid ejector.

The fluid ejector can be configured to eject the dose as a horizontal stream of microdroplets to a cornea of an eye. The reservoir film can tent outward from the reservoir manifold and collapse inward toward the reservoir manifold dependent upon the plurality of doses contained within the internal volume. The reservoir film can collapse towards the reservoir manifold as the dose is drawn from the internal volume by the pump. The fluid container can include no vent. The internal volume of the container can remain sealed from ambient air during use. The reservoir film can be a flexible, non-permeable material. The flexible, non-permeable material can be a polymer or foil that is not elastic or stretchy.

The reservoir manifold can include a concave inner surface and a mating edge at an outer perimeter of the concave inner surface. The mating edge of the reservoir manifold can mate with a corresponding outer perimeter of the reservoir film. The exit port can be located on a lower end region of the reservoir manifold. The manifold film can separate the internal volume of the container from a pumping manifold of the pump. The drive mechanism can be a motor-driven cam configured to operatively couple with the pump. The device can further include a single actuator that, upon actuation, causes the pump to draw and deliver the dose to the fluid ejector, and activate the piezoelectric-driven fluid ejector to eject the dose to the eye. The device can further include a dose button. Penetration of the manifold film can occur only upon actuation of the dose button. The device can further include a protective shutter arranged to cover the dose button and the fluid ejector. Opening the protective shutter can electronically wake the base.

The therapeutic agent can be tropicamide, phenylephrine, atropine, latanoprost, or pilocarpine. The therapeutic agent can be for the treatment of glaucoma, presbyopia, myopia, or mydriasis.

In an interrelated implementation, provided is a device for delivering a volume of fluid to an eye that includes a base comprising a motor-driven cam; and a disposable fluid cartridge configured to releasably couple to the base to form the device. The cartridge includes a piezoelectric-driven fluid ejector; a fluid container defining an internal volume sized to hold a plurality of doses of a therapeutic agent; and a pump configured to draw a dose from the plurality of doses held in the container and deliver the dose to the fluid ejector. The pump includes a pumping manifold defining an inner bore; a drive spool slidingly positioned within the inner bore and operatively coupled to the motor-driven cam; and a floating spool movably coupled to the drive spool and slidingly positioned within the inner bore.

The fluid ejector can be configured to eject the dose as a horizontal stream of microdroplets to a cornea of an eye. The device can further include a single actuator that, upon actuation, causes the pump to draw and deliver the dose to the fluid ejector, and activate the piezoelectric-driven fluid ejector to eject the dose to the eye. The device can include a dose button. The device can include a protective shutter arranged to cover the dose button and the fluid ejector. Opening the protective shutter can electronically wake the base.

The therapeutic agent can include tropicamide, phenylephrine, atropine, latanoprost, or pilocarpine. The therapeutic agent can be for the treatment of glaucoma, presbyopia, myopia, or mydriasis.

The drive spool can include two sliding seals encircling a main body of the drive spool, the two sliding seals having an upper seal and a lower seal. The floating spool can include one sliding seal encircling a portion near an upper end of the floating spool. The sliding seal on the floating spool and the upper seal on the drive spool can seal a space between the spools so that the dose drawn by the pump from the fluid container is maintained within the space. Sliding motion of the drive spool can cause sliding motion of the floating spool when the floating spool is engaged with the drive spool. Reciprocal, linear motion of the drive spool can draw the dose from the fluid container and deliver the dose to the fluid ejector. A first amount of rotation by the motor-driven cam can cause the drive spool and the floating spool to be urged toward the fluid container. The floating spool can include a projection that penetrates by piercing or lifting a manifold film of the fluid container placing the internal volume of the fluid container in fluid communication with the pumping manifold. A second amount of rotation by the motor-driven cam can withdraw the drive spool away from the floating spool increasing a space between the drive spool and floating spool to draw the dose from the fluid container into the inner bore. A third amount of rotation can draw the drive spool away from the floating spool until the drive spool and floating spool engage with one another and the drive spool pulls the floating spool through the inner bore until the dose in the space is aligned with the fluid ejector. A fourth amount of rotation can urge the drive spool towards the floating spool collapsing the space between the spools and delivering the dose within the space to the fluid ejector. A volume of the dose can be about equal to a cross-sectional area of the inner bore multiplied by a length of displacement between the drive spool and the floating spool. The length of displacement between the drive spool and the floating spool can be about 0.100" to about 0.300" and the volume of the dose can be about 2 ul to about 15 ul.

In an interrelated implementation, provided is a device for delivering a volume of fluid to an eye. The device includes a base comprising a drive mechanism; and a disposable fluid cartridge configured to releasably couple to the base to form the device. The cartridge includes a piezoelectric-driven fluid ejector; a fluid container defining an internal volume sized to hold a plurality of doses of a therapeutic agent; and a pump configured to draw a dose from the plurality of doses held in the container and deliver the dose to the fluid ejector. The fluid container includes an exit port having a manifold film positioned within the exit port. The pump includes a pumping manifold defining an inner bore separated from the internal volume of the fluid container by the manifold film positioned within the exit port; and a drive spool having a first end region operatively coupled to the drive mechanism and a second end region movably coupled to a floating spool. The drive spool and floating spool are slidingly positioned within the inner bore. The floating spool includes a projection arranged to place the inner bore in fluid communication with the internal volume of the fluid container.

The projection can be configured to lift the manifold film relative to the exit port. The projection can have a cutting edge geometry configured to pierce the manifold film. The cutting edge geometry can allow for fluid to pass around the projection when the projection pierces the manifold film. The floating spool can include a sliding seal encircling an upper end portion of the floating spool. The sliding seal of the floating spool can seal with at least a first region of the inner bore of the pumping manifold. The pumping manifold can further include an upper inlet region that tapers from an inner diameter of the exit port to a smaller inner diameter of the first region. The upper inlet region can include a plurality of surface features allowing for fluid flow around the sliding seal of the floating spool when the floating spool is in its uppermost position within the inner bore. The sliding seal can be compressed between a surface of the floating spool and walls of the inner bore creating a complete seal. The complete seal can break when the sliding seal of the floating spool enters the upper inlet region of the pumping manifold. The drive spool and the floating spool can define a variable volume pumping chamber. Withdrawing the drive spool away from the floating spool can increase the variable volume pumping chamber and create a vacuum within the pumping chamber to draw fluid from the internal volume of the fluid container. The projection can be eccentric relative to an upper surface of the floating spool. A reservoir manifold of the fluid container can slope downwards towards the exit port. A wetted delivery flow path can extend between a lower end of the fluid container to the fluid ejector through the inner bore. The wetted delivery flow path can be L-shaped and have a length that is between about 0.5 inch and 1.0 inch.

In an interrelated implementation, provided is a microdroplet or an aqueous pharmaceutical composition that is one of (a) about 2.0 wt % to about 3.0 wt % phenylephrine and about 0.5 wt % to about 1.5 wt % tropicamide, and about 0.005 wt % to about 0.06 wt % benzalkonium chloride; (b) about 0.05 wt % to about 0.2 wt % atropine, about 0.10 wt % to about 0.15 wt % sodium phosphate, about 0.009 wt % to about 0.016 wt % benzalkonium chloride, and about 0.8 wt % to about 1.0 wt % sodium chloride; (c) about 0.005 wt % to about 0.006 wt % atropine, about 0.10 wt % to about 0.15 wt % sodium phosphate, about 0.009 wt % to about 0.016 wt % benzalkonium chloride, and about 0.8 wt % to about 1.0 wt % sodium chloride; (d) about 0.005 wt % to about 0.01 wt % latanoprost, about 0.10 wt % to about 0.15 wt % sodium phosphate, about 0.01 wt % to about 0.03 wt % benzalkonium chloride, about 0.8 wt % to about 1.0 wt % sodium chloride, and about 0.1 wt % to about 0.3 wt % of a polypropylene glycol/polyethylene glycol copolymer; (e) about 0.05 wt % to about 1.5 wt % pilocarpine, about 0.1 wt % to about 0.2 wt % sodium phosphate, about 0.001 wt % to about 0.02 wt % benzalkonium chloride, and about 0.2 wt % to about 0.6 wt % sodium chloride; (f) about 0.05 wt % to about 1.5 wt % pilocarpine, about 0.1 wt % to about 0.2 wt % sodium phosphate, about 0.001 wt % to about 0.02 wt % benzalkonium chloride, and about 0.6 wt % to about 1.0 wt % sodium chloride; (g) about 1.5 wt % to about 2.5 wt % pilocarpine, about 0.1 wt % to about 0.2 wt % sodium phosphate, about 0.001 wt % to about 0.02 wt % benzalkonium chloride, and about 0.2 wt % to about 0.6 wt % sodium chloride; and (h) about 1.5 wt % to about 2.5 wt % pilocarpine, about 0.1 wt % to about 0.2 wt % sodium phosphate, about 0.001 wt % to about 0.02 wt % benzalkonium chloride, and about 0.6 wt % to about 1.0 wt % sodium chloride.

The microdroplet or the aqueous pharmaceutical composition can be selected from one of: (a) about 2.5 wt % phenylephrine, about 1.0 wt % tropicamide, about 0.01 wt % benzalkonium chloride, and sodium chloride; (b) about 0.1 wt % atropine, about 0.136 wt % sodium phosphate, about 0.011 wt % benzalkonium chloride, and about 0.9 wt % sodium chloride; (c) about 0.01 wt % atropine, about 0.136 wt % sodium phosphate, about 0.011 wt % benzalkonium chloride, and about 0.9 wt % sodium chloride; (d) about 0.0075 wt % latanoprost, about 0.136 wt % sodium phosphate, about 0.02 wt % benzalkonium chloride, about 0.9 wt % sodium chloride, and about 0.2 wt % of a polypropylene glycol/polyethylene glycol copolymer; (e) about 1.0 wt % pilocarpine, about 0.136 wt % sodium phosphate, about 0.011 wt % benzalkonium chloride, and about 0.4% wt sodium chloride; (f) about 1.0 wt % pilocarpine, about 0.136% wt % sodium phosphate, about 0.011 wt % benzalkonium chloride, and about 0.8% wt sodium chloride; (g) about 2.0 wt % pilocarpine, about 0.136% wt % sodium phosphate, about 0.011 wt % benzalkonium chloride, and about 0.4% wt sodium chloride; and (h) about 2.0 wt % pilocarpine, about 0.136% wt % sodium phosphate, about 0.011 wt % benzalkonium chloride, and about 0.8% wt sodium chloride.

In some variations, one or more of the following can optionally be included in any feasible combination in the above devices, systems, compositions, and methods of using the devices, systems, and compositions herein. More details of the methods, apparatus, devices, systems, and compositions are set forth in the accompanying drawings and the description below. Other features and advantages will be apparent from the description and drawings.

BRIEF DESCRIPTION OF THE DRAWINGS

FIG. 6C is a detailed view of the pump in FIG. 6B showing at least a portion of the pump in fluid communication with the reservoir;

FIG. 6D is a downward view of an exit port from the reservoir showing an o-ring in an upper region of the pump;

FIG. 6E is another view of the exit port from the reservoir showing a projection on an upper region of a portion of the pump.

FIG. 6F is a perspective view of a floating spool incorporating a projection and sliding seal;

FIGS. 10A-1 and 10A-2 illustrate the base device and pump within a pumping chamber, respectively, while the base device is in a LOW position;

FIGS. 10B-1 and 10B-2 illustrate the base device and pump within a pumping chamber, respectively, while the base device is in a HOME position;

FIGS. 10C-1 and 10C-2 illustrate the base device and pump within a pumping chamber, respectively, at the start of a drawdown phase;

FIGS. 10D-1 and 10D-2 illustrate the base device and pump within a pumping chamber, respectively, at the end of the drawdown phase;

FIGS. 10E-1 and 10E-2 illustrate the base device and pump within a pumping chamber, respectively, at the start of an ejection phase;

FIGS. 10E-1 and 10E-2 illustrate the base device and pump within a pumping chamber, respectively, at the end of the ejection phase;

Generally speaking, the figures are not to scale in absolute terms or comparatively, but are intended to be illustrative. Also, relative placement of features and elements may be modified for the purpose of illustrative clarity. It is to be understood that devices described herein may include features not necessarily depicted in each figure.

DETAILED DESCRIPTION

Described herein are systems, devices, and methods for handling a fluid and for delivering fluids to the eye. The systems and devices described herein are designed to deliver microdoses of a therapeutic, particularly ophthalmic formulations of a therapeutic to the eye (e.g., cornea) within a physiologic range of the tear film capacity using a uniform, collimated stream of micro droplets to coat an ocular surface. The systems and devices described herein can be used with a single hand in an intuitive, easy-to-operate manner. The systems and device described herein provide can provide direct corneal delivery along a horizontal axis or orientation to eliminate the need for angling the head in an unnatural position to receive a treatment.

The various features and functions of the devices described herein may be applied to one or more devices described herein even though they may not be expressly described in combination. It should also be appreciated that various features and functions of the devices described herein can be applied to conventional devices and systems known in the art also useful for delivery of a medicament to the eye.

Fluid Delivery System

Figure 1:
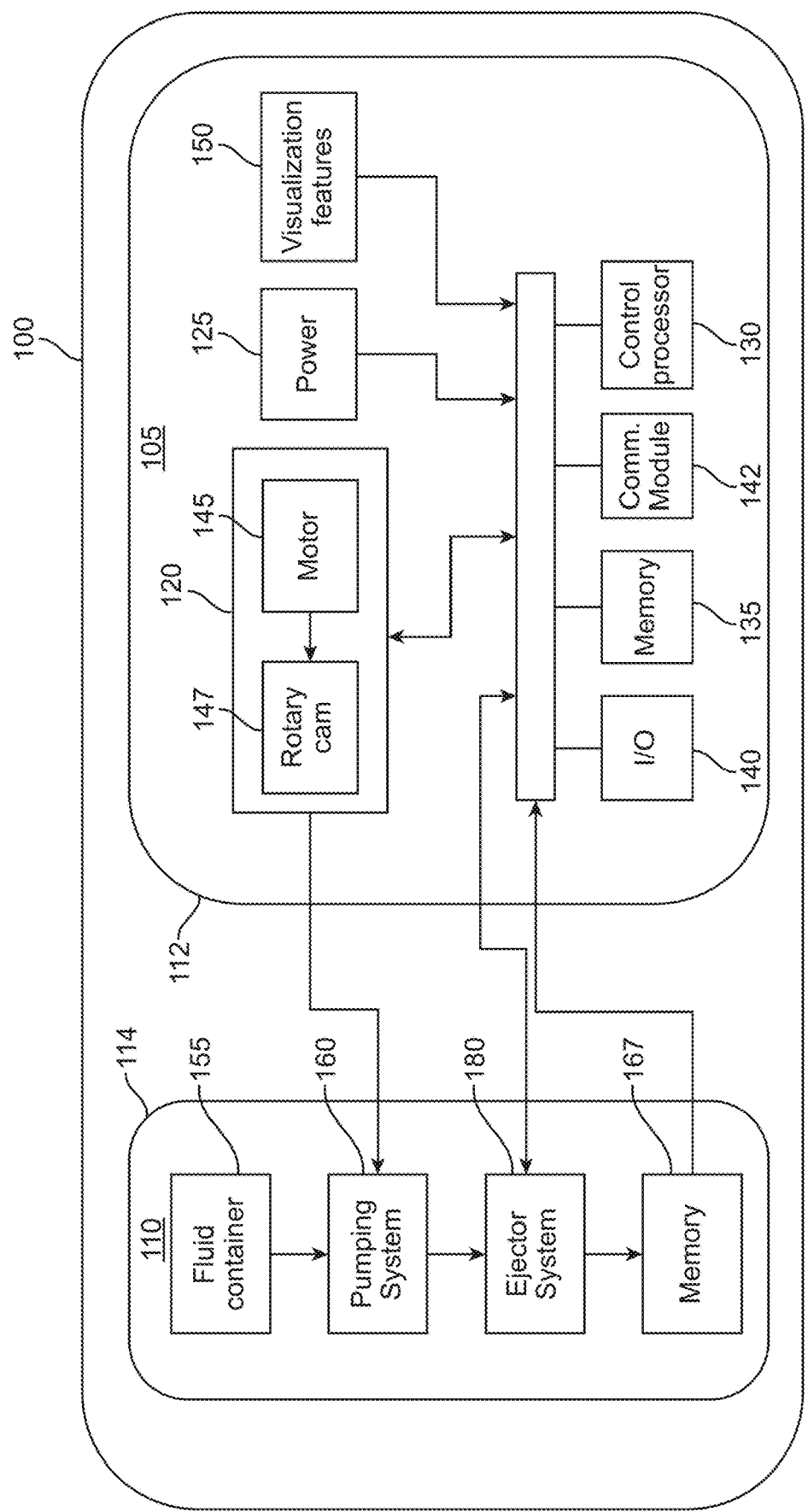
FIG. 1 is a box diagram illustrating a fluid delivery system including a cartridge and a base device.

FIG. 1 illustrates a block diagram of a fluid delivery system 100 according to an implementation. The fluid delivery system 100 can include a base device 105 and a cartridge 110. The base device 105 can be a durable, reusable component that can be used for an extended period of time compared to the cartridge 110. The cartridge 110 can be a disposable, non-reusable component that can be used for a limited period of time compared to the base device 105. A single cartridge 110 can be used with the base device 105 to supply a user with medication over an extended period of days, for example between 1 to about 30 days. For example, the cartridge 110 can be a 30-day disposable whereas the base device 105 can be used for 1, 2, 3 or more years. The cartridge 110 can incorporate a container size of any of a variety of volumes to allow for treatment for more than 30 days The cartridge 110 can be disposed after a number of uses of the system including after at least 1, 2, 5, 10, 15, 20, 30, 50 up to about 100 doses delivered. The base device 105 can connect with different cartridges 110 containing different medications depending upon a user's need. Thus, the base device 105 is fully interchangeable with a plurality of different cartridges 110.

The cartridge 110 generally incorporates the "wet" components and is configured to come into direct contact with the fluids to be delivered. The base device 105 generally includes the components of the system 100 that are configured to remain outside the fluid path. It should also be appreciated that both the base device 105 and the cartridge 110 can be either disposable or durable. For example, the entire system 100 may be disposable and manufactured of lower cost materials such that it is financially feasible for the base device 105 to also be disposed of after a short term use.

Still with FIG. 1, the base device 105 can include a housing 112 configured to substantially enclose a pump drive system 120. The base device can also include electronics such as power 125, control processor 130, memory 135, one or more input/outputs 140, and optionally a communication module 142. The control processor 130, memory 135, one or more input/outputs 140, communication module 142, as well as any storage devices, etc., can be interconnected via a system bus 143. The base device 105 can optionally include visualization features 150 to aid in the delivery of fluid from the system 100 to the patient. The visualization features 150 can vary including lighting such as an LED connected to a light pipe 1151, one or more mirrors 1152, or other feature. The pump drive system 120 can include an electric motor 145 arranged to drive a rotary cam 147. As will be discussed in more detail below, the cam 147 can be positioned within the housing 112 of the base device 105 as shown in FIG. 1. The cam 147 can also be positioned within the cartridge 110 and configured to couple with the motor 145 (e.g. via a motor coupler or other feature) that is available outside the housing 112 of the base device 105.

Still with respect to FIG. 1, the cartridge 110 can include a housing 114 configured to substantially enclose a fluid container 155, a pumping system 160, and an ejector system 180. The cartridge 110 can optionally incorporate a memory 167 or other data device. The fluid container 155 can be a non-evaporative primary drug container filled with a liquid medicament to be delivered to a user in droplet form. The pumping system 160 is arranged to draw discrete volumes or doses of medicament from the fluid container 155 and deliver those doses to the ejector system 180. The ejector system 180 can be a piezoelectric ejector system configured to deliver the dose of medicament drawn by the pumping system from the fluid container in the form of microdroplets.

Figure 2A:
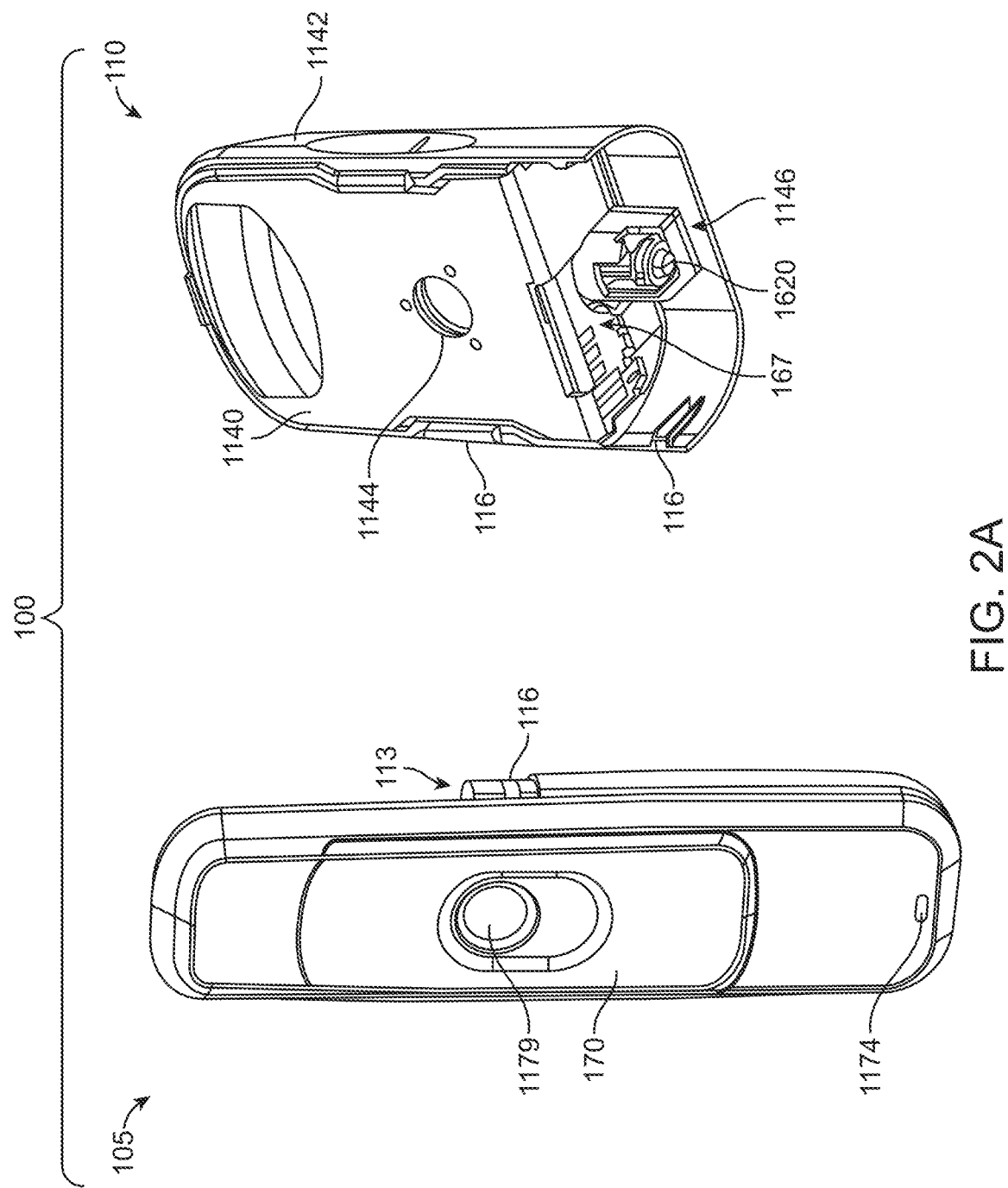
FIG. 2A shows an exploded perspective view of the fluid delivery system including a base device and a cartridge.
Figure 2C:
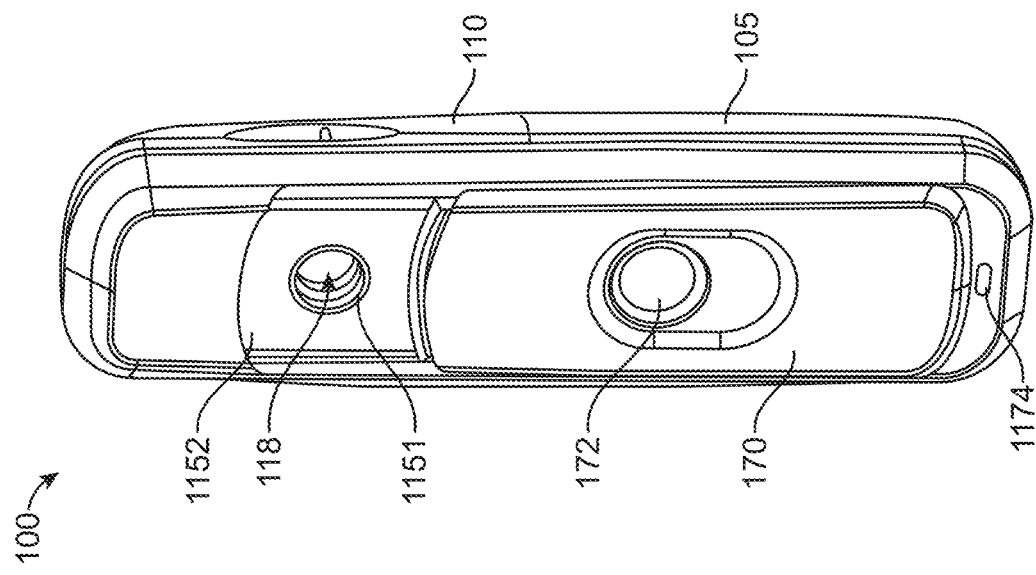
FIG. 2C shows the system of FIG. 2A with the cartridge installed on the base device and a shutter on the base device in the open configuration revealing a dose button.
Figure 2B:
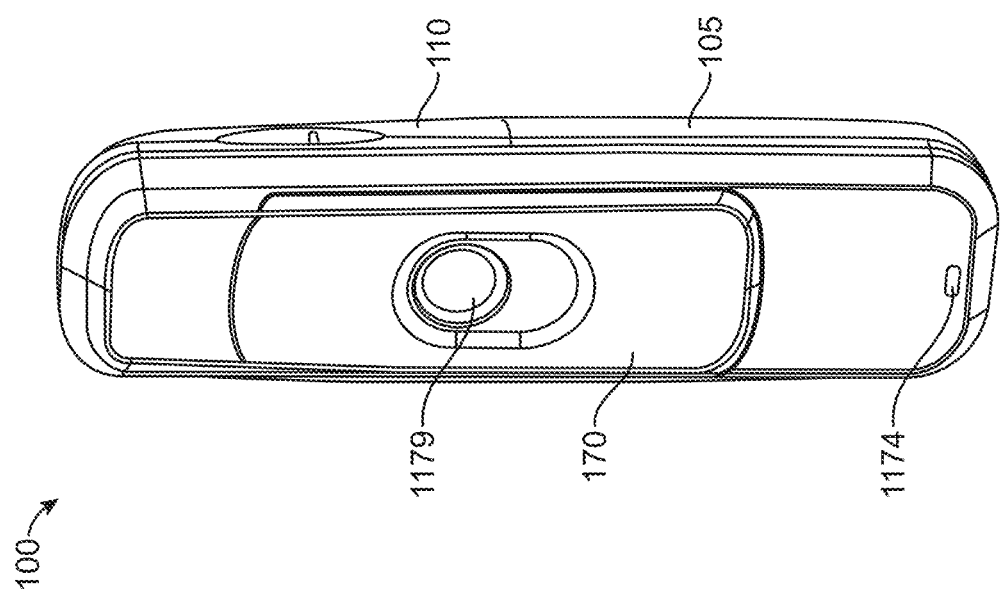
FIG. 2B shows the system of FIG. 2A with the cartridge installed on the base device.

FIG. 2A shows an exploded perspective view of the system 100 including the base device 105 and the cartridge 110. FIG. 2B shows the system 100 with the cartridge 110 installed on the base device 105. FIG. 2C shows the system 100 with the cartridge 110 installed on the base device 105 and a shutter 170 on the base device 105 in the open configuration revealing a dose button 172 and a spray aperture 118. The cartridge 110 may be a reversibly removable and interchangeable element that can be inserted within a corresponding slot 113 formed by the housing 112 of the base device 105 (see FIG. 2A). The housing 114 of the cartridge 110 and the housing 112 of the base device 105 can incorporate complementary alignment and attachment features 116 on their respective external surfaces such that the cartridge 110 may be reversibly attached and detached from the base device 105. The coupling between the cartridge 110 and the base device 105 ensures operative engagement between the drive system 120 of the base device 105 and the pumping system 160 of the cartridge 110, which will be described in more detail below.

The implementation shown in FIGS. 2A-2C provides coupling between the cartridge 110 and the base device 105 in an orientation relative to the user where the cartridge 110 is positioned on an upper end region of the base device 105. The location of coupling between the cartridge 110 on the base device 105 can vary and need not be exactly as shown. For example, other configurations are considered where the cartridge 110 couples to a back, lower, upper, or front side of the base device 105. The cartridge 110 can also be fully enclosed by a slot 113 of the housing 112 of the base device 105. Regardless of the coupling configuration of the cartridge 110 and the base device 105, the fully assembled fluid delivery system 100 can have a smooth ergonomic feel such that the housing 114 of the cartridge 110 and the housing 112 of the base device 105 together form a single system housing. The single system housing (i.e., the housing formed by the cartridge 110 installed with the base device 105) can be of any suitable shape and size. For instance, the single system housing can be relatively tubular to fit easily and ergonomically within a palm of the user's hand. The shape can be cylindrical, rectangular, square, oval, and the like. The single system housing may be dimensioned so as to be comfortably associated with a user's hand. The size of the single system housing can be suitable for single-hand use and easy storage within a pocket or purse. In some implementations, the single system housing may have a width of about 30 mm to about 45 mm and a height of about 100 mm to about 150 mm.

The materials of the housings may vary. The housing 114 of the cartridge 110 can be typically formed of disposable plastic whereas the housing 112 of the base device 105 can be made of more durable plastic or metal. The housing 112 of the base device 105 may be taken apart for repairs. In some implementations, the housing 112 of the base device 105 may be a water-tight, plastic housing that is glued together permanently.

The base device 105 and cartridge 110 and their components will be described in more detail below.

Base Device

Again with respect to FIG. 1, the base device 105 can include the electronics of the system 100 and at least a portion of the pump drive system 120. The electronics of the base device 105 can include a control processor 130, a memory 135, one or more input/outputs 140, and power 125. The control processor 130 can be in operative communication with one or more of the power 125 system, the drive system 120, the ejector system 180, and any electronics in the cartridge 110. The control processor 130 can be capable of processing instructions for execution within the system 100. Such executed instructions can implement one or more of the processes described herein related to the use of the system 100. The control processor 130 can be a single-threaded processor or a multi-threaded processor. The control processor 130 can be capable of processing instructions stored in the memory 135 and/or on a storage device to provide an output of information to the user about operation of the system 100. The control processor 130 can include software capable of being programmed. The software run by the control processor 130 can provide certain aspects of the system 100 without any user input during use. In an implementation, the adjustments or programming can be via the control processor 130 that is controlled by software.

Still with respect to FIG. 1, the control processor 130 can communicate with or otherwise control operation of the drive system 120, input/output 140, the memory 135, the communication module 142, and the like of the base device 105. The control processor 130 can also include programming configured to control one or more components of the cartridge 110 upon coupling the cartridge 110 to the base device 105. For example, the control processor 130 may include circuitry to control timing of the ejector system 180 relative to the state of the drive system 120. The control processor 130(s) can include programming that allows the processor(s) 130 to receive signal and/or other data from an input device 140, such as a sensor, button, or slider. The processors 130 may receive the signals, for example, from a data device 167 or a transmitter/receiver on the cartridge 110 and store the signals in the memory 135. The control processor 130 circuitry may include one or more clocks (oscillators), charging circuitry, I/O controllers, memory, etc.. Alternatively or in addition, the circuitry of the control processor 130 may include circuitry for one or more wireless communication modes, including Bluetooth, nearfield communication (NFC), WiFi, ultrasound, ZigBee, RFID, etc.

The memory 135 of the base device 105 may be part of the control processor 130 or otherwise in data communication with the control processor 130. The memory 135 is configured for receiving and storing user input data. The memory 135 can be configured to store user information, history of use, compliance, drug information, verification of genuine cartridge or source or supplier, and the like. The memory 135 can be any type of memory capable of storing data and communicating that data to one or more other components of the system 100, such as the control processor 130. The memory 135 may be one or more of a Flash memory, SRAM, ROM, DRAM, RAM, EPROM, dynamic storage, and the like. The size of the memory 135 can vary as is known in the art.

The memory 135 of the base device 105 can also receive and store data from a memory or data device of a cartridge 110 coupled to the base device 105. For example, the cartridge 110 can include a data device 167 that is an encoder or bar code type strip. The encoder may be configured to be scanned or read by a reader device on the base device 105 that is in operative communication with the control processor 130. The encoder device 167 may be an RFID chip or the like that transmits data to the reader. Such encoder device 167 embodiments may include the ability to securely transmit and/or store data, such as via, encryption, to prevent unauthorized access or tampering with such data.

Again with respect to FIG. 1, the input/outputs 140 may be combined or the input may be separate from the output. The one or more input/outputs 140 of the base device 105 can include one or more triggers, buttons, sliders, dials, keypads, switches, touchscreens, or other input that can be retracted, pressed, squeezed, slid, tapped, or otherwise actuated to activate, modify, or otherwise cause a response of the system. The shutter 170 and dose button 172 are examples of input/outputs 140 of the system. As another example, the input/outputs 140 of the base device 105 can be one or more indicator lights 1174 that can provide, for example, information about status or power of base device 105 (see FIGS. 2A-2C).

The one or more input/outputs 140 of the base device 105 can also include sensors, accelerometers, motion sensors, capacitive sensors, flow sensors, or the like. These sensors can detect user handling and interaction. The one or more input/outputs 140 can be optical (LED, display), tactile (e.g. vibrational, etc.), sonic (e.g. speaker, etc.), or the like. The one or more input/outputs 140 of the base device 105 can also be more elaborate such as a GUI having an input. The type of visual output/display may include LCD displays, LED displays, plasma displays, OLED displays and the like. The output/display may also be an interactive or touch sensitive screen having an input device such as a touch screen, a capacitance screen, a resistive screen or the like. The one or more input/outputs 140 can also include a vibratory motor, speaker, warning, alarm, alert, clock, timer, or other features.

Power 125 can be supplied to the drive system 120 and/or the control processor 130. In some implementations, the power 125 can be supplied by a battery incorporated within a region of the housing 112, either internally or coupled to a region of the housing 112 such as within a modular, removable battery pack 127 (see FIG. 3). The battery can have different chemical compositions or characteristics. For instance, batteries can include lead-acid, nickel cadmium, nickel metal hydride, silver-oxide, mercury oxide, lithium ion, lithium ion polymer, or other lithium chemistries. The base device 105 can also include rechargeable batteries using either a DC power-port, induction, solar cells, or the like for recharging. The base device 105 can include a power charging mechanism in some cases, such as a USB port, induction charger, or the like. As such, all data may be downloaded to a computer, network etc. using the USB port. The USB port may also provide the base with power charging.

In some implementations, the base device 105 can incorporate a communication module 142 in operative communication with one or more components of the system, such as the control processor 130, as well as with one or more peripheral devices such as the one or more external computing devices. The connection between the base device 105 and other components can also include a wired communication port such as a RS22 connection, USB, Fire wire connections, proprietary connections, or any other suitable type of hard-wired connection configured to receive and/or send information. The communication can also include a wireless communication port such that information can be fed to/from the base device 105 via a wireless link. The wireless connection can use any suitable wireless system, such as Bluetooth, Wi-Fi, radio frequency, ZigBee communication protocols, infrared, or cellular phone systems, and can also employ coding or authentication to verify the origin of the information received. The wireless connection can also be any of a variety of proprietary wireless connection protocols.

The base device 105 may have wired or wireless communication capability such as for the sending and receiving of data as is known in the art. The wireless capability may be used for a variety purposes, including updating of any software or firmware for the processor of the device. The wireless communication capability may vary including, e.g., a transmitter and/or receiver, radiofrequency (RF) transceiver, WIFI connection, infrared or Bluetooth® communication device. The wired communication capability may also vary including, e.g., USB or SD port, flash drive port, or the like. In some embodiments, the cartridge 110 and the base device 105 may each have a transmitter/receiver, such as a radiofrequency (RF) transceiver, that allows them to communicate with one another and be used interchangeably without loss of data or information during use. A user can alternate cartridges 110 with the same base device 105 and the transfer of data between the two can be automatic.

The control processor 130 can also be in operative communication with one or more external computing devices. The external computing device can vary including, but not limited to, desktop computer, laptop computer, tablet computer, smartphone, or other device capable of communicating and receiving user input.

Again with FIG. 1, the pump drive system 120 can include a motor 145 positioned within the base device 105 that is configured to operatively couple with and drive the pumping system 160 of the cartridge 110. The motor 145 can be an electric motor such as a stepper motor, continuous motor, or the like. The motor 145 can be a brushless DC motor or any type of motor or drive suitable for rotating a shaft. The motor 145 can be programmed to have variable pumping speeds and/or multiple rotations upon activation of the base device 105 via a single dose button press allowing for different delivery volumes from the same base device. In some implementations, the motor 145 is an electric motor that incorporates gear reduction via a gear box or other mechanism. In some implementations, the base device 105 incorporates a HarmonicDrive gear reduction. The drive system 120 can also include a hydraulic mechanism, pneumatic mechanism, piezoelectric mechanism, or other drive mechanism.

At least a portion of the drive system 120 can remain available outside the housing 112 of the base device 105 such that it can engage with the corresponding component of the cartridge 110. For example, the motor 145 can engage with and rotate the rotary cam 147 (see FIG. 3). At least a first portion of the rotary cam 147 can be positioned within the base device 105 such that at least another portion of the cam 147 is available outside the housing 112 of the base device 105 for operative coupling with the pumping system 160 of the cartridge 110 to drive fluid flow through the cartridge 110 when the cartridge 110 is installed on the base device 105.

The motor 145 is part of the drive system 120 and is positioned at least partially within the base device 105. The rotary cam 147, however, can be positioned within a region of the base device 105 or within a region of the cartridge 110. In some implementations, the cam 147 is positioned within the base device 105 and engages with the motor 145 within the base device. In other implementations, the cam 147 is positioned within the cartridge 110 and engages with the motor 145 (e.g., via a motor coupler) within the cartridge 110. In an implementation, a gear head 146 of the motor 145 can couple to the rotary cam 147 via a motor coupler such that the rotary cam 147 rotates as the gear head rotates. Any of a variety of coupling configurations of the motor/cam/pumping system 160 coupling is considered herein.

The drive system 120 need not be a motorized system and can incorporate a manual mechanism of effecting pumping. An actuator can be coupled to a region of the base device 105 that is configured to be manually actuated that, in turn, rotates the cam 147. In some implementations, the actuator can be a manually-rotatable ring that directly rotates the cam 147. In still further implementations, the actuator can eliminate the need to convert rotational motion to linear motion and can drive linear motion of the pump without the cam 147. For example, a lever-actuated feature can be incorporated to cause motion of the pump. A lockout feature can be incorporated to prevent multiple actuations. Other manual drive mechanisms are described in U.S. Publication No. 2020/019721, filed Jun. 11, 2018, which is incorporated herein by reference.

Figure 8A:
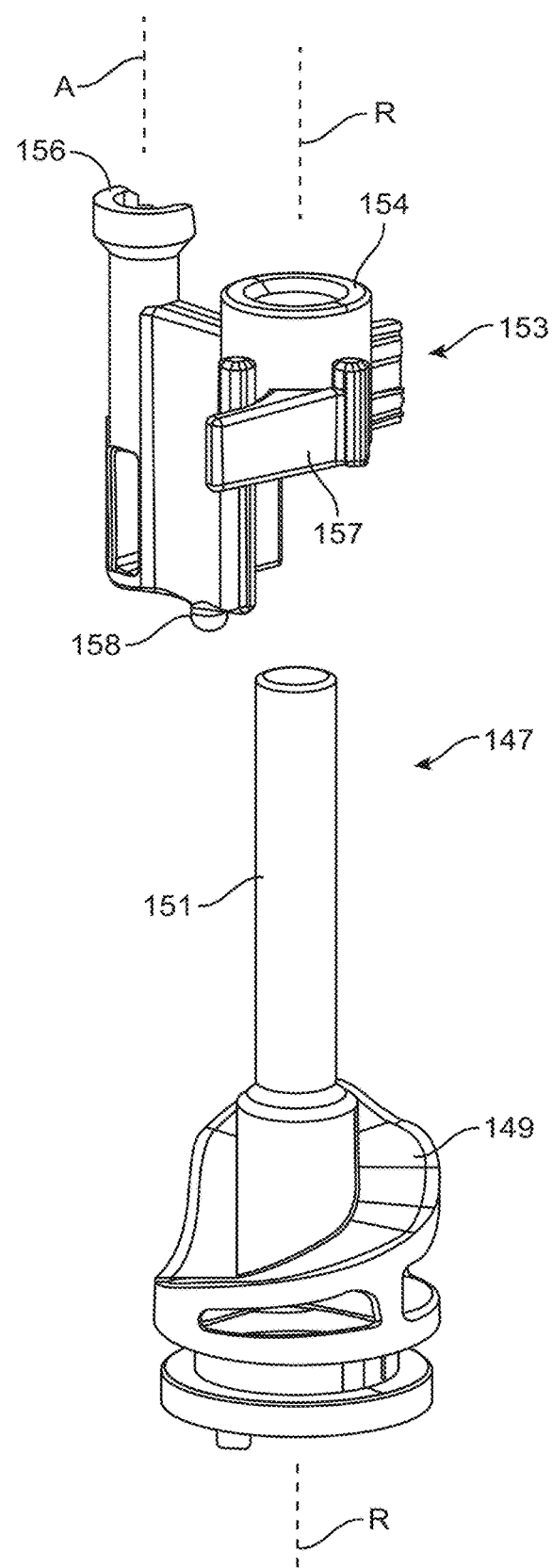
FIG. 8A is a perspective view of a rotary cam and cam follower of the pump drive system.

As best shown in FIG. 8A, the cam 147 can include a cam surface 149 extending around a central cam shaft 151 having a rotational axis R. The geometry of the cam surface 149 can vary including elliptical, eccentric, egg, snail-shaped, and the like. The geometry of the cam surface 149 is designed to translate the rotary motion of the motor 145 into reciprocal axial motion of a pump in the cartridge 110. The geometry provides a specific motion profile and a particular timing of events within the pumping system 160, which will be described in more detail below.

Figure 8C:
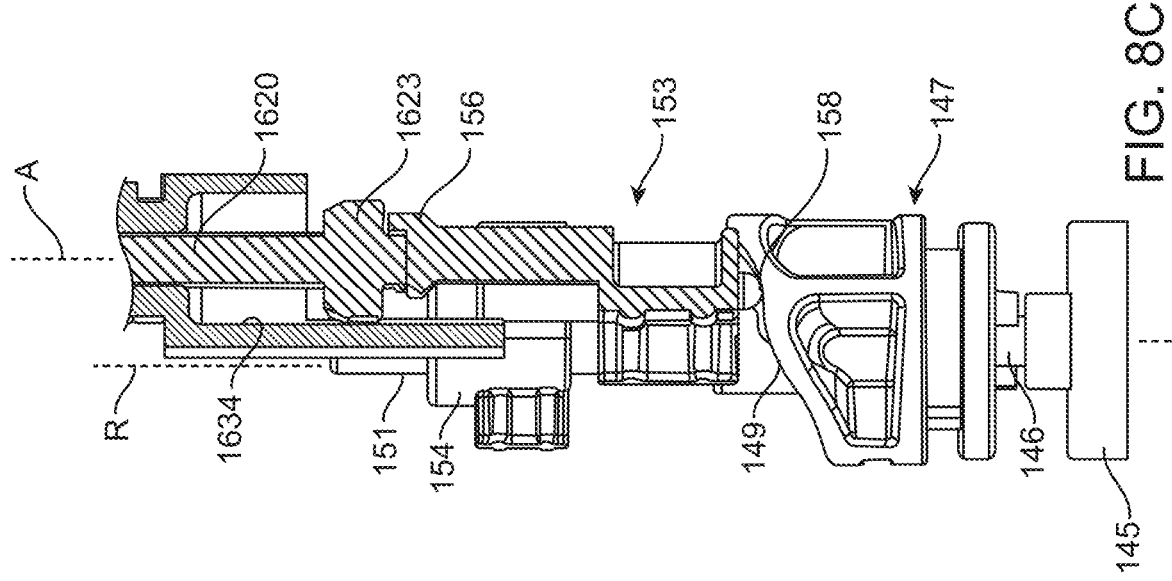
FIG. 8C is a simplified view of the rotary cam, cam follower and pump in engagement.
Figure 8B:
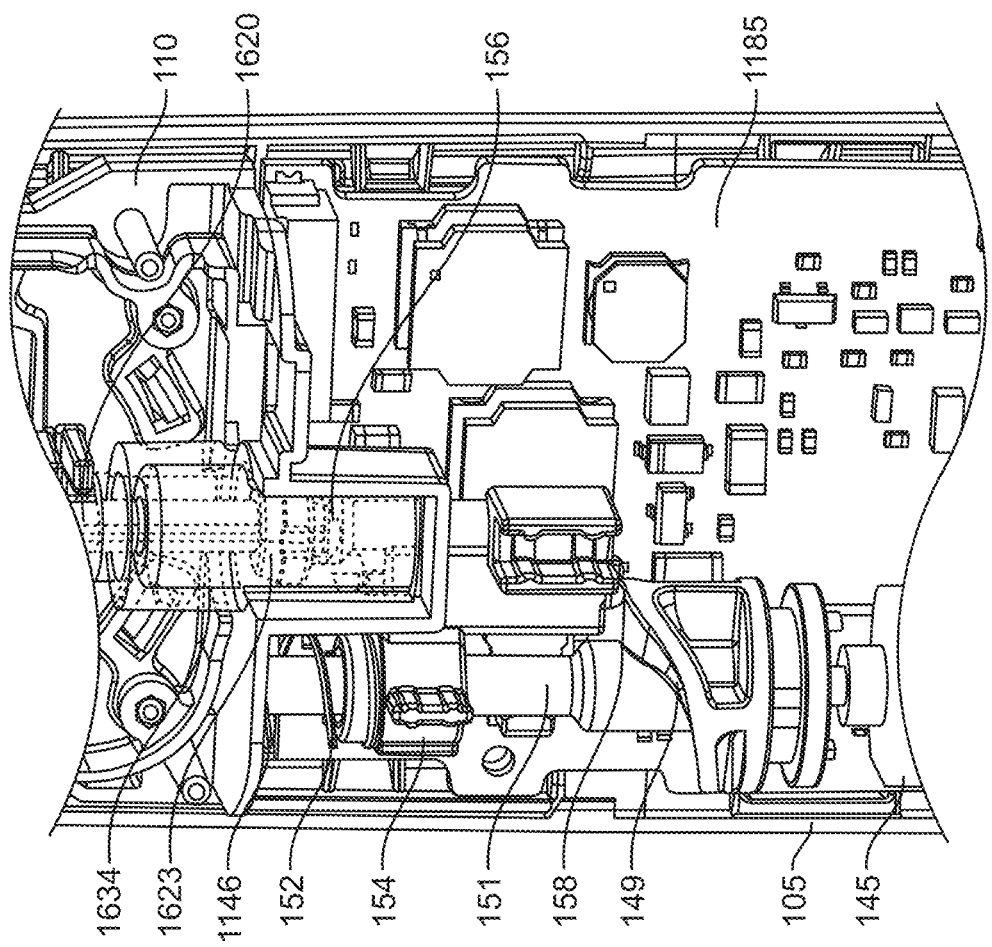
FIG. 8B is a partial view of the rotary cam and cam follower of FIG. 8A engaged with each other and coupled to the pump of the cartridge.

The cam 147 can engage with the pumping system 160 directly or can couple to the pumping system 160 indirectly via a cam follower 153 that, in turn, is coupled to the pumping system 160. As best shown in FIG. 8A, the cam follower 153 can include a bushing 154 coupled to a spool coupler 156. The bushing 154 is aligned with the rotational axis R of the cam shaft 151 such that the cam shaft 151 extends through the bushing 154. The spool coupler 156 extends outward away from axis R of the cam shaft 151 and from the bushing 154. A lower surface of the spool coupler 156 can include a bearing 158 configured to slide along the cam surface 149 as the cam 147 rotates (see also FIGS. 8B-8C). An upper surface of the spool coupler 156 can include a recess configured to receive and mate with a corresponding structure of the pumping system 160 in the cartridge 110. The recess of the spool coupler 156 can have a longitudinal axis that is coaxial with a longitudinal axis A of the pump in the pumping manifold. As the cam rotates 147 around the axis R, the bearing 158 of the spool coupler 156 travels along the cam surface 149. The cam surface 149 has a geometry that causes the cam follower 153 to move up along the axis R of the cam shaft 151 as the bearing 158 travels along the cam surface 149 during cam 147 rotation. The bushing 154 of the cam follower 153 moves up the cam shaft 151 and the spool coupler 156 drives the pumping system 160 in a first direction. A cam follower return spring 152 can be positioned around the cam shaft 151 to urge the bushing 154 of the cam follower 153 towards the cam surface 149. As the cam 147 rotates further and the cam surface 149 angles back downward, the spring 152 urges the bushing 154 of the of the cam follower 153 back down the cam shaft 151 and the spool coupler 156 drives the pumping system 160 in a second, opposite direction. The pumping system 160 will be described in more detail below.

Figure 3:
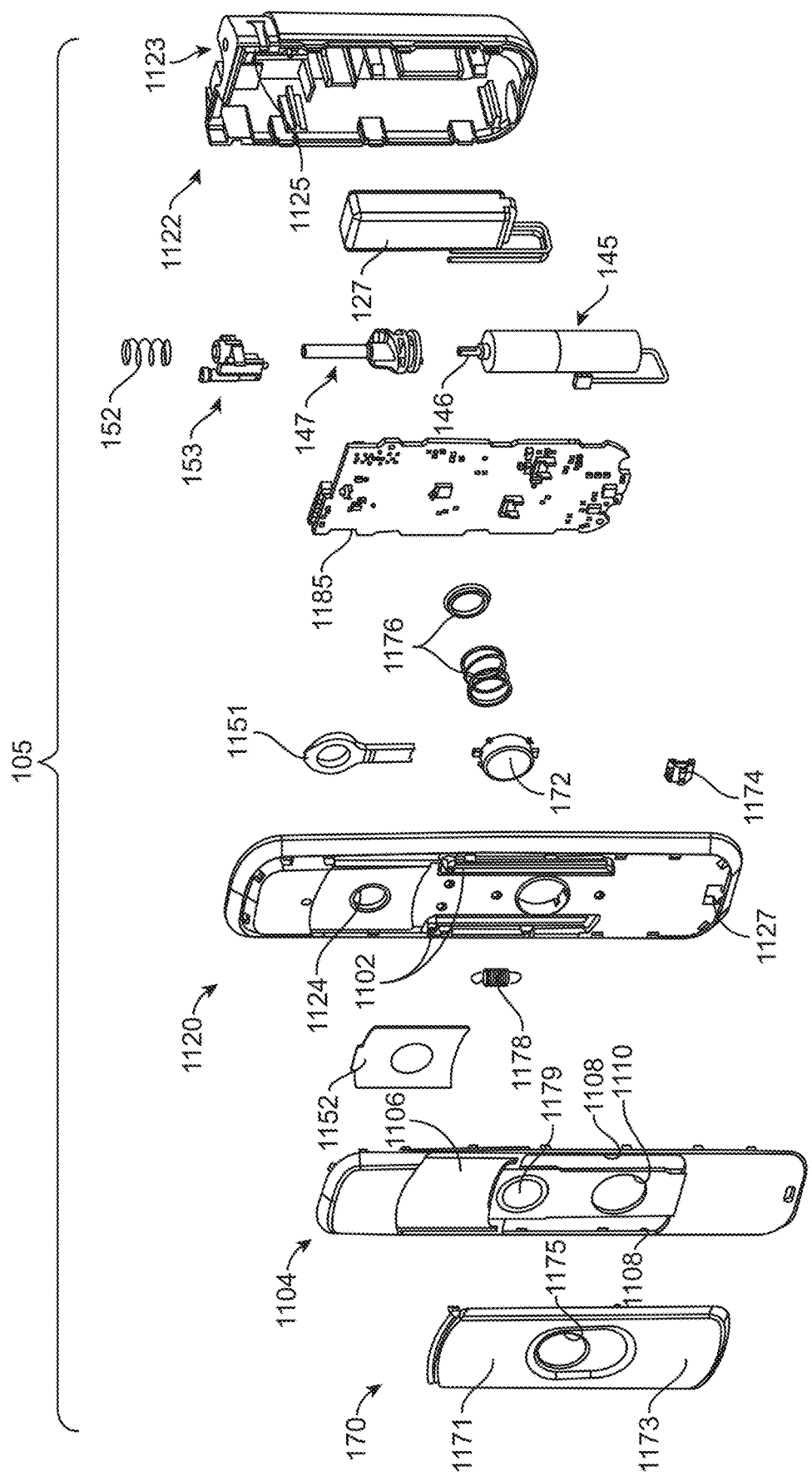
FIG. 3 is an exploded view of the base device of FIG. 2A.

FIG. 3 is an exploded view of the base device 105 showing the housing 112 can be divided into a front shell 1120 and a back shell 1122 that upon coupling to one another substantially enclose the components of the base device 105, including the drive system 120 and other electronic components discussed above mounted to a printed circuit board (PCB) 1185. An indicator aperture 1127 can be positioned to receive the indicator light 1174.

The front shell 1120 can slideably couple with the shutter 170. An outer surface of the front shell 1120 can include a pair of shutter tracks 1102 configured to couple with corresponding features on an inner surface of the shutter 170. A shutter fascia 1104 can be positioned between the shutter 170 and the front shell 1120. The shutter tracks 1102 can insert through a pair of corresponding slots 1108 on the shutter fascia 1104 in order to connect with the shutter 170.

The front shell 1120 can include at least two apertures extending through it. An upper aperture 1124 can allow for delivery of fluid from the ejector system 180 to the patient. A lower aperture 1126 can receive the dose button 172 therethrough. The shutter fascia 1104 can also include an upper opening 1106 configured to align with the upper aperture 1124 of the front shell 1120 and a lower opening 1110 configured to align with the lower aperture 1126 of the front shell 1120. The aligned upper opening 1106 and upper aperture 1126 form the spray aperture 118 and the aligned lower opening 1110 and lower aperture 1126 are sized to receive the dose button 172.

The shutter 170 is configured slide along the shutter tracks 1102 of the front shell 1120 between a resting (closed) position and an active (open) position. The spray aperture 118 and the dose button 172 are covered by the shutter 170 when the shutter 170 is in the resting position. The spray aperture 118 and the dose button 172 are revealed by the shutter 170 when the shutter 170 is in the active position. The shutter 170 can include a central dose button opening 1175 positioned between an upper portion 1171 of the shutter 170 and a lower portion 1173 of the shutter 170. When in the resting position (see FIG. 2B), the shutter 170 is arranged relative to the fascia 1104 and the front shell 1120 so that the upper portion 1171 of the shutter 170 covers the spray aperture 118 (i.e. the upper opening 1106 aligned with the upper aperture 1124). Additionally, the lower portion 1173 of the shutter 170 covers the dose button 172 extending through the lower opening 1110 aligned with the lower aperture 1126. When the shutter 170 is urged into the active position (see FIG. 2C), the shutter 170 is urged downwards relative to the shutter fascia 1104 and the front shell 1120 so that the upper portion 1171 of the shutter 170 slides below the spray aperture 118 (i.e. the upper opening 1106 aligned with the upper aperture 1124). The dose button opening 1175 of the shutter 170 aligns with the lower opening 1106 and the lower aperture 1126 thus, revealing the dose button 172.

The dose button 172 can be engaged with a spring 1176 that biases the dose button 172 outwards relative to the front shell 1120. Additionally, the shutter 170 can be engaged with a spring element 1178 on the shutter fascia 1104 configured to bias the shutter 170 upwards in the resting position. As an example, the shutter 170 can be manually urged by a user into the active position (e.g. downward relative to the front shell 1120). The spring element 1178 upon sliding the shutter 170 downwards can be stretched or compressed depending on the configuration thereby storing energy. The dose button 172 is revealed through the aligned openings (i.e. 1175, 1110, and 1126). The presence of the dose button 172 extending through the aligned openings maintains the shutter 170 in this active position. Pressing the dose button 172 can release the shutter 170 from the active position releasing the stored energy of the spring element 1178 to urge the shutter 170 back up to the resting position. The shutter fascia 1104 or another portion of the base device housing can include a retention feature 1179 configured to retain the shutter 170 in a closed position thereby preventing inadvertent sliding into the active position. As an example, the retention feature 1179 can be a protrusion corresponding in shape to the dose button aperture 1175 of the shutter 170 to thereby extend through the aperture 1175 when the shutter 170 is urged upwards relative to the fascia 1104. Other configurations are considered herein. The shutter release need not be a function of the depression of a button. For example, the motor cam can automatically release the shutter 170 at the end of its rotation.

Actuating the shutter 170 and dose button 172 can be performed with a single hand. A user can, for example, manipulate the shutter 170 and/or dose button 172 with one or more digits while holding the base device 105 in the one hand. The base device 105 can be held such that the spray aperture is aimed in a manner to provide horizontal delivery to a user's eye.

Sliding the shutter 170 to the lowered position not only reveals the dose button 172 and the spray aperture, but also electronically "wakes" the base device 105 such that pressing the dose button 172 can initiate the pump/spray sequence as will be described in more detail below. The shutter 170 and/or the dose button 172 can interact with one or more sensors that communicate with the control processor 130 and wake the base device 105. In an implementation, fully lowering the shutter 170 allows the dose button 172 to move outward away from the PCB 1185. This lifting of the dose button 172 away from a button switch on the PCB 1185 sends a signal to the control processor 130 that the shutter 170 has lowered and the dose button 172 is ready to be depressed. In another implementation, the shutter 170 in the fully lowered position may engage with a switch or sensor that wakes the base device 105.

Cartridge

As discussed above, the cartridge 110 may be a reversibly removable and interchangeable element that can be engaged with the base device 105 that is configured to come into direct contact with the fluids to be delivered. Again with respect to FIG. 1, the cartridge 110 can include the housing 114 configured to substantially enclose a fluid container 155, a pumping system 160, and an ejector system 180. The fluid container 155 can be a non-evaporative primary drug container filled with a liquid medicament to be delivered to a user in droplet form. The pumping system 160 is arranged to draw discrete volumes or doses of medicament from the fluid container and deliver those doses to the ejector system 180. The ejector system 180 can be a piezoelectric ejector system configured to deliver the dose of medicament drawn by the pumping system from the fluid container in the form of microdroplets. Each of these components will be described in more detail below.

Figure 4:
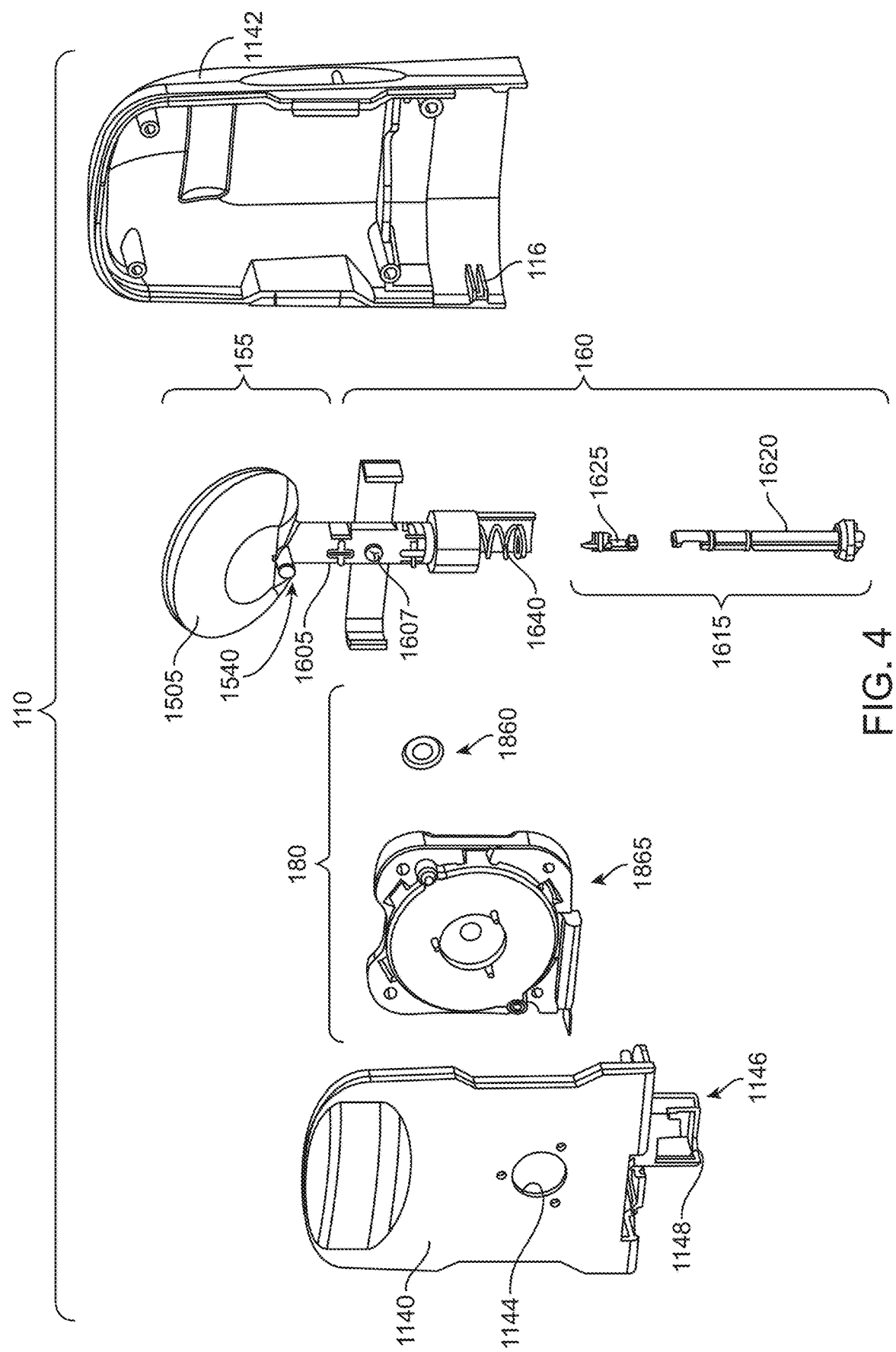
FIG. 4 is an exploded view of the cartridge of FIG. 2A.

FIG. 4 is an exploded view of the cartridge 110 showing the housing 114 formed of a relatively rigid, lightweight material(s) that can be divided into a front shell 1140 and a back shell 1142 and upon coupling to one another substantially enclose the fluid container 155, the pumping system 160, and the ejector system 180 within an inner chamber of the housing. The housing 114 need not fully enclose all the components of the cartridge 110 such that mating between respective components in the cartridge 110 and base device 105 is possible. For example, at least a portion of the pumping system 160 of the cartridge 110 can remain available outside the cartridge 110 housing 114 such that at least a portion of the drive system 120 of the base device 105 can operatively engage with the pumping system 160. As another example, the front shell 1140 of the housing 114 of the cartridge 110 can include a spray aperture 1144 extending through it. When the cartridge 110 is installed on the base device 105, the drive system 120 of the base device 105 can operatively engage with the pumping system 160 of the cartridge 110 and spray aperture 1144 of the front shell 1140 can align with the spray aperture 118 of the base device 105 so as to deliver fluid to the patient.

As discussed above, the arrangement of attachment between the cartridge 110 and the base device 105 can vary. In some implementations, the cartridge 110 and the base device 105 can be coupled in an orientation relative to the user where the cartridge 110 is positioned on an upper end region of the base device 105. A rear-facing surface of the base device 105 front shell 1120 and an upper-facing surface of the base device 105 rear shell 1122 can form a the corresponding slot 113 configured to receive the housing 114 of the cartridge 110 thereby creating a singular housing for the system 100. In this arrangement, a front-facing surface of the cartridge 110 front shell 1140 aligns with and abuts against the rear-facing surface of the base device 105 front shell 1120 and a lower-facing surface of the cartridge 110 front shell 1140 reversibly engages with the upper-facing surface of the base device 105 rear shell 1122.

The cartridge 110 and base device 105 can couple together using a variety of attachment and alignment mechanisms 116 such as snap-lock, bayonet, or other type of reversible coupling. As an example, the lower-facing surface of the cartridge 110 front shell 1144 can incorporate a projection 1146 configured to insert within a corresponding slot 1123 in the upper-facing surface of the base device 105 back shell 1122. The projection 1146 can mechanically link with the slot 1123 to prevent inadvertent removal of the cartridge 110 from the base device 105. The projection 1146 and slot 1123 can also incorporate corresponding windows 1148, 1125 defined therethrough. The window 1148 in the projection 1146 allows for a lower end of the pumping system 160 in the cartridge 110 to be available for coupling with a portion of the drive system 120 in the base device 105 made available through the window 1125 in the slot 1123.

The coupling between the cartridge 110 and the base device 105 can include a release button configured to uncouple the cartridge 110 from the base device 105. The coupling between the cartridge 110 and base device 105 may be purely mechanical or may involve both mechanical and electronic couplings. For example, the cartridge 110 may incorporate an electronic input configured to electronically couple with a portion of the base device 105.

Fluid Container

Figure 5:
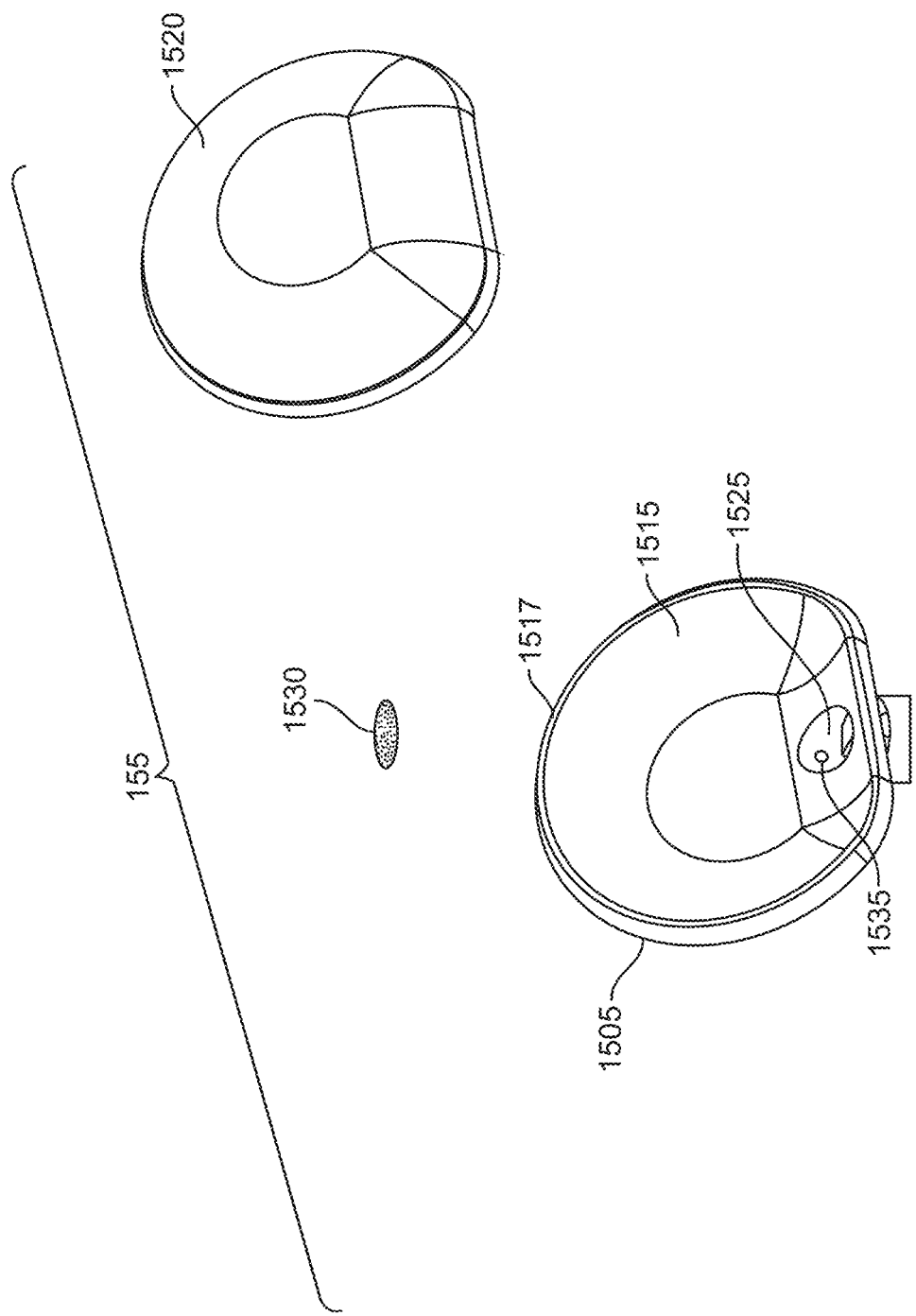
FIG. 5 is an exploded partial view of a fluid container of FIG. 4.

FIG. 5 is an exploded, partial view showing the fluid container 155 of the cartridge 110 to be filled with a medicament for delivery. Any liquid medicament for ophthalmic delivery may be contained within the fluid container 155. Therapeutic agents considered herein are described in more detail below as well as in U.S. Publication No. 20170344714, which is incorporated herein by reference.

The fluid container 155 can have any suitable shape and size configured for receiving liquid medicament. Generally, the fluid container 155 is sized large enough to contain multiple doses. The fluid container 155 can be rigid walled or expandable. In some implementations, an interior volume of the fluid container 155 (in a fully expanded state) is about 1 ml to about 10 ml, more specifically, about 3 ml to about 5 ml, or about 2.5 ml to about 3.0 ml. The volume of the fluid container 155 can be at least 150 times the volume of a capacity of the ejector system 180.

The fluid container 155 can include a reservoir manifold 1505 coupled on a lower end region to a pumping manifold 1605. The reservoir manifold 1505 defines, in part, a reservoir 1510 for containing the medicament and the pumping manifold 1605 defines an inner bore containing a pump 1615 configured to draw and eject doses medicament from the fluid container 155.

The fluid container 155 can include an expandable reservoir. In an implementation, the expandable reservoir is formed, in part, by a relatively rigid reservoir manifold 1505 coupled to a movable reservoir film 1520. The reservoir manifold 1505 can have a concave inner surface 1515 and a mating edge 1517 at an outer perimeter of the concave inner surface 1515. The edge 1517 is configured to mate with a corresponding outer perimeter of the collapsible reservoir film 1520. The reservoir film 1520 tents outward or collapses inward depending on how much fluid is contained within the reservoir 1510. Filling the reservoir 1510 with a liquid can cause the reservoir film 1520 to tent, expand, enlarge, or otherwise move outwards away from the reservoir manifold 1505. As the liquid in the reservoir 1510 is consumed, the reservoir film 1520 may suck back down towards the reservoir manifold 1505 (see FIG. 6A-6B). The reservoir film 1520 may be expandable and collapsible such that it moves relative to the reservoir manifold 1505, but is generally not elastic or stretchy. The reservoir film 1520 of the fluid container 155 means that no venting is necessary during use. The collapse of the reservoir film 1520 towards the manifold 1505 is what makes up for the volume of drug removed from the container during each cycle. It should be appreciated, however, that the system may include venting in the manifold 1505 to allow air to escape upon insertion of the spools into the pumping manifold 1605. This venting can aid in eliminating any air bubbles from entering the drug reservoir 1510 upon a first actuation of the device following loading of the cartridge. As an example, venting of the reservoir 1510 can be accomplished via a one-way valve allowing air to escape the reservoir 1510, but not enter the reservoir 1510.

Again with respect to FIG. 5, the lower end region of the reservoir manifold 1505 can include an exit port 1525. A manifold film 1530 can sit within the exit port 1525 of the reservoir manifold 1505 to isolate the interior of the reservoir 1510 from the interior of the pumping manifold 1605. The reservoir 1510 is thus, defined collectively by the reservoir manifold 1505, the reservoir film 1520, and the manifold film 1530. The reservoir film 1520 can have substantially similar outer dimension as the reservoir manifold 1505 such that an edge of the reservoir film 1520 can mate with the edge 1517 of the manifold 1505. The manifold film 1530, in contrast, can have a relatively small dimension such that it can sit within the exit port 1525. Both the manifold film 1530 and the reservoir film 1520 feature very low vapor transmission rates to prevent drug evaporation prior to, and during product use.

The reservoir film 1520 can be a collapsible membrane having a thickness of about 0.001 inch to about 0.030 inch, more specifically about 0.002 inch to about 0.004 inch. The material of the reservoir film 1520 can vary, but is generally a flexible, non-permeable material with good vapor barrier. In some implementations, the reservoir film 1520 can be made from polymers such as PET, SiO, linear low density polyethylene or the like. In some implementations, the reservoir film 1520 is a metalized plastic film or foil suitable for drug containment including flexible aluminum foil/Polyolefin film.

The manifold film 1530 can be the same material have the same material properties as the reservoir film 1520, however the manifold film 1530 may also be a different material as the reservoir film 1520. The materials of the reservoir manifold 1505 and reservoir film 1520 may be selected based on their biocompatibility, stability, sterility, and whether or not they are extractable/leachable.

In some implementations, the reservoir manifold 1505 is formed of plastic that is highly stable and suitable for drug fluid interaction, including cyclic olefin copolymer (COC). The reservoir film 1520 and the manifold film 1530 may be heat-welded onto the reservoir manifold 1505.

The fluid container 155 can be sterilized and/or sterile-filled via a sterilization port, a fill port, or a single universal port. In some implementations, the fluid container 155 can incorporate a fill port 1535 located near the lower end region of the reservoir manifold 1505, for example, positioned above the manifold film 1530. The fill port 1535 can be penetrated by a needle or similar tool configured to inject fluid into the reservoir 1510 without damaging the film 1520. The fill port 1535 can be sealed by one of, but not limited to, a plug, heat cut/seal, or other sealing element 1540. In some implementations, the fluid container 155 can include more than a single port. For example, a first port can be configured for filling the fluid container 155 and a second port can be configured for venting such as for airing out the fluid container 155 following sterilization. This sort of configuration may be referred for VHP (vaporized hydrogen peroxide) sterilization method. Generally, the reservoir 1510 is not intended to be refilled after use and instead disposed of However, such a configuration is well within the scope of what is described and considered herein.

Pumping System

Figure 6A:
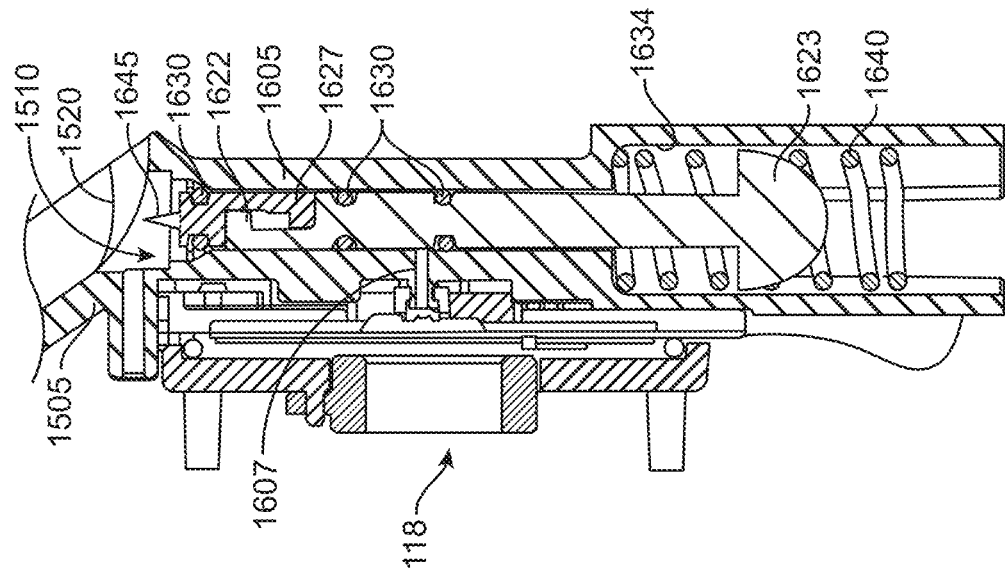
FIGS. 6A and 6B are cross-sectional, partial side views of a cartridge without a housing showing the pump in different pumping stages.
Figure 6B:
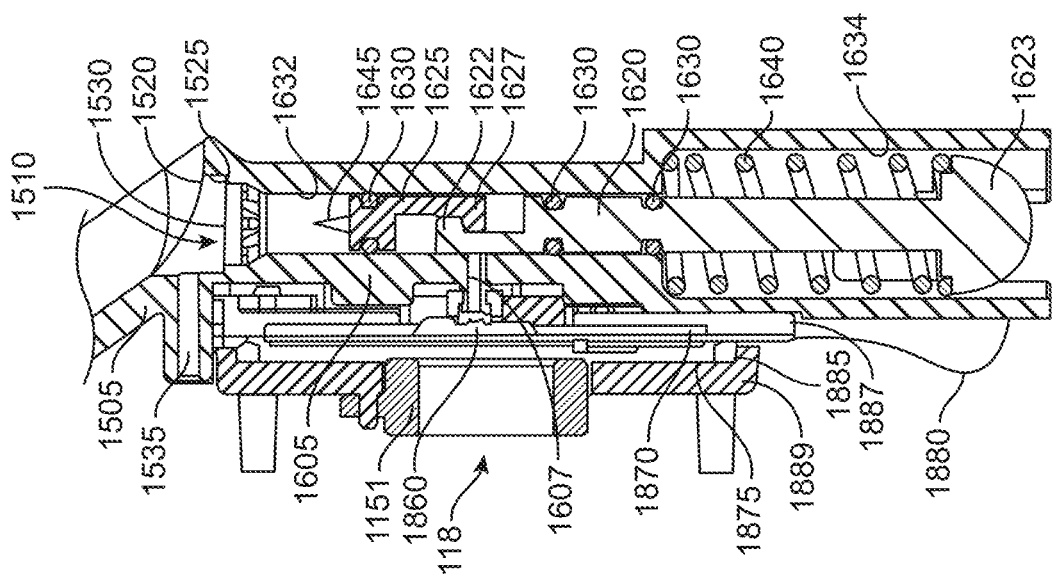
Figure 7:
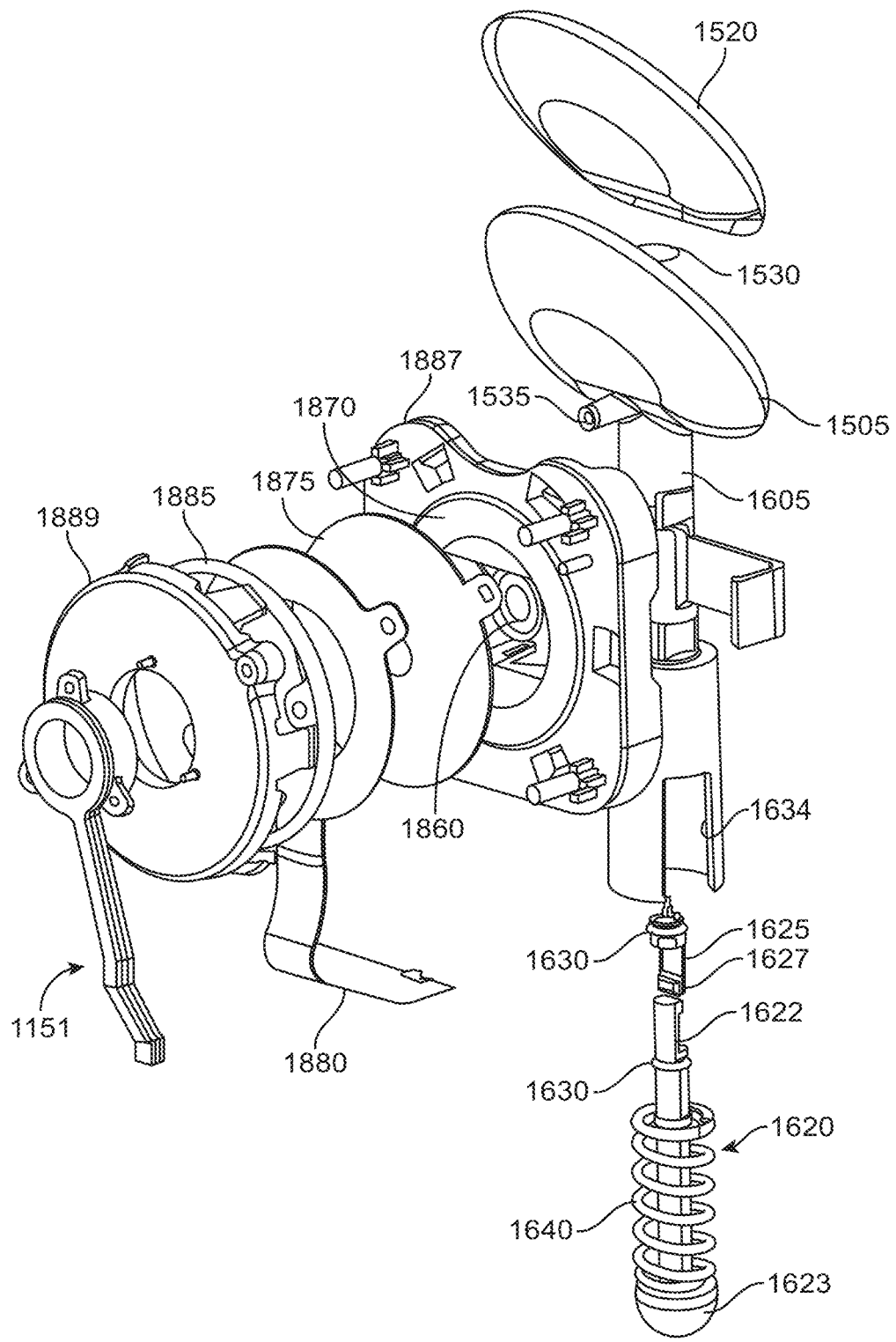
FIG. 7 is an exploded view of a cartridge without a housing.

FIGS. 6A-6B show a cross-sectional partial views and FIG. 7 shows an exploded, partial view of the cartridge 110 without the housing. The fluid container 155 can be positioned relative to the pumping system 160 such that the pumping system 160 can draw discrete volumes or doses of fluid from the reservoir 1510 and deliver those doses to the ejector system 180. As mentioned above, the pumping manifold 1605 defines an inner bore sized to contain the pump 1615. The pumping manifold 1605 can be an extension of or coupled to the reservoir manifold 1505 of the fluid container 155.

The pump 1615 can be a two-part, positive displacement pump where a first part of the pump 1615 can be moveably coupled to a second part of the pump 1615. In an implementation, the first part can be a drive spool 1620 that is actively driven by the drive system 120 of the base device 105 to reciprocate the drive spool 1620 within the pumping manifold 1605. For example, the drive spool 1620 can be operatively coupled to an electric motor of the drive system 120. The second part can be a passive, floating spool 1625 moveably coupled or engaged with the drive spool 1620. The floating spool 1625 can also reciprocate through the pumping manifold 1605, but it reciprocates in response to drive spool movement. As best shown in FIGS. 6A-6B, the drive spool 1620 can include a main body 1621 having an extension 1622 at an upper end region of the main body 1621 and a piston head 1623 at a lower end region of the main body 1621. The extension 1622 on the drive spool 1620 can extend toward and interlock with a corresponding extension 1627 of the floating spool 1625. The piston head 1623 on the drive spool 1620 can operatively engage with at least a portion of the drive system 120 (e.g. the rotary cam 147 via a cam follower 153, etc.). The drive spool 1620 is driven by the drive system 120 and, in turn, drives the floating spool 1625 through the pumping cycles via engagement of the extensions with one another.

Two sliding seals 1630, such as O-rings or quad-rings, can encircle the main body of the drive spool 1620. The floating spool 1625 can include one sliding seal 1630 encircling a portion near an upper end of the floating spool 1625. A cavity or space can be formed between the spools 1620, 1625 with the size of that space changing as the spools 1620, 1625 move toward and away from one another. Increasing the size of the space by separating the spools 1620, 1625 away from one another draws fluid from the reservoir 1510 into this space (see FIG. 6A). Decreasing the size of the space by urging the spools 1620, 1625 towards one another ejects fluid from the space into the ejector system 180 (see FIG. 6B).

The space separating the spools 1620, 1625 can have a volume commensurate with the dose volume of the fluid being drawn and delivered. A volume of an aliquot or dose of fluid dispensed by a complete and full dispense cycle of the spools 1620, 1625 may be approximately equal to the cross-sectional area of the pumping manifold 1605 bore multiplied by the length of displacement of the two spools 1620, 1625 and excluding the volume of the engagement ends of the spools 1620, 1625. The maximum axial displacement between the drive spool 1620 and the floating spool 1625 may be about 0.100 inch to about 0.300 inch, or from about 0.100 inch to about 0.130 inch. A complete aliquot of fluid may be dispensed. The dose volume of fluid dispensed by a full cycle can be between 2 ul and 15 ul or between 5 ul and 9 ul. The dose volume can be smaller or can be larger than this range, but is within a micro-volume range. The dose volume delivered can also be adjustable such as via programming of the control processor. The dose volume approximates the physiologic tear film capacity, which maximizes the effective dose while minimizing the likelihood that the patient will blink out excess solution greater than the tear volume.

Each of the spools 1620, 1625 may be made from any suitable material or materials including polymers or plastics such as polycarbonate, PEEK, thermoplastics, cyclic olefin copolymer, and the like. The floating spool 1625 can be made of medical grade cyclic olefin copolymer (COC) that features low permittivity to prevent the drug from evaporating through the spool. The driven spool 1620 need not act as a vapor barrier, but is in contact with the drug and thus, should be a medical grade plastic such as Acrylonitrile butadiene styrene (ABS) or other medical grade plastic. The sliding seals 1630 on the spools 1620, 1625 may be formed of materials such as butyl, silicone, polyurethanes, or the like. It should be appreciated that the sliding seals 1630 can have any of a variety of configurations including O-ring, quad ring, and the like. The upper-most sliding seal 1630 (i.e. the seal on the floating spool 1625) protects the drug from leaking/evaporating out of the reservoir 1510. Additionally, the sliding seal 1630 on the floating spool 1625 remains above the ejector system 180 (e.g. above the channel 1607 shown in FIGS. 6A-6B) during all stages of pumping. This ensures the reservoir 1510 remains sealed from ambient air.

The single sliding seal 1630 on the floating spool 1625 together with the upper sliding seal 1630 on the drive spool 1620 can seal the space between the spools 1620, 1625 so that the fluid drawn into the pumping manifold 1605 from the reservoir 1510 is maintained within the space so it can be delivered to the ejection system 180. The single sliding seal 1630 on the floating spool 1625 also aids in ensuring relative movement between the two spools 1620, 1625 occurs. When the floating spool 1625 is engaged with the drive spool 1620, sliding motion of the drive spool 1620 causes sliding motion of the floating spool 1625. When the floating spool 1625 is not engaged with the drive spool 1620, sliding motion of the drive spool 1620 does not cause sliding motion of the floating spool 1625 because the sliding seal 1630 on the floating spool 1625 provides enough friction to maintain the floating spool 1625 in place within the pumping manifold 1605 as the drive spool 1620 moves. Thus, the sliding seal 1630 of the floating spool 1625 is capable of translating through the pumping manifold 1605, but also provides sufficient interaction with the wall of the pumping manifold 1605 to prevent fluid passage and also to remain in place within the pumping manifold 1605 when the floating spool 1625 is not engaged with and driving the drive spool 1620 through the pumping manifold 1605.

Still with respect to FIGS. 6A-6B, the pumping manifold 1605 can be divided into two portions, including a pumping chamber 1632 and a piston chamber 1634. The pumping chamber 1632 can be in an upper region of the pumping manifold 1605 near where it couples with the reservoir manifold 1505. The exit port 1535 of the reservoir manifold 1505 can be separated from the pumping chamber 1632 by the manifold film 1530. The piston chamber 1634 can be in a lower region of the pumping manifold 1605 near where the drive spool 1620 couples with the drive system 120. The lower sliding seal 1630 on the drive spool 1620 can seal the pumping chamber 1632 from the piston chamber 1634.

The pumping chamber 1632 can have a substantially round transverse cross-section configured to receive at least a portion of the drive spool 1620 and the floating spool 1625. The spools 1620, 1625, in turn, may also have a substantially round transverse cross section and are slidingly disposed within the pumping chamber 1632.

The piston chamber 1634 can also have a substantially round transverse cross-section configured to receive a return spring 1640. The return spring 1640 can be positioned within the piston chamber 1634 such that the return spring 1640 surrounds the portion of the drive spool 1620 extending through the piston chamber 1634. A lower end of the return spring 1640 can abut against the piston head 1623 of the drive spool 1620 and an upper end of the return spring 1640 can abut against an upper end of the piston chamber 1634. The return spring 1640 can be biased to urge the piston head 1623 of the drive spool 1620 towards a lower end of the piston chamber 1634 (see FIG. 6A). As the drive spool 1620 is urged by the drive mechanism 120 upward towards the fluid container 155, the return spring 1640 within the piston chamber 1634 gets compressed between the piston head 1623 and an upper end surface of the piston chamber 1634 (see FIG. 6B).

The pump is shown in FIGS. 6A and 6B in two different stages of pumping. FIG. 6A shows the drive spool 1620 urged by the return spring 1640 towards a lower end of the piston chamber 1634. The extension 1622 of the drive spool 1620 is engaged with the extension 1627 of the floating spool 1625 thereby pulling the floating spool 1625 downwards through the pumping chamber 1632 away from the fluid container 155. The space between the drive spool 1620 and the floating spool 1625 in this configuration is at its maximum size. The sliding seal 1630 of the floating spool 1625 and the upper sliding seal 1630 of the drive spool 1620 are shown sealing the space between the drive spool 1620 and the floating spool 1625 such that the space is in fluid communication with the ejector system 180 via a channel 1607 extending through the pumping manifold 1605 leading to the ejector system 180. FIG. 6B shows the drive spool 1620 urged upwards through the pumping chamber 1632. The space between the drive spool 1620 and the floating spool 1625 has collapsed. The drive spool 1620 has traveled back upwards through the pumping chamber 1632 until the upper and lower sliding seals 1630 of the drive spool 1620 are positioned on either side of the channel 1607. The floating spool 1625 is urged upwards by the drive spool 1620 towards the fluid container 155.

Use of directional terms such as "upward" and "upper" or "downward" and "lower" are intended to provide clarity with respect to what is shown in the drawings and are not intended to be limiting. Other configurations of the cartridge 110 and base device 105 are considered herein such that motion of the spools 1620, 1625 relative to the pumping manifold 160 is in a different orientation. For example, motion of the spools 1620, 1625 to draw fluid from the reservoir 1510 and eject fluid from the pumping manifold 160 can be reversed such that downward motion causes the spool 1625 to penetrate the manifold film 1530 and upward motion aligns the fluid with the ejector system 180 for ejection. Side-to-side motions of the pump portions are also considered herein.

An upper surface of the floating spool 1625 (i.e. above the sliding seal 1630) can include a projection 1645 (see FIGS. 6C, 6E, and 6F). The projection 1645 can be a spike having a cutting edge geometry configured to penetrate the manifold film 1530. In some implementations, the projection 1645 can be a needle stylet having a tip with a variety of geometries including bevel tip, lancet point, back bevel, trocar tip, conical tip, diamond, or other geometry configured to cut or puncture the film when advanced through it. The projection 1645 need not penetrate the manifold film 1530 to place the inside of the reservoir 1510 in fluid communication with the pump. The projection 1645 can lift the film 1530 away from its sealing surface with the exit port 1525 such that the foil 1530 remains lifted into an open position. In still other implementations, the projection 1645 may penetrate or lift the foil 1530 relative to the exit port 1525 only when the projection 1645 is positioned in its upward-most position such that the reservoir 1510 reseals when the projection 1645 retracts away from the exit port 1525. Where the projection 1645 is described herein as penetrating the manifold film 1530 it should be appreciated that the film 1530 need not be punctured and can be lifted or otherwise moved away from the exit port 1525 creating an open pathway.

The floating spool 1625 can be driven upwards until the projection 1645 on the upper end of the floating spool 1625 penetrates the manifold film 1530 in the exit port 1525 of the reservoir manifold 1505. The geometry of the projection 1645 can ensure that upon penetration of the film 1530, fluid within the reservoir 1510 can pass through the penetration location. Thus, the geometry of the projection 1645 preferably allowed for fluid to pass around the projection 1645 even while the projection 1645 is positioned within the reservoir 1510. Thus, motion of the floating spool 1625 upward through the pumping manifold 1605 into the inlet location directly results in penetration of the film 1530 and placing the reservoir 1510 into fluid communication with the pumping manifold 1605. The floating spool 1625 projection 1645 is removed from the reservoir film 1530 when the floating spool 1625 travels back down through the pumping manifold 1605 to deliver the drawn-down discrete dose to the ejector system 180. The seal 1630 on the floating spool 1625 maintains a seal against the wall of the pumping manifold 1605 during this downward travel towards the ejector system 180 and ensures the region of the pumping manifold 1605 above the seal 1630 on the floating spool 1625 is sealed from the region of the pumping manifold 1605 below the seal 1630. Once the floating spool 1625 is urged back to the upward-most position within the pumping manifold 1605, the floating spool 1625 is positioned again relative to the reservoir 1510 so that fluid from the reservoir 1510 communicates with the region of the pumping manifold 1605 below the seal 1630.

Puncturing the manifold film 1530 with the projection 1645 on the floating spool 1625 can allow the fluid to flow from the reservoir 1510 to the wetted path of the pumping manifold 160. FIG. 6C shows a close-up view of the projection 1645 penetrating through the manifold film 1530. This configuration places the pumping manifold 160 into fluid communication with the reservoir 1510. As mentioned previously, the reservoir manifold 1505 includes an exit port 1525 within which the manifold film 1530 sits such that the manifold film 1530 isolates the reservoir 1510 from the pumping chamber 1632 of the pumping manifold 160. FIG. 6D is a downward view of the exit port 1525 from the reservoir 1510 with the manifold film 1530 and floating spool 1625 removed leaving the sliding seal 1630 in position within the pumping chamber 1632. An upper inlet region of the pumping chamber 1632 is positioned below the exit port 1525 where the manifold film 1530 is normally positioned. FIG. 6C shows the inlet region of the pumping chamber 1632 can taper from a larger inner diameter of the exit port 1525 to a smaller inner diameter of the pumping chamber 1632 in the inner bore. The tapered inlet region of the pumping chamber 1632 can have a plurality of surface features configured to ensure fluid communication between the reservoir 1510 and the pumping chamber 1632 when the projection 1645 penetrates the manifold film 1530. The surface features can vary. In an implementation, the surface features include a plurality of peaks 1650 and valleys 1655. The valleys 1655 prevent complete sealing between the sliding seal 1630 of the floating spool 1625 with the walls of the tapered inlet region of the pumping chamber 1632. The plurality of valleys 1655 together with the geometry of the projection 1645 allow for fluid in the reservoir 1510 to pass around the projection 1645 and around the sliding seal 1630 of the floating spool 1625 into the pumping chamber 1632 when the floating spool 1625 penetrates the manifold film

1530. The fluid is drawn into the pumping chamber 1632 due to the retraction of the drive spool 1620 and the vacuum created within the pumping chamber 1632 as the space between the drive spool 1620 and the floating spool 1625 increases. Additionally, the reservoir 1510 can be positioned above the variable volume pumping chamber 1632.

As mentioned above, the projection 1645 of the floating spool 1625 can have a variety of geometries configured to puncture the manifold film 1630 sealing the reservoir 1510 from the pumping chamber 1632. The position of the projection 1645 on the upper end of the floating spool 1625 can vary as well. The projection 1645 shown in FIG. 6C is positioned relatively central on the upper surface of the floating spool 1625. FIG. 6E shows the upper end of the floating spool 1625 relative to the inlet region of the pumping chamber 1632 and FIG. 6F is a perspective view of a floating spool 1625 incorporating a projection 1645 and sliding seal 1630. The projection 1645 shown in these figures is eccentric or off-set from the central axis of the spool 1625. The projection 1645 can taper to a sharp tip at the perimeter of the floating spool 1625 such that the longest portion of the projection 1645 is positioned the furthest away from the central axis of the spool 1625. The eccentric positioning of the projection 1645 relative to the upper surface of the spool 1625 as well as the tapering towards the outer edges or perimeter aids in preventing inadvertent penetration or snagging on the reservoir film 1520, which is not intended to be punctured by the pump and could cause leakage of the reservoir 1510. FIG. 6E shows the exit port 1525 in the reservoir manifold 1505. The reservoir manifold 1505 can slope downwards towards the exit port 1525 such that as the reservoir 1510 empties the liquid in the reservoir 1510 collects towards the exit port 1525. The floating spool 1625 is positioned within the pumping chamber 1632 of the pumping manifold 1605 so that the eccentric projection 1645 on the upper surface of the floating spool 1625 is positioned away from the edge 1517 where the reservoir manifold 1505 seals with the reservoir film 1520 and towards the fill port 1535. FIG. 6E shows the eccentric projection 1645 positioned between a first peak 1650*a* and a second peak 1650*b* in the inlet region of the pumping chamber 1632 such that the projection 1645 is substantially aligned with the valley 1655 between them. The taper of the projection 1645 ensure the longest part of the projection 1645 is located towards in the inner wall of the inlet region. This positioning provides the greatest clearance between the tip of the projection 1645 and the reservoir film (not shown in FIG. 6E).

Still with respect to FIGS. 6C, 6E, and 6F, the sliding seal 1630 of the floating spool 1625 can be positioned within a corresponding gland 1633 near an upper end of the floating spool 1625. The sliding seal 1630 can be an elastomeric O-ring or similar toroid-shaped component configured to compress between the walls of the pumping chamber 1632 and the gland 1633 to effectively block flow of any fluid past the seal 1630. This sealing occurs when the floating spool 1625 is positioned within the pumping chamber 1632 and the sliding seal 1630 is compressed between the walls of the pumping chamber 1632 and the gland 1633 of the floating spool 1625. At its upper end of travel, however, the sliding seal 1630 of the floating spool 1625 enters into the tapered inlet region of the pumping chamber 1632. The sliding seal 1630 is no longer able to create a complete seal with the walls of the inlet region and the complete seal breaks. The inlet region tapers to a larger inner diameter compared to the inner diameter of the pumping chamber 1632. Also, the inlet region includes the valleys 1655 between the peaks 1650 that allow liquid from the reservoir 1510 to flow past the sliding seal 1630 into the pumping chamber 1632. The upper sliding seal 1630 of the drive spool 1620 remains sealed within the pumping chamber 1632 thereby preventing the fluid from the reservoir 1510 from traveling past that sealing point.

The wetted delivery flow path can extend from the lower end of the reservoir 1510 where the projection 1645 penetrates the manifold film 1530 through the bore of the pumping chamber 1632 to the channel 1607 leading to the ejector system 180. The delivery flow path of the cartridge 110 is a relatively simple and short flow path with few connections. This mitigates problems with air and fluid leaks. Because the delivery flow path is short, the dormant drug (drug between doses) is exposed to less surface area and has less chance to evaporate compared to a longer delivery flow path with larger surface area. A length of the delivery flow path between the reservoir 1510 and the ejector system 180 can be between about 0.5 inch and 1.0 inch, or roughly about 0.6". In an implementation, the delivery flow path of the cartridge 110 can be a generally L-shaped path that is about 0.44 inch down and about 0.15" horizontal from the inlet to the pumping chamber 1632 to the channel 1607 leading to the ejector system 180.

The fluid may be delivered from the space between the spools at a relatively high velocity of at least about 0.5 meters/second (or with the pump delivering the fluid at a pressure of at least about 200 psi) to "fire" the droplet into the ejector system 180.

As discussed above, the pump/spray sequence can be controlled by the drive system 120, which can include a motor-driven rotary cam 147. The drive spool 1625 of the pumping system 160 can connect with the cam surface 149 of the rotary cam 147 directly or indirectly via a coupler. For example, the cam follower 153 (see FIGS. 8A-8C) can be positioned between the rotary cam 147 and the drive spool 1620 of the pumping system 160. The piston head 1623 of the drive spool 1620 can be received within the recess of the spool coupler 156 on the cam follower 153, as described above, such that upon rotation of the cam 147 the drive spool 1620 moves with the cam follower 153 to various positions within the pumping chamber 1623. The reciprocal, linear motion of the drive spool 1620 can draw a dose of fluid from the reservoir 1510 into the pumping chamber 1623 to deliver the dose to the ejector system 180.

Figure 9:
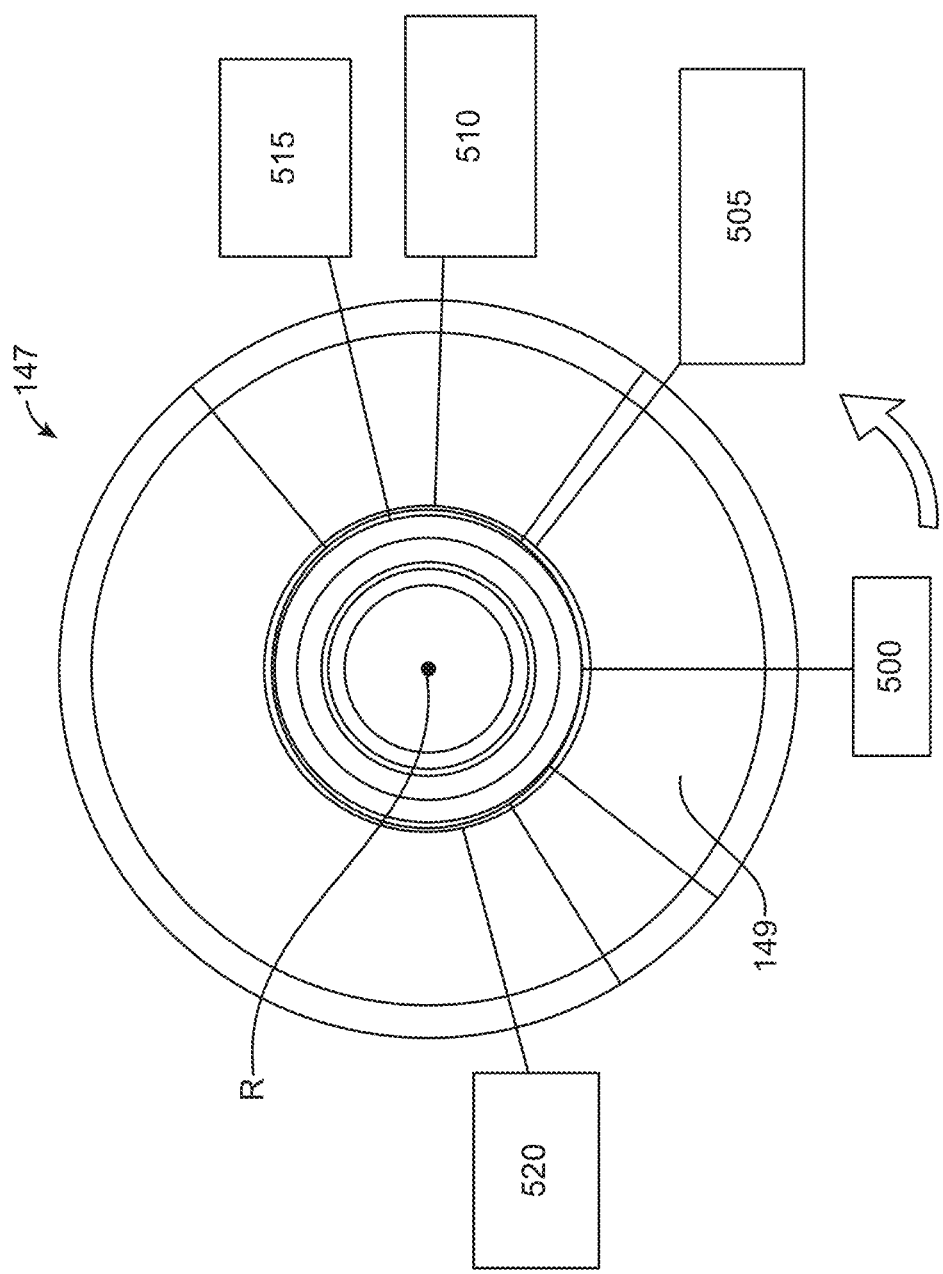
FIG. 9 illustrates timing of pump stroke with rotation of the rotary cam.
Figure 12:
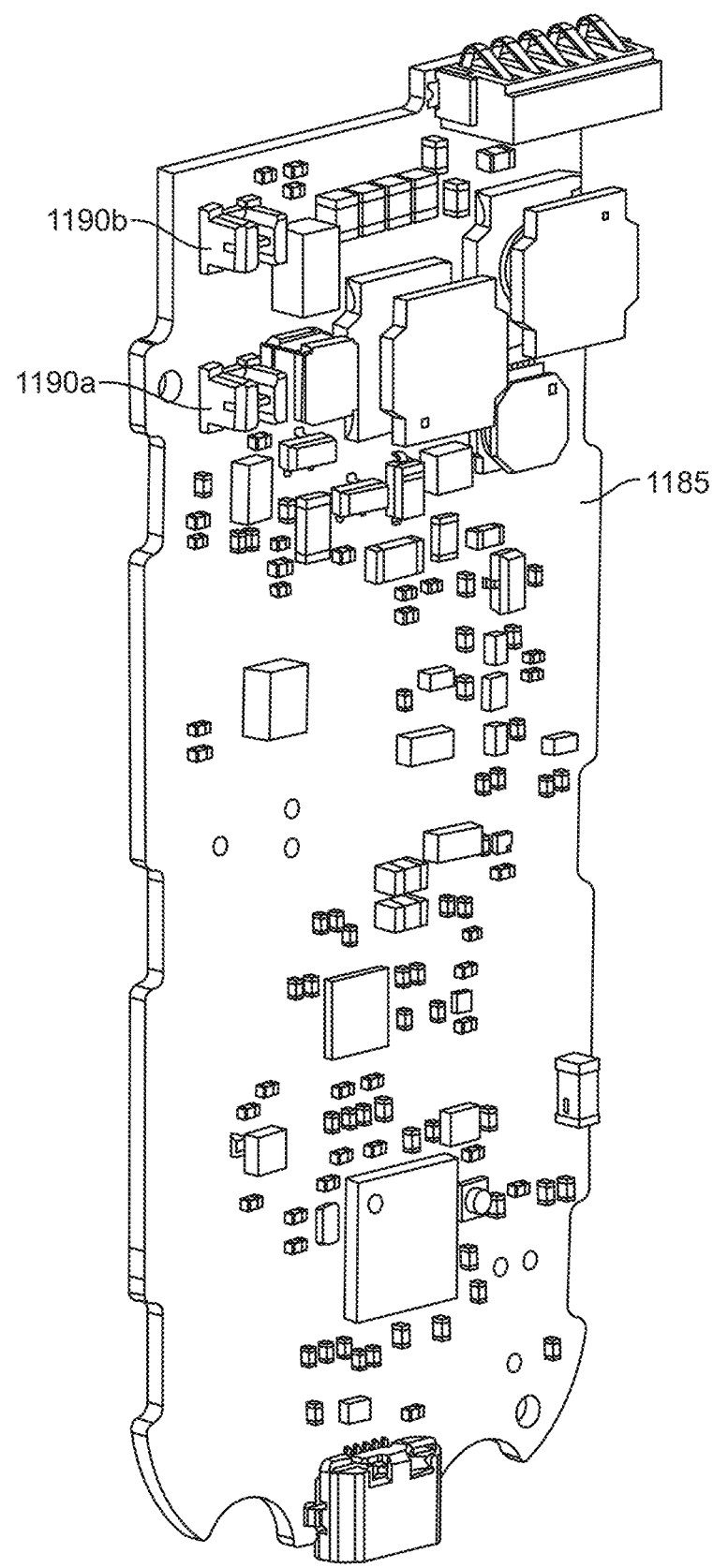
FIG. 12 illustrates a printed circuit board with cam position sensors.

FIG. 9 illustrates a pumping sequence of the drive spool 1620 as the rotary cam 147 rotates around a rotation axis R of the cam shaft 151. A first amount of rotation around the rotation axis R of the rotary cam 147 away from a HOME position (box 500) causes the projection 1645 on the floating spool 1625 to pierce the manifold film 1530 (see FIG. 6B). This is the start of a drawdown (box 505). Further rotation of the cam 147 causes an increase in the space between the drive spool 1620 and the floating spool 1625 to fill the space with fluid. After a second amount of rotation the drawdown ends (box 510) and the two spools 1620, 1625 with the space between them are pulled through the pumping chamber 1632 towards the channel 1607 leading to the ejector system 180. A third amount of rotation initiates the start of ejector system 180 filling (box 515) (FIG. 6A). The space containing the fluid between the upper and lower sliding seals 1630 of the drive spool 1620 is aligned with the channel 1607. The drive spool 1620 is urged upward while the floating spool 1625 remains in place ejecting the fluid from the space. A fourth amount of rotation terminates filling of the ejector system 180 (box 520) as the space is fully collapsed and the drive spool 1620 urges the floating spool 1625 towards the manifold film 1530 once again. Timing of ejection from the ejector system 180 can be programmed electronically to fire at a specified point in the pumping cycle. For example, the ejector system 180 can be programmed to fire after the ejector system 180 is completely filled with the dose. In some implementations, the ejector system 180 can be programmed to start firing while the drug is delivered to the ejector system 180. A first optic sensor 1190 (e.g., the LOW optic sensor 1190*a* shown in FIG. 12) can be triggered to initiate firing of the ejector system 180 upon being occluded with an optic flag 157 on the cam follower 153. In other implementations, the ejector system 180 can be programmed to start firing once the pumping action is completed when the space between the spools 1620, 1625 is collapsed and the microcup is at least partially filled. A second optic sensor 1190 (e.g., the HOME optic sensor 1190*b* shown in FIG. 12) can be triggered to initiate firing.

The pumping sequence is illustrated in more detail below and with respect to FIG. 10A-1 through FIG. 10E-2.

Figures 2, 10B:
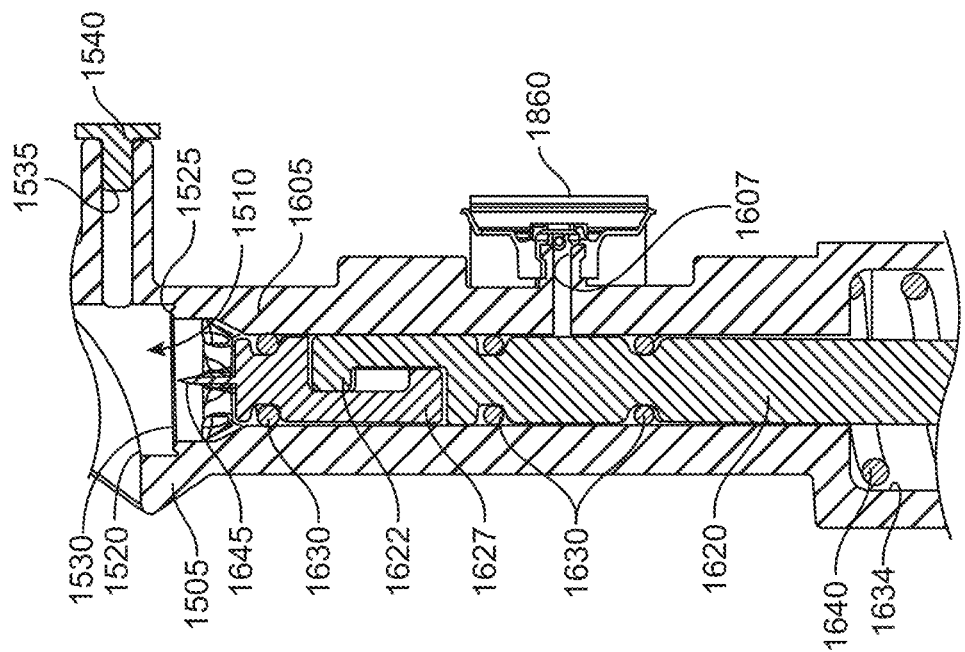
Figures 1, 10B:
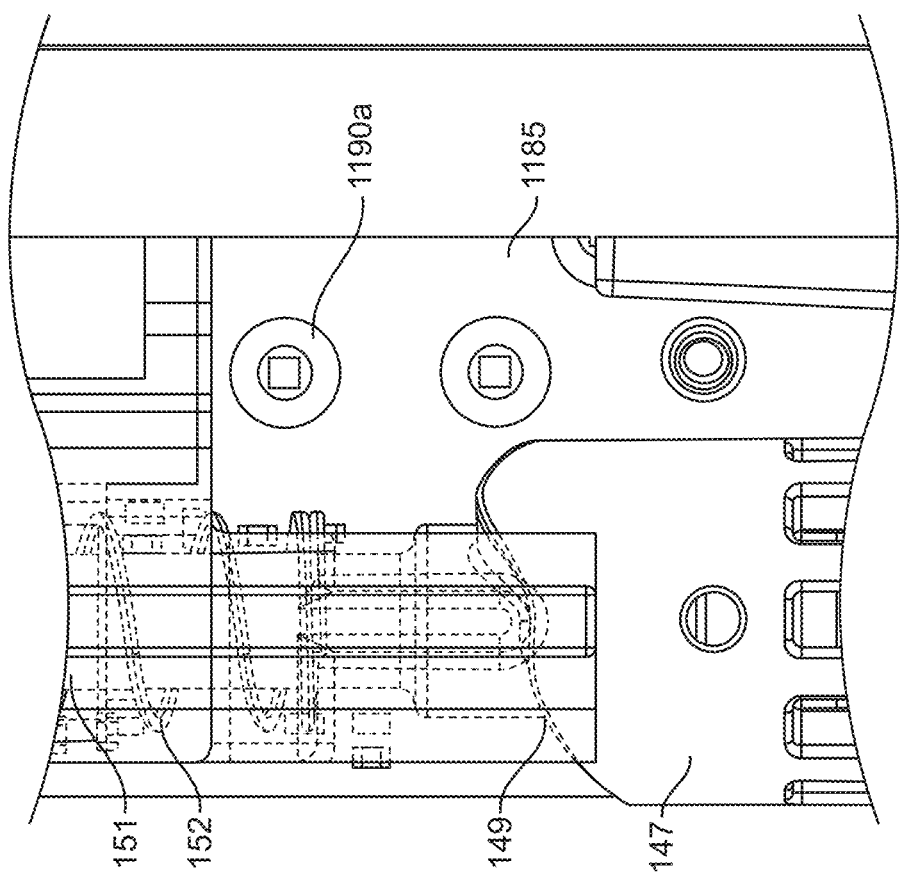

FIG. 10A-1 shows a cut-away view of the rotary cam 147 having its cam shaft 151 coupled to the cam follower 153. The PCB 1185 with a plurality of position sensors 1190*a*, 1190*b* is shown positioned behind the rotary cam 147 and cam follower 153. FIG. 10A-1 shows the base device 105 in a LOW position with the cam follower 153 occluding the low position sensor 1190*a*. FIG. 10A-2 shows the position of the spools 1620, 1625 within the pumping chamber 1632 of the pumping manifold 1605. The base device 105 can be stored with the rotary cam 147 in the LOW position during shipping or during exchange of cartridges 110. The low optic 1190*a* positioned on the PCB 1185 can be occluded by the cam follower 153 when the rotary cam 147 is in the LOW position.

When a user connects a cartridge 110 to the base device 105 and the shutter 170 on the base device 105 is lowered for the first time after cartridge 110 installation, the system 100 can "wake up." The rotary cam 147 can rotate around its rotation axis R into a HOME position. The rotary cam 147 is shown in FIG. 10B-1 having rotated from the LOW position of FIG. 10A-1 into the HOME position. The HOME position can be a location along the cam surface 149 that is higher than the LOW position, but not so high as to cause manifold film puncture. FIG. 10B-2 shows the position of the spools 1620, 1625 within the pumping chamber 1632 when the base device 105 is in the HOME position. The cam follower 153 can travel along the cam surface 149 and be lifted away from occluding the low optic 1190*a* into a position that occludes an upper home optic 1190*b*. on the PCB 1185. The drive spool 1620, which can be coupled to the cam follower 153, is driven through upward through the pumping chamber 1632 urging the floating spool 1625 towards the upper end of pumping chamber 1632.

Figures 2, 10C:
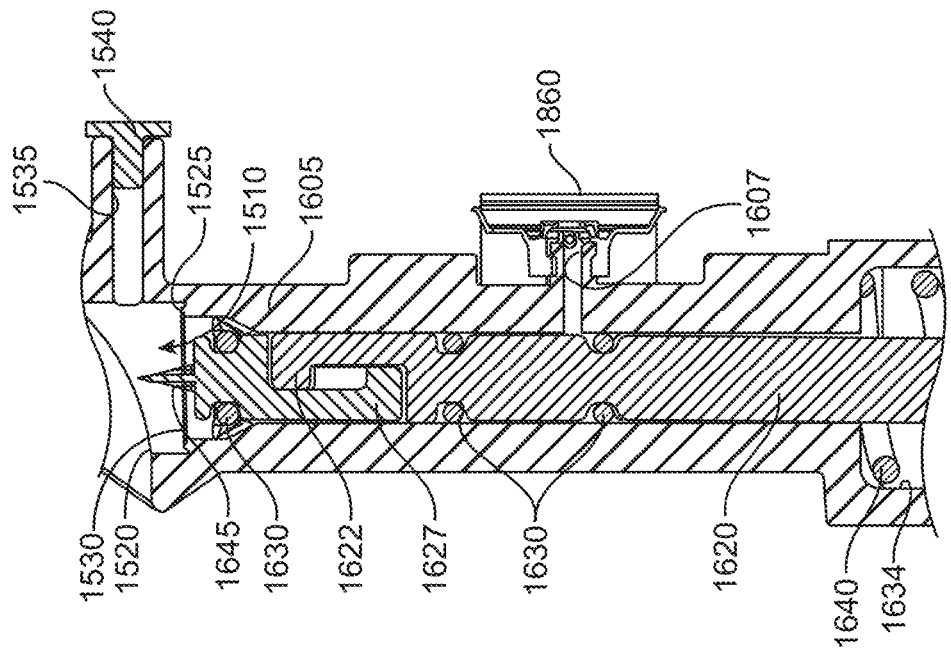
Figures 1, 10C:
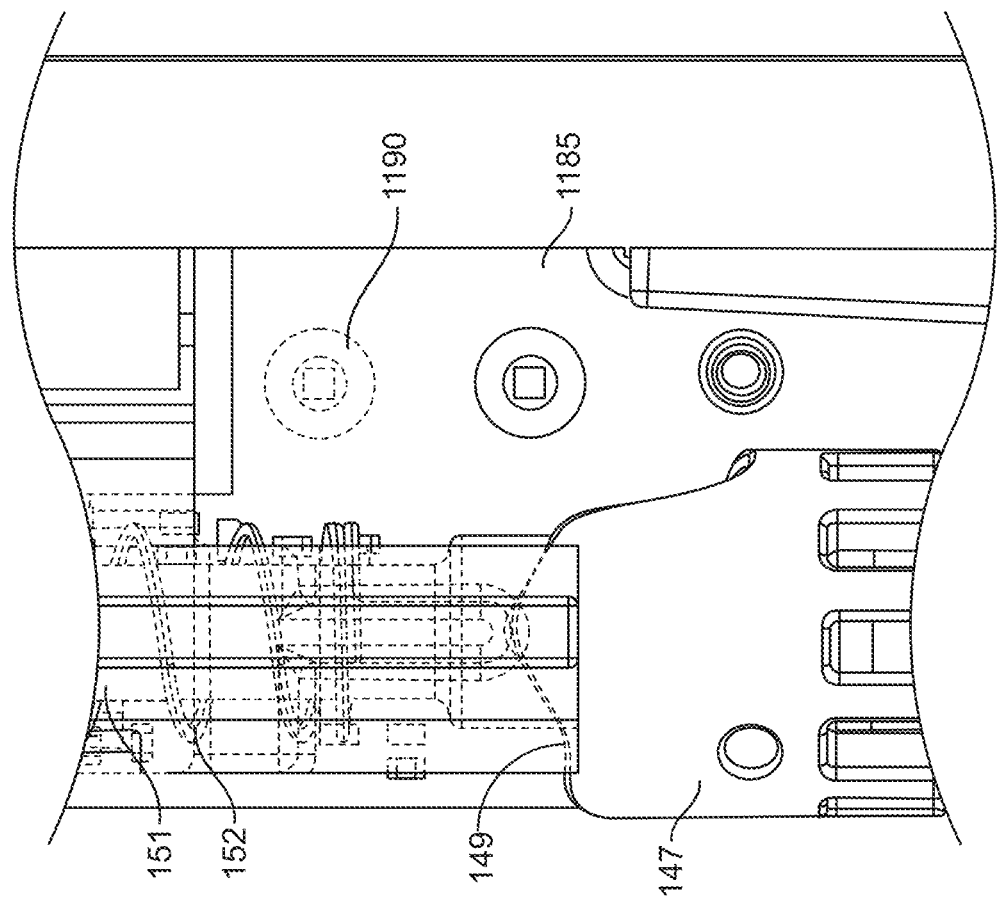

In addition to waking up the system, lowering of the shutter 170 reveals the dose button 172. When a user presses the dose button 172, the rotary cam 147 can rotate further around its rotation axis R. The cam follower 153 can travel further along the cam surface 149 and be lifted further upward (see FIG. 10C-1). The drive spool 1620 is driven further through the pumping chamber 1632 urging the projection 1645 on the floating spool 1625 to pierce the manifold film 1530 of the fluid container 155 (see FIG. 10C-2). Fluid from the reservoir 1510 of the fluid container 155 can enter the inlet of the pumping chamber 1632 and pass the top sliding seal 1630 of the floating spool 1625 as discussed above. This position is the start of fluid drawdown into the pumping manifold 1605. Penetration of the reservoir 1510 occurs only upon actuation of the shutter 170/dose button 172 and is directly linked to spool 1620, 1625 movement through the pumping chamber 1632.

Figures 2, 10D:
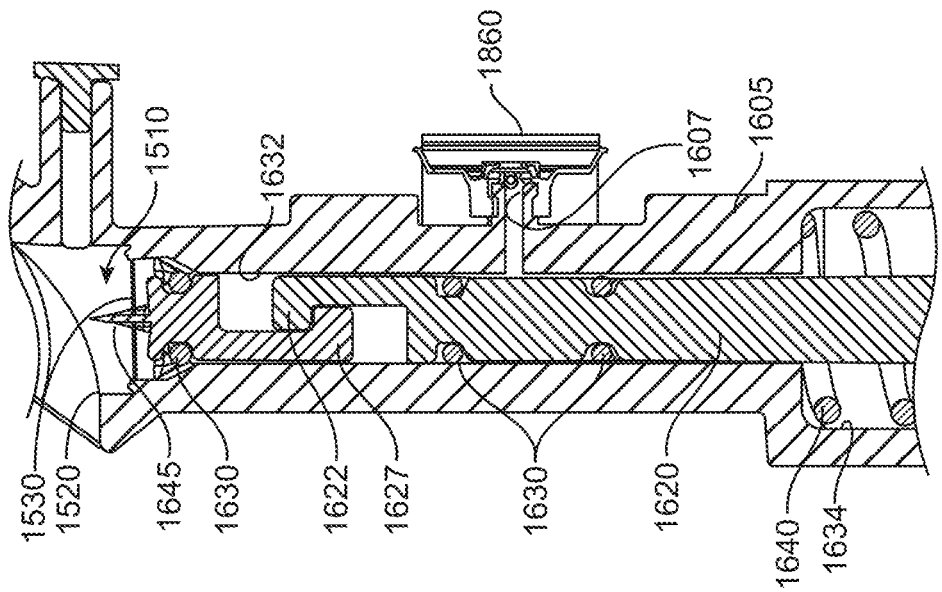
Figures 1, 10D:
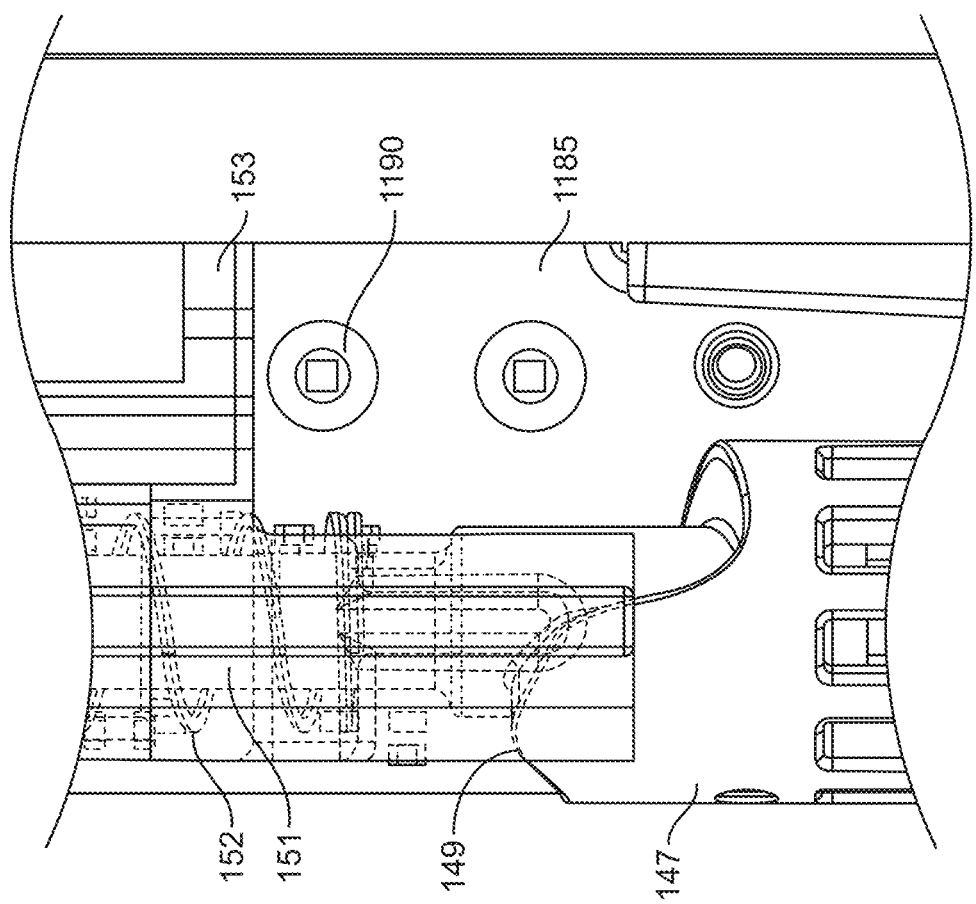

FIG. 10D-1 shows the rotary cam 147 rotating further and the cam follower 153 traveling down the cam path 149. The drive spool 1620 also moves downward. The floating spool 1625 can remain stationary within the pumping chamber 1632 due to friction between its sliding seal 1630 and the wall of the pumping chamber 1632. The space between the drive spool 1620 and floating spool 1625 increases as the spools spread further apart thereby creating a vacuum that draws fluid from the reservoir 1510 around the sliding seal 1630 of the floating spool 1625 and down into the pumping chamber 1632. The space between the drive spool 1620 and floating spool 1625 increases until the spool engagement ends 1622, 1627 engage with one another (see FIG. 10D-2).

FIG. 10E-1 shows the rotary cam 147 rotating further and the cam follower 153 traveling down the cam path 149 to the lowest point. The low optic 1190*a* is once again occluded. The drive spool 1620 has pulled the floating spool 1625 along with the fluid-filled space between the spools 1620, 1625 to travel down through the pumping chamber 1632. The sliding seal 1630 of the floating spool 1625 seals with the wall of the pumping chamber 1632 closing off the vacuum and fluid communication with the reservoir 1510. The fluid-filled space between the spools 1620, 1625 is exposed to the ejector system 180 via channel 1607 (see FIG. 10E-2). This is the start of the ejector system 180 filling. The ejector system 180 can be programmed to start firing at the start of filling.

FIG. 10E-1 shows the end of the ejector system 180 filling. The rotary cam 147 has rotated further around its axis R and the cam follower 153 traveled back up the cam path 149. This urges the drive spool 1620 to begin its upward motion stroke. Once again, the floating spool 1625 remains stationary due to friction between its sliding seal 1630 and the pumping chamber 1632 wall. The space between the drive spool 1620 and floating spool 1625 decreases as the drive spool 1620 is urged upward pushing the fluid from the space between the spools 1620, 1625 into the channel 1607 towards the ejector system 180. The full dose volume has been delivered to the ejector system 180 once the drive spool 1620 engages again with the floating spool 1625 as shown in FIG. 10E-2.

Further rotation of the rotary cam 147 can urge the cam follower to travel back to the HOME position as shown in FIG. 10B-1. The base device 105 can return to the HOME position automatically after a dose is delivered and can remain at rest until another delivery is desired. If the cam follower 153 ever gets knocked out of the HOME position and the cam 147 rotates back into the LOW position (or any other "non-home" position) while the base device 105 is at rest, the motor 145 can move it back into the HOME position in anticipation of a dose button 172 press the next time the shutter 170 is lowered. Lowering of the shutter 170 can automatically trigger the motor 145 to position the cam 147 and cam follower 153 into the HOME position.

When a cartridge 110 is disconnected from the base device 105, the rotary cam 147 can rotate from the HOME position to the LOW position in anticipation of a new cartridge 110 to be installed. The low optic 1190*a* can be occluded when in this LOW position. The cartridge 110 and the base device 105 can be connected or disconnected from one another regardless of filling of the fluid container 155. However, in order to remove a cartridge 110 from the base device 105, the pumping system 160 is preferably in the HOME position.

Ejector System

In addition to the fluid container 155 and the pumping system 160, the cartridge 110 can include an ejector system 180. The pumping system 160 is arranged to draw discrete volumes or doses of medicament from the reservoir 1510 of the fluid container 155 and deliver those discrete doses to the ejector system 180 through the channel 1607 extending through a wall in the pumping manifold 1605 at the location of the ejector system 180. The ejector system 180 can be a piezoelectric ejector system configured to deliver those discrete doses of medicament in the form of microdroplets.

Figure 11B:
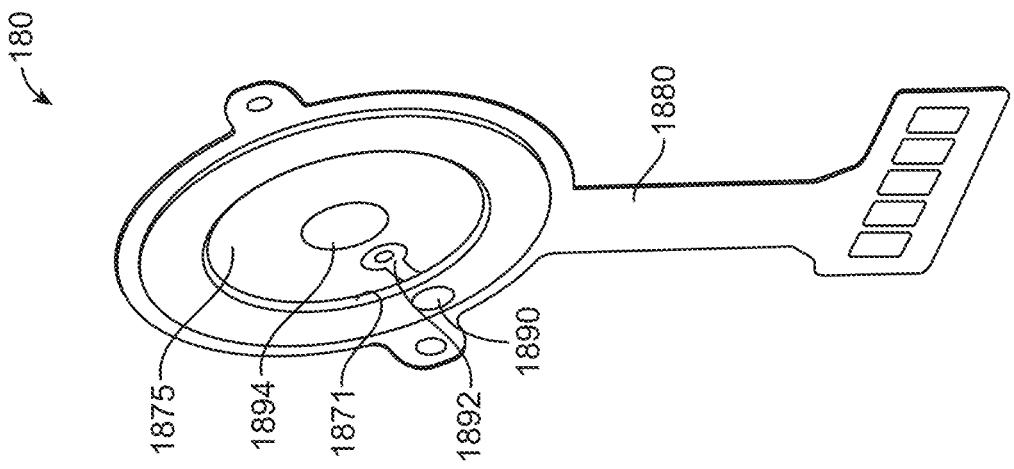
FIGS. 11A-11B are exploded and assembled perspective views, respectively of an ejector system.
Figure 11A:
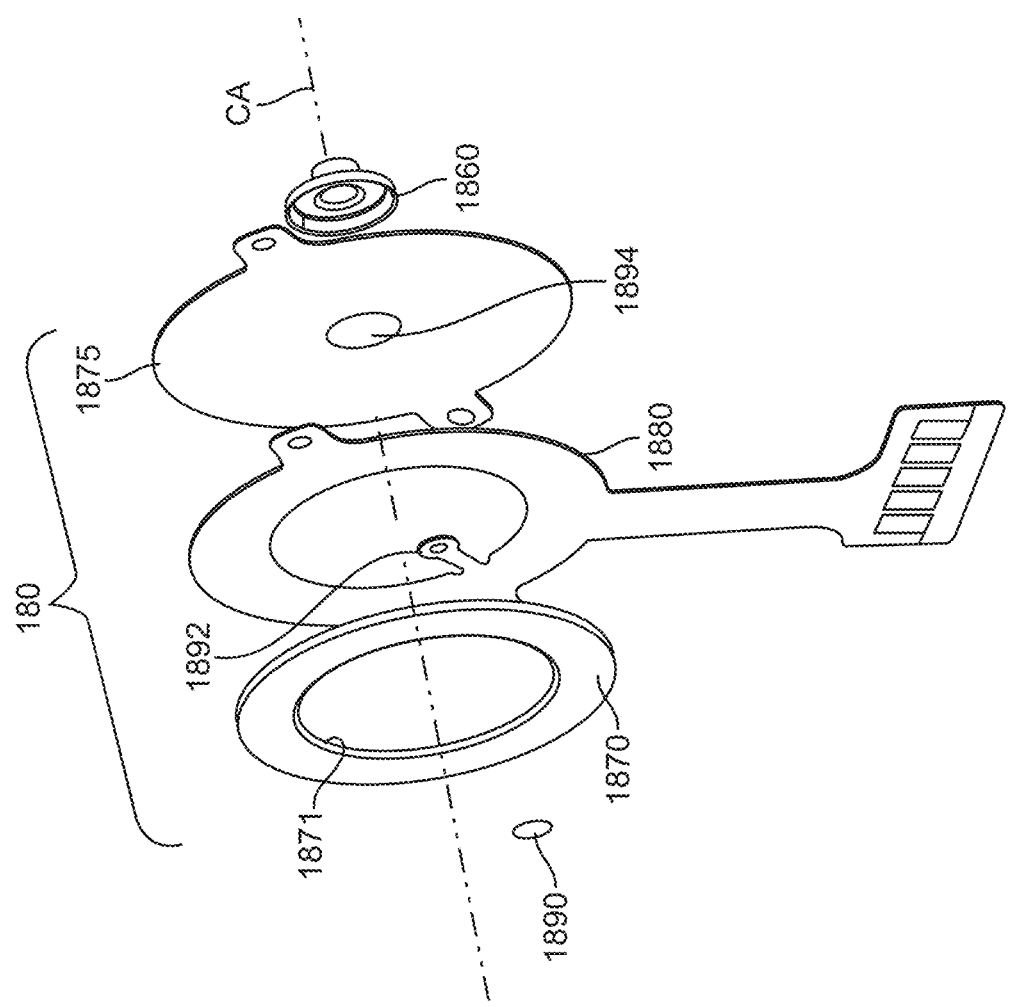

FIG. 4 is an exploded view of the cartridge 110 showing the ejector system 180. FIGS. 6A-6B are cross-sectional, partial side views and FIG. 7 is an exploded view of the cartridge 110 with the housing removed showing the relative arrangement of the fluid container 155, the pumping system 160, and the ejector system 180 of the cartridge 110. The ejector system 180 can include a microcup 1860 and a piezoelectric ejector 1865 (FIG. 4). The piezoelectric ejector 1865 can include a piezoelectric disc 1870, a pannulus 1875, a flex circuit 1880, and an ejector O-ring 1885. The piezoelectric disc 1870, pannulus 1875, flex circuit 1880, and ejector O-ring 1885 of the piezoelectric ejector 1865 can be sandwiched between a back plate 1887 and a front plate 1889 (FIGS. 6A-6B and FIG. 7). In an implementation, the ejector 1865 can include a combined flex circuit—pannulus, which can be referred to as a "fannulus", such that the pannulus is incorporated into the flex circuit as a laminated layer on the back side of the flex circuit. FIG. 11A is another exploded view of the ejector system 180 including the piezoelectric disc 1870, the flex circuit 1880, the pannulus 1875, and the microcup 1860. FIG. 11B shows the components of FIG. 11A assembled together with solder 1890 on a solder tab 1892 on the flexible circuit 1880. The solder tab 1892 can be folded over the inner diameter of the piezoelectric disc 1870 and soldered onto the surface of the piezoelectric disc 1870 during assembly. The pannulus 1875 can include a plurality of openings 1894 extending through it that are configured to generate droplets between 20 um and 100 um, or between 30 um and 90 um, or between 40 um and 90 um, or between 50 um and 70 um, or about 60 um. In some implementations, the droplet size is about 40 um. The plurality of openings 1894 can be approximately 40 um in diameter.

The pannulus 1875 is vibrated with the piezoelectric disc 1870 coupled to the pannulus 1875. The piezoelectric disc 1870 can be coupled to either a delivery side (front-facing) or a fluid side (rear-facing) of the pannulus 1875 with the openings 1894 positioned in an open central region 1871 of the piezoelectric disc 1870.

The term "fluid" as used herein refers to any flowable substance and does not refer only to the liquid state of a material.

The piezoelectric disc 1870 may be made of any suitable material (such as ceramic, Lead zirconate titanate (PZT) having the chemical formula $Pb[Zr_xTi_{1-x}]O_3$, or another intermetallic inorganic compound having piezoelectric effect when an electric field is applied. The pannulus 1875 can be formed of plastic such as PEEK, polyamide, or other materials. The pannulus 1875 can be designed to be completely planar, particular the nozzle area near the openings 1894.

The piezoelectric disc 1870 may be bonded, adhered, molded or otherwise coupled to the pannulus 1875 in any suitable manner as is known in the art. The flexible circuit 1880 can be in electrical communication with the piezoelectric disc 1870 to control the piezoelectric disc 1870. The flexible circuit 1880 can be coupled to the control processor 130 that controls the piezoelectric disc 1870 to induce vibrations in the piezoelectric disc 1870 to vibrate the pannulus 1875 and eject fluid from the openings 1894. The pannulus 1875 can be vibrated at a frequency of 100 to 160 khz, which may be a resonant frequency. The resonant frequency may be predetermined, measured, determined or tuned as is known in the art. The driving frequency of the piezoelectric disc 1870 is described further below.

The rear-facing, fluid side of the pannulus 1875 at the openings 1894 can be in contact with the fluid to be delivered and eject the fluid to the front-facing, delivery side. Fluid can be ejected through the openings 1894 toward the eye when the pannulus 1875 is vibrated. The openings 1894 can taper from the fluid side to the delivery side. For example, the openings 1894 at the fluid side may have a diameter of 160-240 microns (and may be 200 microns) while the diameter at the delivery side may be 20-60 microns (and may be 40 microns). A column of consistent diameter (20-60 microns) can extend to the delivery side and can have a length of 10-40 microns and can be about 25 microns in length. The openings 1894 can have a curved wall between the fluid and delivery sides with a radius of curvature of 100 microns. The openings 1894 at the fluid side and the delivery side can have a circular cross-sectional shape. As used herein, the cross-sectional area (or other dimension) may be defined by an effective diameter (or effective radius) for a circle having the same area.

The pannulus 1875 can have a thickness of 100 to 180 microns, or 120-160 microns, and can be about 140 microns. The pannulus 1875 can be made of any suitable material such as PEEK or Polyimide, with additional layers consisting of copper, polyimide, nickel, and/or gold. The pannulus 1875 can have a thickness of 125 microns and the coating/plating having a total thickness of about 15 microns so that the pannulus 1875 has thickness of about 140 microns. Other configurations of the pannulus 1875 and piezoelectric disc 1870 are considered herein including other dimensions of the openings.

Fluid can be ejected so that an average ejection velocity is 2.5 m/s to 15 m/s, as it leaves the opening at the delivery side and may be about 5-6 m/s. In some implementations, the velocity of droplets can be between 1 meter/second and 10 meters/second, or between about 4 meters/second and 5 meters/second. The pannulus 1875 can define a central axis CA, which is a central orientation of the plurality of openings 1894 defined by a geometric center of the ejection orientation of the plurality of openings. For a circular pattern of openings 1894 of even density distribution with a flat pannulus 1875 the central axis CA can extend perpendicular to plane of pannulus 1875 at the center of the circular pattern of openings 1894. Stated another way, the central axis CA can be perpendicular to a plane defined by the pannulus 1875 and can be aligned with the geometric center of the ejection direction that the openings 1894 are aligned or with a geometric center of a spray pattern created by the plurality of openings 1894. The central axis CA may be defined by an average or geometric center when, for example, the openings 1894 are clustered or an irregular or asymmetrical shape or varying density of openings 1894 (number of openings)/mm2 as used herein.

Individual doses of the fluid can be delivered by the pumping system 160 to the microcup 1860 and the pannulus 1875. The microcup 1860 can be substantially dry after delivery of the fluid and dry when stored which may provide advantages over "wet" systems which may suffer from undesirable contamination or evaporation. Implementations of the microcup 1860 of the ejector system 180 are described in more detail in PCT Publication No. WO2018/227190, which is incorporated herein by reference.

The volume of fluid delivered may fill the microcup 1860 only 75-90% full, which may provide room during delivery to encourage all of the fluid to gather in the microcup 1860 due to surface tension forces. Delivering the fluid at a velocity of at least 0.5 m/s (or at least 1.0 m/s) to the microcup 1860 may also encourage substantially all of the fluid ejected from the channel to collect in the microcup 1860 rather than being left behind as residual. Stated another way, the pump can deliver the fluid at a pressure of at least 200 psi (and may be about 300 psi) which may be sufficient to achieve the velocities desired for many fluids delivered to the eye. In this manner, the small fluid amount remains a single fluid "droplet" which is fired into the microcup 1860.

The fluid delivery completes a delivery of a single dose leaving the microcup 1860 substantially dry and free of residual fluid between activations. For example, the pannulus 1875 may deliver the fluid from the microcup 1860 so that no more than 5%, or no more than 2%, of a total volume of the microcup 1860 is occupied by residual fluid from a previous fluid delivery or less than about 1 microliter remains. Stated another way, the pannulus 1875 can be operated to dispense substantially the entire volume of fluid in communication with the openings 1894 so that no more than 5%, or no more than 2%, of the fluid volume (or less than 1 microliter) remains in the microcup 1860 after the fluid is ejected and a single actuation for fluid ejection. In this manner, the microcup 1860 is substantially empty after a single application of the fluid (a single firing actuation). The microcup 1860 can receive a single dose that is nearly completely delivered to leave the microcup 1860 substantially dry and free of residual fluid between activations. Contamination and degradation of the fluid may be reduced compared to "wet" systems that maintain the fluid in contact with the pannulus 1875 between uses or which have incomplete delivery.

The microcup 1860 can be sized so that the microcup 1860 is at least 70-95% full with the fluid volume as mentioned above, which may help the fluid to gather in the microcup 1860 as a single droplet. The microcup 1860 can define a relatively small volume such as less than 14 microliters or 10-14 microliters. The fluid volume may be 7-12 microliters or 10-12 microliters.

The ejector system 180 drives delivery of the drug through the spray aperture 118 in a microvolume dose (e.g. about 8 ul) with less than 100 milliseconds between the time the first droplet hits the corneal surface of the completion of the dose delivery. The entire event of pumping fluid from the fluid container 155 and delivering a full dose to the eye can occur in less than 200 milliseconds. The time is takes for a dose of fluid to be dispensed from the time the dose button is pressed until the last drop is delivered can be less than about 200 millisecond, less than about 150 milliseconds, or less than about 100 milliseconds. The pump sequence can begin upon dose button press. Within about 100 milliseconds after dose button press, the dosing begins, even if the pump sequence has not completed. If the ejector starts spraying before the full dose is delivered to the microcup 1860 from the pumping chamber 1632, the spray will last for no more than 100 milliseconds to ensure the full dose enters the eye quicker than a blink is possible. In some implementations, the pumping action can last a maximum of about 100 milliseconds and then the dosing can last a maximum of about 100 milliseconds. In another implementation, upon lowering the shutter 170, the dispenser can automatically pump drug to the microcup 1860 in anticipation of a dose button press. Then, once the dose button is pressed, the ejector sprays the full volume into the eye. In this implementation, the pump action (i.e. motion of the spools 1620, 1625) can be separated from the spray action (i.e. firing of the piezoelement). This separation of pump action from spray action aids in preventing missed doses due to flinching by the user upon hearing a noise during pumping. Pumping a dose prior to the dose button press can reduce potential flinch time even further. The microcup does not necessarily have to fill completely before ejecting the drug. In an implementation, the piezo can start firing before or during the act of drug being delivered to the microcup. The delivery can be so quick that a user observes it as a simultaneous pump/fire as one instantaneous ejection.

In use, fluid delivery to the eye may also be relatively rapid to reduce the likelihood of interference from a blink during delivery. The fluid delivery may take less than 200 ms and may even be less than 150 ms or even 100 ms. The pannulus 1875 can be operated with a pause between periods of vibration during a single actuation. For example, the pannulus 1875 can be driven by the piezoelectric disc 1870 for a first period of operation of about 26 ms with a pause of about 3.65 ms followed by a second period of operation of about 26 ms. The pannulus 1875 can be driven by the piezoelectric disc 1870 with two pauses with the piezoelectric disc 1870 being energized or activated for a first period of time, a second period of time and a third period of time with the first and second periods separated by the first pause and the second and third separated by a second pause in driving vibration of the pannulus 1875. The first and second pauses in driving vibration may be 0.5 ms to 4.0 ms. Each of the first, second and third time periods may be 20-40 ms and the overall time of delivery may be less than 150 and even less than 100 ms and may be about 85.3 ms. Each of the first, second and third periods of vibration may be further subdivided into periods of activation for about 816us and deactivated for about 586 us for the piezoelectric disc 1870. During the deactivated time, the pannulus 1875 may continue to vibrate and eject fluid although not being actively driven by the piezoelectric disc 1870. Similarly, during each pause in activation of the piezoelectric disc 1870 the pannulus 1875 may continue to eject the fluid. The "pause" may be defined as a continuous deactivation of at least 2% of the total time and the total pause time for a plurality of pauses being at least 6% and may be about 8.5% of the total delivery time. The deactivated times are defined distinct from the pause in that the pause is at least 2% of the time continuous while the deactivated time is shorter and may be defined as a continuous time of 0.5-1.0% of the total delivery time and a total of the deactivated times being at least 30% of the total delivery time. Stated another way, the deactivated time is a continuous time of 2.0 to 2.5% of the first period of time (and second and third as well) and a total deactivated time of at least 30% of the first period of time. The activation times and patterns may change depending on the surface tension of the ejected fluids.

An alternating current of electricity can be delivered to the piezoelectric disc 1870 via the flexible circuit 1880. The polarization of the piezo-electric disc 1870 can be fixed. In other words, there is a positive side and a negative side. When the alternating current is applied to both sides, electrical energy is transformed into physical energy in the form of a wave. This wave passes through the pannulus 1875 and imparts its physical energy to the fluid contained in the microcup 1860.

The trajectory of the fluid can be controlled by the geometry of the micronozzles or openings 1894 and moves in a straight path. The continual supply of fluid available can be propelled in multiple waves.

As mentioned above, the frequency of the alternating signal used to activate the piezoelectric disc 1870 and subsequently activate and vibrate the pannulus 1875 can be induced at a drive frequency between 100 kHz to 160 kHz. Furthermore, the frequency can be selected by the control processor 130 as a randomized frequency centered about the drive frequency (ranging from 100 kHz to 160 kHz, or between 110 kHz and 145 kHz, or a center frequency target of about 132 kHz with dithering) for each of the plurality of activations during a single delivery and may be randomized at least 20 and may be at least 40 times. Stated another way, the vibration frequency can be changed (randomly in a manner centered on the drive frequency) on average at least 33 times for a single firing actuation so that the piezoelectric disc 1870 is driven at a frequency for no more than 3% of the delivery time (average) before being changed. It is believed that the chaotic nature of the randomization of the drive signal may aid in ejecting fluid. The randomized nature may be provided by a predetermined randomized set of values that are applied to the centered operating frequency or the randomized values uniquely generated by the control processor 130.

The frequency of operation may be at a frequency other than a resonant frequency of the piezoelectric disc 1870. Tuning the frequency to be slightly off the resonant frequency can allow control of the ejection velocity and plume shape for a given applied voltage. Thus, the piezoelectric disc 1870 can be driven so it is near, but off its resonant frequency. The drive frequency can vary +/−2 k Hz around the center drive frequency. Dithering can improve droplet formation and mitigate issues with back-splatter on the ejector face when drops fail to break off cleanly. In some implementations, a relatively random dither frequency generator is used that is at least about 50%, 55%, 60%, 65%, 70%, or 75% below the nominal drive frequency (e.g., 123 kHz) with the balance above such that all frequencies chosen are within the +/−2 kHz window, but very little at the window edges.

The pannulus 1875 can also be designed to vibrate with a relatively low maximum amplitude. For example, the pannulus 1875 can vibrate with a maximum amplitude of less than 2 microns, less than 1.5 microns or within a range of 0.5-1.5 microns, 0.8-1.2 microns or may be about 0.8 microns. The maximum amplitude of the pannulus 1875 can also be relatively small compared to the size of the openings in the pannulus 1875. For example, the maximum amplitude may be no more than 5%, or no more than 3%, of an effective diameter of the cross-sectional shape of the openings at the delivery side. For example, when the maximum amplitude is 1.0 microns and the average diameter of the openings at the delivery side is 40 microns the maximum amplitude is only 2.5% of the average diameter or about 2.5% of the average diameter of the fluid droplets ejected. The maximum amplitude also represents a relatively small amount compared to the thickness such as no more than 5.0% or even no more than 3.0% of the thickness of the pannulus 1875 (measured from the fluid side to the delivery side). As used herein, the thickness may be an average thickness for the area bounded by the openings. Operation at low amplitude may also contribute to venting through the openings in that air may be admitted through some of the openings having even low displacements. Operation at low amplitude may also help maintain fluid containment between the microcup 1860 and the pannulus 1875. When the edge of the microcup 1860 is spaced apart from the pannulus 1875, the edge may be spaced apart an average distance greater than the maximum amplitude of the pannulus 1875 during vibration. Stated another way, the maximum amplitude is less than an average separation distance between the surface of the edge of the microcup 1860 and the pannulus 1875.

Therapeutic Agents

The systems described herein can be used to delivery any of a variety of therapeutic agents or combinations of therapeutic agents to a patient to treat a condition. Examples of conditions include: myopia, presbyopia, dry eye, glaucoma, allergies, infections, bacterial infections, viral infections, and other infections, rosacea keratitis, chronic inflammatory conditions such as thyroiditis and blepharitis, selected retinal conditions such as diabetic retinopathy, age-related macular degeneration, and other retinal conditions, postoperative, amblyopia, etc.

The drug families used for the treatment of the aforementioned conditions include: steroids, anti-inflammatory agents, antibiotics, compounds for the treatment of glaucoma, antihistamines, dry eye treatments, neuroprotective agents, retinoids, anti-neoplastics Vascular agents, antioxidants, and biologics.

Any medicament showing a desired ophthalmic activity may be administered. In an aspect, the medicament is available by prescription. In another aspect, the medicament is available over-the-counter. In an aspect, the medicament is or comprises a biologic agent. In an aspect, the biologic agent is selected from the group consisting of a full-length antibody, an active fragment of a full-length antibody, a peptide, a pegylated peptide, and an enzymatic ingredient. In another aspect, the biologic ingredient is selected from the group consisting of bevacizumab, ranibizumab, FV fragments, bi-specific antibodies, fusion molecules, pegaptanib, plasmin and microplasmin. In a further aspect, the biologic agent is selected from the group consisting of ranibizumab antibody FAB (including Lucentis™), VEGF Trap fusion molecule (including VEGF Trap-Eye™), microplasmin enzyme (including Ocriplasmin™), macugen pegylated polypeptide (including Pegaptanib™), and bevacizumab (including Avastin™)

In an aspect, the medicament to be delivered comprises a medicament selected from the group consisting of atropine, pirenzepine, 7-methylxanthine, pilocarpine, diclofenac, carbachol, brimonidine, NSAID, phenylephrine, nepafenac, pheniramine, napthazoline, carboxymethylcellulose sodium, tetrahydrozoline HCl, pheniramine maleate, ketotifen fumarate, oxymetazoline HCl, naphazoline HCl, pheniramine maleate, moxifloxacin hydrochloride, bromfenac, proparacaine hydrochloride, difluprednate, gatifloxacin, travoprost, bepotastine besilate, gatifloxacin, loteprednol etabonate, timolol ophthalmic, olopatadine hydrochloride, phenylephrine hydrochloride, levofloxacin, ketorolac tromethamine, letanoprost, bimatoprost and BAK free latanoprost. In another aspect, the medicament is selected from the group consisting of Refresh Tears™, Visine Advanced Relief™, Naphcon A™, Sensitive Eyes™, Renu™, Opti-Free™ rewetting drops, Visine A.C.™, Hypo Tears™ Alaway™, Visine Visine™ original, Rohto Cool™, Soothe XP™, Zaditor™, Bausch & Lomb Advanced Eye Relief Redness™, Visine A™, Opcon-A™, Walgreens artificial tears, Visine™ dry eye relief, Advanced Eye Relief Dry Eye™, Opti-free Replenish™, Clear Eyes™ redness relief, Vigamox™, Bromday™, Durezol™, Zymaxid™, Travatan Z™, Tropicamide™, Bepreve™, Zymar™, Lotemax™, Istalol™, Pataday™, AK-Dilate™, Toradol™, Xalatan™, and Lumigan™.

In another aspect, the medicament to be delivered comprises a medicament selected from the group consisting of fluorosilicone acrylate, sodium carboxymethylcellulose, hydroxypropyl methylcellulose, tetrahydrozoline HCl, carboxymethylcellulose sodium, propylene glycol, hypromellose, zinc sulfate, dorzolamide HCl timolol maleate, azithromycin, brimonidine tartrate, nepafenac, brinzolamide, besifloxacin, dorzolamide HCl, prenisone acetate, loteprednol etabonate, tobramycin/dexamethasone, and cyclosporine. In a further aspect, the medicament is selected from the group consisting of Tears Naturale II™, Optimum NWN™, Thera Tears™, Systane Ultra™, GenTeal™, Systane Lubricant Eye Drops™, Blink™ tears, Visine Max Redness Relief™, Refresh Optive™, Muro128™, Systane Balance™, Rohto Hydra™, Rohto Ice™, Walgreens sterile artificial tears, Rohto Arctic™, Clear Eyes™ natural tears lubricant, Similasan™ pink eye relief, Similasan™ allergy eye relief, Cosopt™, AzaSite™ Alphagan P™ Nevanac™, Azopt™, Besivance™ Trusopt™ Alrex™, Alrex™, and Restasis™.

In an aspect, an ophthalmic medicament to be delivered is used to treat glaucoma. In an aspect, a glaucoma medicament is selected from the group consisting of travoprost, timolol ophthalmic, latanoprost, bimatoprost, dorzolamide HCl timolol maleate, brimonidine tartrate, brinzolamide, dorzolamide HCl, and BAK free latanoprost. In a further aspect, a medicament is selected from the group consisting of travoprost, timolol ophthalmic, latanoprost, bimatoprost, and BAK free latanoprost. In another aspect, a medicament is selected from the group consisting of dorzolamide HCl timolol maleate, brimonidine tartrate, brinzolamide, and dorzolamide HCl. In an aspect, a glaucoma medicament is selected from the group consisting of Travatan™, Istalol™, Xalatan™, Lumigan™, Cosopt™, Alphagan P™, Azopt™, and Trusopt™. In another aspect, a medicament is selected from the group consisting of Travatan™, Istolol™, Xalatan™ and Lumigan™. In a further aspect, a medicament is selected from the group consisting of Cosopt™, Alphagan P™, Azopt™, and Dorzolamide HCL™.

In an aspect, the concentration of an active ingredient in a medicament is measured as a percentage of the active ingredient in solution. In an aspect, the concentration of active ingredient ranges from about 0.0001% to about 5%. In another aspect, the concentration of active ingredient in a medicament ranges from about 0.0005% to about 1%. In other aspects, the concentration of active ingredient ranges from about 0.0005% to about 0.0001%, from about 0.0001% to about 0.001%, or from about 0.0005% to about 0.001%. In other aspects, the concentration of active ingredient ranges from about 0.005% to about 0.001% or from about 0.001% to about 0.01%. In another aspect, the concentration of active ingredient ranges from about 0.001% to about 0.5%. In various other aspects, the concentration of active ingredient is selected from the group consisting of about 0.0001%, about 0.0005%, about 0.001%, about 0.0025%, about 0.005%, about 0.01%, about 0.025%, about 0.05%, about 0.1%, about 0.2%, about 0.3%, about 0.4%, about 0.5%, about 0.75%, about 1%, about 1.5%, about 2%, about 2.5%, about 3%, about 4%, and about 5% measured as a percentage of the solution. However, given the lower dosing amounts afforded by the methods of the present disclosure, higher concentrations may be used depending on the intended use. For examples, about 10%, about 20%, about 25%, of the active ingredient in the medicament, measured as a percentage of the solution, may be utilized.

In an aspect, the medicament comprises a medicament selected from the group consisting of between about 0.02% and about 0.03% carboxymethylcellulose sodium, between about 0.4% and about 0.6% carboxymethylcellulose sodium, between about 0.04% and about 0.06% tetrahydrozoline HCl, between about 0.04% and about 0.06% tetrahydrozolinc HCl, between about 0.24% and about 0.36% pheniramine maleate, between about 0.02% and about 0.03% ketotifen fumarate, between about 0.028% and about 0.042% ketotifen fumarate, between about 0.02% and about 0.03% oxymetazoline HCl, between about 0.0096% and about 0.0144% naphazoline HCl, between about 0.024% and about 0.036% naphazoline HCl, between about 0.24% and 0.36% pheniramine maleate, between about 0.4% and about 0.6% moxifloxacin hydrochloride, between about 0.072% and about 0.108% bromfenac, between about 0.4% and about 0.6% proparacaine hydrochloride, between about 0.04% and about 0.06% difluprednate, between about 0.4% and about 0.6% gatifloxacin, between about 0.0032% and about 0.0048% travoprost, between about 1.2% and about 1.8% bepotastine besilate, between about 0.24% and about 0.36% gatifloxacin, between about 0.4% and about 0.6% loteprednol etabonate, between about 0.4% and about 0.6% timolol ophthalmic, between about 0.16% and about 0.24% olopatadine hydrochloride, between about 2% and about 3% phenylephrine hydrochloride, between about 0.4% and about 0.6% levofloxacin, between about 0.32% and about 0.48% ketorolac tromethamine, between about 0.004% and about 0.006% letanoprost, and between about 0.024% and about 0.036% bimatoprost.

In an aspect, the medicament comprises a medicament selected from the group consisting of 0.025% carboxymethylcellulose sodium, 0.5% carboxymethylcellulose sodium, 0.05% tetrahydrozoline HCl, 0.5%, tetrahydrozoline HCl, 0.3% pheniramine maleate, 0.025% ketotifen fumarate, 0.035% ketotifen fumarate, 0.025% oxymetazoline HCl, 0.012% naphazoline HCl, 0.03% naphazoline HCl, 0.3% pheniramine maleate, 0.5% moxifloxacin hydrochloride, 0.09% bromfenac, 0.5% proparacaine hydrochloride, 0.05% difluprednate, 0.5% gatifloxacin, 0.004% travoprost, 1.5% bepotastine besilate, 0.3% gatifloxacin, 0.5% loteprednol etabonate, 0.5% timolol ophthalmic, 0.2% olopatadine hydrochloride, 2.5% phenylephrine hydrochloride, 0.5% levofloxacin, 0.4% ketorolac tromethamine, 0.005% letanoprost, and 0.03% bimatoprost.

In another aspect, the medicament to be delivered comprises a medicament selected from the group consisting of between about 0.02% and about 0.3% sodium carboxymethylcellulose, between about 0.04% and about 0.06% tetrahydrozoline HCl, between about 0.4% and about 0.6% carboxymethylcellulose sodium, between about 0.48% and about 0.72% propylene glycol, between about 0.24% and about 0.36% hypromellose, between about 0.2% and about 0.3% zinc sulfate, between about 0.8% and about 1.2% azithromycin, between about 0.08% and about 0.12% brimonidine tartrate, between about 0.08% and about 0.12% nepafenac, between about 0.8% and about 1.2% brinzolamide, between about 0.48% and about 0.72% besifloxacin, between about 1.6% and about 2.4% dorzolamide HCl, between about 0.8% and about 1.2% prenisone acetate, between about 0.16% and about 0.24% loteprednol etabonate, between about 0.32% and about 0.48% tobramycin/dexamethasone, and between about 0.04% and about 0.06% cyclosporine.

In another aspect, the medicament to be delivered comprises a medicament selected from the group consisting of 0.025% sodium carboxymethylcellulose, 0.05% tetrahydrozoline HCl, 0.5% carboxymethylcellulose sodium, 0.6% propylene glycol, 0.3% hypromellose, 0.25% zinc sulfate, 1% azithromycin, 0.1% brimonidine tartrate, 0.1% nepafenac, 1% brinzolamide, 0.6% besifloxacin, 2% dorzolamide HCl, 1% prenisone acetate, 0.2% loteprednol etabonate, 0.4% tobramycin/dexamethasone, and 0.05% cyclosporine.

The terms "microdroplet" or "pharmaceutical microdroplet" are used interchangeably and refer to a droplet of the medicament in the form of an aqueous solution that is ejected through the openings 1894 toward the eye when the pannulus 1875 is vibrated. In embodiments, the microdroplet is a piezo-enabled aqueous solution capable of causing fluid movement. In embodiments, the microdroplet has a diameter from about 20 microns to about 60 microns. In embodiments, the microdroplet has a diameter from about 30 microns to about 50 microns. In embodiments, the microdroplet has a diameter from about 35 microns to about 45 microns. In embodiments, the microdroplet has a diameter of about 40 microns. In embodiments, any of the medicaments described herein is in the form of a microdroplet. In embodiments, any of the medicaments described herein is in the form of a plurality of microdroplets.

In embodiments, the medicament is a microdroplet or an aqueous pharmaceutical composition comprising phenylephrine and tropicamide. In embodiments, the microdroplet or aqueous pharmaceutical composition comprises from about 1.0 wt % to about 4.0 wt % phenylephrine and about 0.1 wt % to about 2.0 wt % tropicamide. In embodiments, the microdroplet or aqueous pharmaceutical composition comprises from about 2.0 wt % to about 3.0 wt % phenylephrine and about 0.5 wt % to about 1.5 wt % tropicamide. In embodiments, the microdroplet or aqueous pharmaceutical composition comprises about 2.5 wt % phenylephrine and about 1.0 wt % tropicamide. In embodiments, the microdroplet or aqueous pharmaceutical composition further comprises benzalkonium chloride. In embodiments, the microdroplet or aqueous pharmaceutical composition further comprises from about 0.001 wt % to about 0.1 wt % benzalkonium chloride. In embodiments, the microdroplet or aqueous pharmaceutical composition further comprises from about 0.005 wt % to about 0.06 wt % benzalkonium chloride. In embodiments, the microdroplet or aqueous pharmaceutical composition further comprises about 0.01 wt % benzalkonium chloride. In embodiments, the microdroplet or aqueous pharmaceutical composition further comprises sodium chloride. In embodiments, the microdroplet or aqueous pharmaceutical composition comprises about 2.5 wt % phenylephrine, about 1.0 wt % tropicamide, about 0.01 wt % benzalkonium chloride, and sodium chloride. In embodiments, the microdroplet or aqueous pharmaceutical composition further comprises an acid (e.g., HCl) or a base (e.g., NaOH) to adjust the pH of the solution from about 7 to about 7.3 In embodiments, the microdroplet or aqueous pharmaceutical composition is a solution. In embodiments, the medicament is a microdroplet. In embodiments, the medicament is an aqueous pharmaceutical composition having a volume from about 1 ml to about 10 ml. In embodiments, the aqueous pharmaceutical composition has a volume from about 2 ml to about 5 ml. In embodiments, the aqueous pharmaceutical composition has a volume from about 2.5 ml to about 3 ml. In embodiments, the microdroplet or aqueous pharmaceutical composition is a piezo-enabled formulation capable of causing fluid movement. Throughout, the term "wt %" refers to weight/volume percentage concentration.

In embodiments, the medicament is a microdroplet or an aqueous pharmaceutical composition comprising atropine. In embodiments, the microdroplet or aqueous pharmaceutical composition comprises from about 0.01 wt % to about 1 wt % atropine. In embodiments, the microdroplet or aqueous pharmaceutical composition comprises from about 0.01 wt % to about 1 wt % atropine, sodium phosphate, benzalkonium chloride, and sodium chloride. In embodiments, the microdroplet or aqueous pharmaceutical composition comprises from about 0.05 wt % to about 0.2 wt % atropine, about 0.10 wt % to about 0.15 wt % sodium phosphate, about 0.009 wt % to about 0.016 wt % benzalkonium chloride, and about 0.8 wt % to about 1.0 wt % sodium chloride. In embodiments, the microdroplet or aqueous pharmaceutical composition comprises about 0.1 wt % atropine, about 0.136 wt % sodium phosphate, about 0.011 wt % benzalkonium chloride, and about 0.9 wt % sodium chloride. In embodiments, the microdroplet or aqueous pharmaceutical solution comprises about 0.1 wt % atropine, about 0.136 wt % sodium phosphate, about 0.011 wt % benzalkonium chloride, and about 0.9 wt % sodium chloride. In embodiments, the microdroplet or aqueous pharmaceutical composition further comprises an acid (e.g., HCl) or a base (e.g., NaOH) to adjust the pH of the solution from about 7 to about 7.3. In embodiments, the microdroplet or aqueous pharmaceutical composition is a solution. In embodiments, the medicament is a microdroplet. In embodiments, the medicament is a plurality of microdroplets. In embodiments, the medicament is an aqueous pharmaceutical composition having a volume from about 1 ml to about 10 ml. In embodiments, the aqueous pharmaceutical composition has a volume from about 2 ml to about 5 ml. In embodiments, the aqueous pharmaceutical composition has a volume from about 2.5 ml to about 3 ml. In embodiments, the microdroplet or aqueous pharmaceutical composition is a piezo-enabled formulation capable of causing fluid movement.

In embodiments, the microdroplet or aqueous pharmaceutical composition comprises from about 0.005 wt % to about 0.006 wt % atropine, about 0.10 wt % to about 0.15 wt % sodium phosphate, about 0.009 wt % to about 0.016 wt % benzalkonium chloride, and about 0.8 wt % to about 1.0 wt % sodium chloride. In embodiments, the microdroplet or aqueous pharmaceutical composition comprises about 0.01 wt % atropine, about 0.136 wt % sodium phosphate, about 0.011 wt % benzalkonium chloride, and about 0.9 wt % sodium chloride. In embodiments, the microdroplet or aqueous pharmaceutical composition is a solution. In embodiments, the microdroplet or aqueous pharmaceutical solution comprises about 0.01 wt % atropine, about 0.136 wt % sodium phosphate, about 0.011 wt % benzalkonium chloride, and about 0.9 wt % sodium chloride. In embodiments, the microdroplet or aqueous pharmaceutical composition further comprises an acid (e.g., HCl) or a base (e.g., NaOH) to adjust the pH of the solution from about 7 to about 7.3. In embodiments, the microdroplet or aqueous pharmaceutical composition is a solution. In embodiments, the medicament is a microdroplet. In embodiments, the medicament is a plurality of microdroplets. In embodiments, the medicament is an aqueous pharmaceutical composition having a volume from about 1 ml to about 10 ml. In embodiments, the aqueous pharmaceutical composition has a volume from about 2 ml to about 5 ml. In embodiments, the aqueous pharmaceutical composition has a volume from about 2.5 ml to about 3 ml. In embodiments, the microdroplet or aqueous pharmaceutical composition is a piezo-enabled formulation capable of causing fluid movement.

In embodiments, the medicament is a microdroplet or an aqueous pharmaceutical composition comprising latanoprost. In embodiments, the aqueous pharmaceutical compositions comprise latanoprost, sodium phosphate, benzalkonium chloride, sodium chloride, and a polypropylene glycol/polyethylene glycol copolymer. In embodiments, the aqueous pharmaceutical compositions comprises from about 0.005 wt % to about 0.01 wt % latanoprost, about 0.10 wt % to about 0.15 wt % sodium phosphate, about 0.01 wt % to about 0.03 wt % benzalkonium chloride, about 0.8 wt % to about 1.0 wt % sodium chloride, and about 0.1 wt % to about 0.3 wt % of a polypropylene glycol/polyethylene glycol copolymer. In embodiments, the aqueous pharmaceutical compositions comprises from about 0.0075 wt % latanoprost, about 0.136 wt % sodium phosphate, about 0.02 wt % benzalkonium chloride, about 0.9 wt % sodium chloride, and about 0.2 wt % of a polypropylene glycol/polyethylene glycol copolymer. In embodiments, the sodium phosphate comprises monobasic sodium phosphate, dibasic sodium phosphate, or a mixture thereof. In embodiments, the sodium phosphate comprises monobasic sodium phosphate. In embodiments, the sodium phosphate comprises dibasic sodium phosphate. In embodiments, the sodium phosphate comprises monobasic sodium phosphate and dibasic sodium phosphate. In embodiments, the polypropylene glycol/polyethylene glycol copolymer is a triblock copolymer having a central hydrophobic block of polypropylene glycol flanked by two hydrophilic blocks of polyethylene glycol. In embodiments, the approximate lengths of the two polyethylene glycol blocks is about 90 to about 110 repeat units, while the approximate length of the propylene glycol block is about 50 to about 60 repeat units. In embodiments, the approximate lengths of the two polyethylene glycol blocks is about 101 repeat units, while the approximate length of the propylene glycol block is about 56 repeat units. In embodiments, the polypropylene glycol/polyethylene glycol copolymer is poloxamer 407. In embodiments, the microdroplet or aqueous pharmaceutical composition further comprises an acid (e.g., HCl) or a base (e.g., NaOH) to adjust the pH of the solution from about 7 to about 7.3. In embodiments, the microdroplet or aqueous pharmaceutical composition is a solution. In embodiments, the medicament is a microdroplet. In embodiments, the medicament is a plurality of microdroplets. In embodiments, the medicament is an aqueous pharmaceutical composition having a volume from about 1 ml to about 10 ml. In embodiments, the aqueous pharmaceutical composition has a volume from about 2 ml to about 5 ml. In embodiments, the aqueous pharmaceutical composition has a volume from about 2.5 ml to about 3 ml. In embodiments, the microdroplet or aqueous pharmaceutical composition is a piezo-enabled formulation capable of causing fluid movement.

In embodiments, the medicament is a microdroplet or an aqueous pharmaceutical composition comprising pilocarpine. In embodiments, the microdroplet or aqueous pharmaceutical composition comprises pilocarpine, sodium phosphate, and benzalkonium chloride. In embodiments, the microdroplet or aqueous pharmaceutical composition comprises pilocarpine, sodium phosphate, benzalkonium chloride, and sodium chloride. In embodiments, the microdroplet or aqueous pharmaceutical composition comprises from about 0.01 wt % to about 3 wt % pilocarpine. In embodiments, the microdroplet or aqueous pharmaceutical composition comprises from about 0.01 wt % to about 3 wt % pilocarpine, about 0.1 wt % to about 0.2 wt % sodium phosphate, about 0.001 wt % to about 0.02 wt % benzalkonium chloride, and about 0.2 wt % to about 0.6 wt % sodium chloride. In embodiments, the microdroplet or aqueous pharmaceutical composition comprises from about 0.01 wt % to about 3 wt % pilocarpine, about 0.1 wt % to about 0.2 wt % sodium phosphate, about 0.001 wt % to about 0.02 wt % benzalkonium chloride, and about 0.6 wt % to about 1.0 wt % sodium chloride. In embodiments, the microdroplet or aqueous pharmaceutical composition comprises from about 0.05 wt % to about 1.5 wt % pilocarpine. In embodiments, the microdroplet or aqueous pharmaceutical composition comprises from about 0.05 wt % to about 1.5 wt % pilocarpine, about 0.1 wt % to about 0.2 wt % sodium phosphate, about 0.001 wt % to about 0.02 wt % benzalkonium chloride, and about 0.2 wt % to about 0.6 wt % sodium chloride. In embodiments, the microdroplet or aqueous pharmaceutical composition comprises from about 0.05 wt % to about 1.5 wt % pilocarpine, about 0.1 wt % to about 0.2 wt % sodium phosphate, about 0.001 wt % to about 0.02 wt % benzalkonium chloride, and about 0.6 wt % to about 1.0 wt % sodium chloride. In embodiments, the microdroplet or aqueous pharmaceutical composition comprises about 1.0 wt % pilocarpine, about 0.136% wt % sodium phosphate, about 0.011 wt % benzalkonium chloride, and about 0.4 wt % sodium chloride. In embodiments, the microdroplet or aqueous pharmaceutical composition comprises about 1.0 wt % pilocarpine, about 0.136 wt % sodium phosphate, about 0.011 wt % benzalkonium chloride, and about 0.8 wt % sodium chloride. In embodiments, the sodium phosphate comprises monobasic sodium phosphate, dibasic sodium phosphate, or a mixture thereof. In embodiments, the sodium phosphate comprises monobasic sodium phosphate. In embodiments, the sodium phosphate comprises dibasic sodium phosphate. In embodiments, the sodium phosphate comprises monobasic sodium phosphate and dibasic sodium phosphate. In embodiments, the microdroplet or aqueous pharmaceutical composition comprises is a solution. In embodiments, the microdroplet or aqueous pharmaceutical composition further comprises an acid (e.g., HCl) or a base (e.g., NaOH) to adjust the pH of the solution from about 7 to about 7.3. In embodiments, the microdroplet or aqueous pharmaceutical composition is a solution. In embodiments, the medicament is a microdroplet. In embodiments, the medicament is a plurality of microdroplets. In embodiments, the medicament is an aqueous pharmaceutical composition having a volume from about 1 ml to about 10 ml. In embodiments, the aqueous pharmaceutical composition has a volume from about 2 ml to about 5 ml. In embodiments, the aqueous pharmaceutical composition has a volume from about 2.5 ml to about 3 ml. In embodiments, the microdroplet or aqueous pharmaceutical composition is a piezo-enabled formulation capable of causing fluid movement.

In embodiments, the microdroplet or aqueous pharmaceutical composition comprises from about 1.5 wt % to about 2.5 wt % pilocarpine. In embodiments, the microdroplet or aqueous pharmaceutical composition comprises from about 1.5 wt % to about 2.5 wt % pilocarpine. In embodiments, the microdroplet or aqueous pharmaceutical composition comprises from about 1.5 wt % to about 2.5 wt % pilocarpine, about 0.1 wt % to about 0.2 wt % sodium phosphate, about 0.001 wt % to about 0.02 wt % benzalkonium chloride, and about 0.2 wt % to about 0.6 wt % sodium chloride. In embodiments, the microdroplet or aqueous pharmaceutical composition comprises about 2.0 wt % pilocarpine, about 0.136% wt % sodium phosphate, about 0.011 wt % benzalkonium chloride, and about 0.4 wt % sodium chloride. In embodiments, the microdroplet or aqueous pharmaceutical composition comprises about 2.0 wt % pilocarpine, about 0.136 wt % sodium phosphate, about 0.011 wt % benzalkonium chloride, and about 0.8% wt sodium chloride. In embodiments, the sodium phosphate comprises monobasic sodium phosphate, dibasic sodium phosphate, or a mixture thereof. In embodiments, the sodium phosphate comprises monobasic sodium phosphate. In embodiments, the sodium phosphate comprises dibasic sodium phosphate. In embodiments, the sodium phosphate comprises monobasic sodium phosphate and dibasic sodium phosphate. In embodiments, the microdroplet or aqueous pharmaceutical composition comprises is a solution. In embodiments, the microdroplet or aqueous pharmaceutical composition further comprises an acid (e.g., HCl) or a base (e.g., NaOH) to adjust the pH of the solution from about 7 to about 7.3. In embodiments, the microdroplet or aqueous pharmaceutical composition is a solution. In embodiments, the medicament is a microdroplet. In embodiments, the medicament is a plurality of microdroplets. In embodiments, the medicament is an aqueous pharmaceutical composition having a volume from about 1 ml to about 10 ml. In embodiments, the aqueous pharmaceutical composition has a volume from about 2 ml to about 5 ml. In embodiments, the aqueous pharmaceutical composition has a volume from about 2.5 ml to about 3 ml. In embodiments, the microdroplet or aqueous pharmaceutical composition is a piezo-enabled formulation capable of causing fluid movement.

Additional medicaments and their formulations are described in detail in U.S. Publication No. 20170344714, which is incorporated herein by reference.

Aspects of the subject matter described herein may be realized in digital electronic circuitry, integrated circuitry, specially designed ASICs (application specific integrated circuits), computer hardware, firmware, software, and/or combinations thereof. These various implementations may include an implementation in one or more computer programs that are executable and/or interpretable on a programmable system including at least one programmable processor, which may be special or general purpose, coupled to receive signals, data and instructions from, and to transmit signals, data, and instructions to, a storage system, at least one input device, and at least one output device.

These computer programs (also known as programs, software, software applications, or code) include machine instructions for a programmable processor, and may be implemented in a high-level procedural and/or object-oriented programming language, and/or in assembly/machine language. As used herein, the term "machine-readable medium" refers to any computer program product, apparatus, and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

In various implementations, description is made with reference to the figures. However, certain implementations may be practiced without one or more of these specific details, or in combination with other known methods and configurations. In the description, numerous specific details are set forth, such as specific configurations, dimensions, and processes, in order to provide a thorough understanding of the implementations. In other instances, well-known processes and manufacturing techniques have not been described in particular detail in order to not unnecessarily obscure the description. Reference throughout this specification to "one embodiment," "an embodiment," "one implementation," "an implementation," or the like, means that a particular feature, structure, configuration, or characteristic described is included in at least one embodiment or implementation. Thus, the appearance of the phrase "one embodiment," "an embodiment," "one implementation," "an implementation," or the like, in various places throughout this specification are not necessarily referring to the same embodiment or implementation. Furthermore, the particular features, structures, configurations, or characteristics may be combined in any suitable manner in one or more implementations.

The use of relative terms throughout the description may denote a relative position or direction. For example, "distal" or "lower" or "downwards" may indicate a first direction away from a reference point. Similarly, "proximal" or "upper" or "upwards" may indicate a location in a second direction opposite to the first direction. However, such terms are provided to establish relative frames of reference, and are not intended to limit the use or orientation of the device to a specific configuration described in the various implementations.

The word "about" means a range of values including the specified value, which a person of ordinary skill in the art would consider reasonably similar to the specified value. In embodiments, about means within a standard deviation using measurements generally acceptable in the art. In embodiments, about means a range extending to +/−10% of the specified value. In embodiments, about includes the specified value While this specification contains many specifics, these should not be construed as limitations on the scope of what is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results. Only a few examples and implementations are disclosed. Variations, modifications and enhancements to the described examples and implementations and other implementations may be made based on what is disclosed.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;"

"one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together."

Use of the term "based on," above and in the claims is intended to mean, "based at least in part on," such that an unrecited feature or element is also permissible.

What is claimed is:

1. A device for delivering a volume of fluid to an eye, the device comprising:
    a base comprising a drive mechanism; and
    a disposable fluid cartridge configured to releasably couplet o the base to form the device, the cartridge comprising:
        a piezoelectric-driven fluid ejector;
        a fluid container comprising:
            a reservoir manifold having an exit port;
            a reservoir film movably coupled to the reservoir manifold; and
            a manifold film positioned within the exit port,
        wherein the reservoir manifold, manifold film, and reservoir film define an internal volume of the container that is sized to hold a plurality of doses of a therapeutic agent; and
    a pump comprising:
        a pumping manifold defining an inner bore comprising a first region having a first inner diameter and a second region having a second inner diameter, the second inner diameter being larger than the first diameter;
        a drive spool slidingly positioned within the inner bore and comprising a first sliding seal element; and
        a floating spool movably coupled to the drive spool and slidingly positioned within the inner bore and comprising a second siding seal element,
        wherein each of the first sliding seal element and the second sliding seal element is sized to seal with the first region of the inner bore, and wherein sealing between the second sliding seal element and the first region of the inner bore is released upon positioning the second sliding seal element within the second region of the inner bore,
        wherein the pump is configured to draw a dose from the plurality of doses held in the fluid container past the second sliding seal element positioned within the second region into a space between the first sliding seal element and the second sliding seal element and deliver the dose to the fluid ejector.

2. The device of claim 1, wherein the fluid ejector is configured to eject the dose as a horizontal stream of microdroplets to a cornea of an eye.

3. The device of claim 1, wherein the reservoir film tents outward from the reservoir manifold and collapses inward toward the reservoir manifold dependent upon the plurality of doses contained within the internal volume.

4. The device of claim 1, wherein the reservoir film collapses towards the reservoir manifold as the dose is drawn from the internal volume by the pump.

5. The device of claim 1, wherein the fluid container includes no vent.

6. The device of claim 1, wherein the internal volume of the container remains sealed from ambient air during use by the first sliding seal element and the second sliding seal element.

7. The device of claim 1, wherein the reservoir film is a flexible, non-permeable material.

8. The device of claim 7, wherein the flexible, non-permeable material is a polymer or foil.

9. The device of claim 7, wherein the reservoir film is not elastic or stretchy.

10. The device of claim 1, wherein the reservoir manifold comprises a concave inner surface and a mating edge at an outer perimeter of the concave inner surface.

11. The device of claim 10, wherein the mating edge of the reservoir manifold mates with a corresponding outer perimeter of the reservoir film.

12. The device of claim 1, wherein the exit port is located on a lower end region of the reservoir manifold.

13. The device of claim 1, wherein the manifold film separates the internal volume of the container from a pumping manifold of the pump.

14. The device of claim 1, wherein the drive mechanism comprises a motor-driven cam configured to operatively couple with the pump.

15. The device of claim 1, further comprising a single actuator that, upon actuation, causes the pump to draw and deliver the dose to the fluid ejector, and activate the piezoelectric-driven fluid ejector to eject the dose to the eye.

16. The device of claim 1, further comprising a dose button.

17. The device of claim 16, wherein penetration of the manifold film occurs only upon actuation of the dose button.

18. The device of claim 16, further comprising a protective shutter arranged to cover the dose button and the fluid ejector.

19. The device of claim 18, wherein opening the protective shutter electronically wakes the base.

20. The device of claim 1, wherein the therapeutic agent is selected from the group consisting of tropicamide, phenylephrine, atropine, latanoprost, and pilocarpine.

21. The device of claim 1, wherein the therapeutic agent is for the treatment of glaucoma, presbyopia, myopia, or mydriasis.

22. A device for delivering a volume of fluid to an eye, the device comprising:
    a base comprising a motor-driven cam; and
    a disposable fluid cartridge configured to releasably couple to the base to form the device, the cartridge comprising:
        a piezoelectric-driven fluid ejector;
        a fluid container defining an internal volume sized to hold a plurality of doses of a therapeutic agent; and
        a pump configured to draw a dose form the plurality of doses held int eh container and deliver the dose to the fluid ejector, wherein the pump comprises:
            a pumping manifold defining an inner bore comprising a first region and a second region;
            a drive spool slidingly positioned within the inner bore and operatively coupled to the motor-driven cam, the drive spool comprising a first sliding seal element; and
            a floating spool movably coupled to the drive spool and slidingly positioned within the inner bore, wherein the floating spool comprises a second sliding seal element encircling an upper end portion of the floating spool, wherein a space is formed between the first sliding seal element and the second sliding seal element,
wherein positioning the second sliding seal element within the first region of the inner bore seals the space from being in fluid communication with the fluid container, and
wherein positioning the sliding seal element within the second region of the inner bore places the space in fluid communication with the fluid container allowing the dose to be drawn by the pump into the space.

23. The device of claim 22, wherein the fluid ejector is configured to eject the dose as a horizontal stream of microdroplets to a cornea of an eye.

24. The device of claim 22, further comprising a single actuator that, upon actuation, causes the pump to draw and deliver the dose to the fluid ejector, and activate the piezoelectric-driven fluid ejector to eject the dose to the eye.

25. The device of claim 22, further comprising a dose button.

26. The device of claim 25, further comprising a protective shutter arranged to cover the dose button and the fluid ejector.

27. The device of claim 26, wherein opening the protective shutter electronically wakes the base.

28. The device of claim 22, wherein the therapeutic agent is selected from the group consisting of tropicamide, phenylephrine, atropine, latanoprost, and pilocarpine.

29. The device of claim 22, wherein the therapeutic agent is for the treatment of glaucoma, presbyopia, myopia, or mydriasis.

30. The device of claim 22, wherein the drive spool comprises two sliding seals encircling a main body of the drive spool, the two sliding seals comprising an upper seal and a lower seal.

31. The device of claim 22, wherein sliding motion of the drive spool causes sliding motion of the floating spool when the floating spool is engaged with the drive spool.

32. The device of claim 22, wherein reciprocal, linear motion of the drive spool draws the dose from the fluid container and delivers the dose to the fluid ejector.

33. The device of claim 22, wherein a first amount of rotation by the motor-driven cam causes the drive spool and the floating spool to be urged toward the fluid container.

34. The device of claim 33, wherein the floating spool comprises a projection that pierces a manifold film of the fluid container placing the internal volume of the fluid container in fluid communication with the pumping manifold.

35. The device of claim 34, wherein a second amount of rotation by the motor-driven cam withdraws the drive spool away from the floating spool increasing a size of the space to draw the dose from the fluid container into the inner bore.

36. The device of claim 35, wherein a third amount of rotation draws the drive spool away from the floating spool until the drive spool and floating spool engage with one another and the drive spool pulls the floating spool through the inner bore until the dose in the space is aligned with the fluid ejector.

37. The device of claim 36, wherein a fourth amount of rotation urges the drive spool towards the floating spool collapsing the space and delivering the dose within the space to the fluid ejector.

38. The device of claim 22, wherein a volume of the dose is about equal to a cross-sectional area of the inner bore multiplied by a length of displacement between the drive spool and the floating spool.

39. The device of claim 38, wherein the length of displacement between the drive spool and the floating spool is about 0.100" to about 0.300" and the volume of the dose is about 2 ul to about 15 ul.

40. A device for delivering a volume of fluid to an eye, the device comprising:
a base comprising a drive mechanism; and
a disposable fluid cartridge configured to releasably couple to the base to form the device, the cartridge comprising:
a piezoelectric-driven fluid ejector;
a fluid container defining an internal volume sized to hold a plurality of doses of a therapeutic agent, the fluid container comprising an exit port having a manifold film positioned within the exit port; and
a pump configured to draw a dose from the plurality of doses held in the container and deliver the dose to the fluid ejector, the pump comprising:
a pumping manifold defining an inner bore separated from the internal volume of the fluid container by the manifold film positioned within the exit port;
a drive spool having a first end region operatively coupled to the drive mechanism and a second end region movably coupled to a floating spool, the drive spool and floating spool slidingly positioned within the inner bore,
wherein the drive spool comprises a first sliding seal element and the floating spool comprises a second sliding seal element, wherein a space is formed between the first sliding seal element and the second sliding seal element,
positioning the second sliding seal element within a first region of the inner bore seals the space from being in fluid communication with the internal volume of the fluid container, and
positioning the second sliding seal element within an upper inlet region of the inner bore places the space in fluid communication with the internal volume of the fluid container allowing the dose to be drawn by the pump into the space.

41. The device of claim 40, wherein the floating spool further comprises a projection arranged to place the inner bore in fluid with the internal volume of the fluid container, wherein the projection is configured to lift the manifold film relative to the exit port.

42. The device of claim 41, wherein the projection has a cutting edge geometry configured to pierce the manifold film.

43. The device of claim 42, wherein the cutting edge geometry allows for fluid to pass around the projection when the projection pierces the manifold film.

44. The device of claim 40, wherein the first region of the inner bore has a first inner diameter and the upper inlet region has a second inner diameter, the first inner diameter is smaller than the second inner diameter so as to create a seal between the first region of the inner bore and the first sliding seal element.

45. The device of claim 44, wherein the upper inlet region comprises a plurality of surface features that prevent the first sliding seal element from sealing with the upper inlet region.

46. The device of claim 44, wherein first sliding seal element is compressed between a surface of the floating spool and walls of the inner bore to create the seal.

47. The device of claim 40, wherein the space between the first sliding seal element and the second sliding seal element forms a variable volume pumping chamber.

48. The device of claim 47, wherein withdrawing the drive spool away from the floating spool increases a size of the variable volume pumping chamber and creates a vacuum within the pumping chamber to draw fluid from the internal volume of the fluid container.

49. The device of claim 41, wherein the projection is eccentric relative to an upper surface of the floating spool.

50. The device of claim 40, wherein a reservoir manifold of the fluid container slopes downwards towards the exit port.

51. The device of claim 40, wherein a wetted delivery flow path extends between a lower end of the fluid container to the fluid ejector through the inner bore.

52. The device of claim 51, wherein the wetted delivery flow path is L-shaped and has a length that is between about 0.5 inch and 1.0 inch.

\* \* \* \* \*